(12) United States Patent
Schmitt et al.

(10) Patent No.: US 7,575,925 B2
(45) Date of Patent: Aug. 18, 2009

(54) CELL PREPARATIONS COMPRISING CELLS OF THE T CELL LINEAGE AND METHODS OF MAKING AND USING THEM

(75) Inventors: Thomas M. Schmitt, Toronto (CA); Juan Carlos Zuniga-Pflucker, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 0 days.

(21) Appl. No.: 10/731,741

(22) Filed: Dec. 10, 2003

(65) Prior Publication Data

US 2004/0171148 A1 Sep. 2, 2004

Related U.S. Application Data

(60) Provisional application No. 60/432,525, filed on Dec. 10, 2002.

(51) Int. Cl.
*C12N 5/08* (2006.01)
*C12N 5/06* (2006.01)

(52) U.S. Cl. ............... 435/372.3; 435/372; 435/325

(58) Field of Classification Search ............... 435/325, 435/2, 372, 372.3; 536/23.1
See application file for complete search history.

(56) References Cited

OTHER PUBLICATIONS

Gearhart, J. New Potential for Human Embryonic Stem Cells (1998) Science 282:1061-1062.*
Thomson et al. Embryonic Stem Cell Lines Drived from Human Blastocysts. (1998) Science 282:1145-1147.*
Campbell et al., Totipotentcyor multipotentiality of cultured cells: Aplications and Prgress. (1997) Theriogenology 47:63-72.*
Jaleco et al. (2001) Differential Effects of Notch Ligands Delta-1 and Jagged-1 in Human Lymphoid Differentiation. J. Exp. Med. 194:991-1001.*
Lehar et al. (2002) T cell Development in Culture. Immunity 17:689-692.*
Schmitt et al. (2004) Induction of T cell development and establishment of T cell competence from embryonic stem cells differentiated in vitro. Nat. Immunology. 5:410-417.*
Rothenberg et al. (2004) From Totipotency to T in a dish. Nat. Immunology. 5:359-360.*
Lehar et al. (2004) Notch ligands Delta1 and Jagged1 transmit distinct signals to T cell precursors. Blood. DOI 10.1182/blood-2004-08-3257. 1-38.*
Abbas et al., (1994) Cellular and Molecular Immunology 2nd ed., 1-457.*
Tatsumi et al. (1990) Differentiation of thymocytes from CD3-CD4-CD8-through CD3-CD4-CD8+ into more mature stages induced by a thymic stromal cell clone. Proc. Natl. Acad Sci. 87:2750-2754.*
Nakano et al. (1994) Generation of Lymphohematopoietic cells from embryonic stem cells in culture. Science. 265:1098-1101.*
Pui et al Immunity. 1999, 11(3):299-308.*
Schmitt et al. 2002 Induction of T Cell Development from Hematopoietic Progenitor Cells by Dleta-like-1 In Vitro. Immunity, vol. 17, 749-756.
Lehar and Bevan 2002. T Cell Development in Culture. Immunity vol. 17, 689-692.
Nakano et al 1994 Generation of Lymphohematopoietic Cells from Embryonic Stem Cells in Culture. Science, vol. 265, 1098-1101.
Hare et al 1999. In vitro models of T cell development. Semin Immunol 11(1) , 3-12.
Dorsch et al 2002. Ectopic expression of Delta4 impairs hematopoietic development and leads to lymphoproliferative disease. Blood vol. 100(6) , 2046-55.
Mailhos et al 2001. Delta4, an endothelial specific notch ligand expressed at sites of physiological and tumor angiogenesis. Differentiation vol. 69(2-3) 135-44.
Eto et al 2002. Megakaryocytes derived from embryonic stem cells implicate CalDAG-GEFI in integrin signaling. Proc Natl Acad Sci. vol. 99 (20), 12819-24.
Artavanis-Tsakonas et al 1999. Notch Signaling: Cell Fate Control and Signal Integration in Development Science vol. 28, 770-776.

* cited by examiner

*Primary Examiner*—Valarie Bertoglio
*Assistant Examiner*—Anoop Singh
(74) *Attorney, Agent, or Firm*—Bereskin & Parr; Micheline Gravelle

(57) ABSTRACT

The invention relates to cell preparations comprising cells of the T cell lineage, methods for preparing same, and uses of the cell preparations.

8 Claims, 16 Drawing Sheets a)

b)

c)

a.

ESCs cultured on OP9-DL1

Ex vivo Thymocytes b.

Unstimulated

αCD3/CD28 Stimulation

SEQUENCE LISTING

```
<160> NUMBER OF SEQ ID NOS: 50

<210> SEQ ID NO 1
<211> LENGTH: 723
<212> TYPE: PRT
<213> ORGANISM: Homo sapiens

<400> SEQUENCE: 1

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240
```

-continued

Gly Glu Cys Lys Cys Arg Val Gly Trp Gln Gly Arg Tyr Cys Asp Glu
            245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
            275                 280                 285
Leu Asn Tyr Cys Thr His His Lys Pro Cys Lys Asn Gly Ala Thr Cys
        290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
            355                 360                 365
Thr Cys Ala Asp Gly Pro Cys Phe Asn Gly Gly Arg Cys Ser Asp Ser
        370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Ser Pro Cys Ser Asn
                405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
            435                 440                 445
Ser Ser Pro Cys Ala Asn Gly Gly Thr Cys Arg Asp Gly Val Asn Asp
        450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Glu Arg Gly His Gly Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
            515                 520                 525
Val Val Asp Leu Thr Glu Lys Leu Glu Gly Gln Gly Gly Pro Phe Pro
        530                 535                 540
Trp Val Ala Val Cys Ala Gly Val Ile Leu Val Leu Met Leu Leu Leu
545                 550                 555                 560
Gly Cys Ala Ala Val Val Cys Val Arg Leu Arg Leu Gln Lys His
                565                 570                 575
Arg Pro Pro Ala Asp Pro Cys Arg Gly Glu Thr Glu Thr Met Asn Asn
            580                 585                 590
Leu Ala Asn Cys Gln Arg Glu Lys Asp Ile Ser Val Ser Ile Ile Gly
            595                 600                 605
Ala Thr Gln Ile Lys Asn Thr Asn Lys Lys Ala Asp Phe His Gly Asp
        610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                645                 650                 655

```
Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
            675                 680                 685

Arg Lys Arg Pro Asp Ser Gly Cys Ser Thr Ser Lys Asp Thr Lys Tyr
            690                 695                 700

Gln Ser Val Tyr Val Ile Ser Glu Glu Lys Asp Glu Cys Val Ile Ala
705                 710                 715                 720

Thr Glu Val

<210> SEQ ID NO 2
<211> LENGTH: 589
<212> TYPE: PRT
<213> ORGANISM: Rattus norvegicus

<400> SEQUENCE: 2

Met Val Ser Leu Gln Val Ser Ser Leu Pro Gln Thr Leu Ile Leu Ala
1               5                   10                  15

Phe Leu Leu Pro Gln Ala Leu Pro Ala Gly Val Phe Glu Leu Gln Ile
            20                  25                  30

His Ser Phe Gly Pro Gly Pro Gly Pro Gly Thr Pro Arg Ser Pro Cys
            35                  40                  45

Asn Ala Arg Gly Pro Cys Arg Leu Phe Phe Arg Val Cys Leu Lys Pro
50                  55                  60

Gly Val Ser Gln Glu Ala Ala Glu Ser Leu Cys Ala Leu Gly Ala Ala
65                  70                  75                  80

Leu Ser Thr Ser Gly Pro Val Tyr Thr Glu Gln Pro Gly Val Pro Ala
            85                  90                  95

Ala Ala Leu Ser Leu Pro Asp Gly Leu Val Arg Val Pro Phe Leu Asp
            100                 105                 110

Ala Trp Pro Gly Thr Phe Ser Leu Ile Ile Glu Thr Trp Arg Glu Gln
            115                 120                 125

Leu Gly Glu Arg Ala Ala Gly Pro Ala Trp Asn Leu Leu Ala Arg Val
            130                 135                 140

Ala Gly Arg Arg Arg Leu Ala Ala Gly Ala Pro Trp Ala Arg Asp Val
145                 150                 155                 160

Gln Arg Thr Gly Ala Trp Glu Leu His Phe Ser Tyr Arg Ala Arg Cys
            165                 170                 175

Glu Pro Pro Ala Val Gly Ala Ala Cys Ala Arg Leu Cys Arg Ser Arg
            180                 185                 190

Ser Ala Pro Ser Arg Cys Gly Pro Gly Leu Arg Pro Cys Thr Pro Phe
            195                 200                 205

Pro Asp Glu Cys Glu Ala Pro Arg Glu Ser Leu Thr Val Cys Arg Ala
            210                 215                 220

Gly Cys Ser Pro Glu His Gly Tyr Cys Glu Glu Pro Asp Glu Cys His
225                 230                 235                 240

Cys Leu Glu Gly Trp Thr Gly Pro Leu Cys Thr Val Pro Val Ser Thr
            245                 250                 255

Ser Ser Cys Leu Asn Ser Arg Val Ser Gly Pro Ala Gly Thr Gly Cys
            260                 265                 270

Leu Leu Pro Gly Pro Gly Pro Cys Asp Gly Asn Pro Cys Ala Asn Gly
            275                 280                 285

Gly Ser Cys Ser Glu Thr Pro Gly Ser Phe Glu Cys Ala Cys Pro Arg
            290                 295                 300
```

```
Gly Phe Tyr Gly Pro Arg Cys Glu Val Ser Gly Val Thr Cys Ala Asp
305                 310                 315                 320

Gly Pro Cys Phe Asn Gly Gly Leu Cys Val Gly Gly Glu Asp Pro Asp
                325                 330                 335

Ser Ala Tyr Val Cys His Cys Pro Ala Phe Gln Ser Asn Cys
            340                 345                 350

Glu Arg Arg Val Asp Arg Cys Ser Leu Gln Pro Cys Gln Asn Gly Gly
        355                 360                 365

Leu Cys Leu Asp Leu Gly His Ala Leu Arg Cys Arg Cys Arg Ala Gly
    370                 375                 380

Phe Ala Gly Pro Arg Cys Glu His Asp Leu Asp Cys Ala Gly Arg
385                 390                 395                 400

Ala Cys Ala Asn Gly Gly Thr Cys Val Glu Gly Gly Gly Ala Arg Arg
                405                 410                 415

Cys Ser Cys Ala Leu Gly Phe Gly Gly Arg Asp Cys Arg Glu Arg Ala
                420                 425                 430

Asp Pro Cys Ala Ser Arg Pro Cys Ala His Gly Gly Arg Cys Tyr Ala
                435                 440                 445

His Phe Ser Gly Leu Val Cys Ala Cys Ala Pro Gly Tyr Met Gly Val
    450                 455                 460

Arg Cys Glu Phe Ala Val Arg Pro Asp Gly Ala Asp Ala Val Pro Ala
465                 470                 475                 480

Ala Pro Arg Gly Leu Arg Gln Ala Asp Ser Gln Arg Phe Leu Leu Pro
                485                 490                 495

Pro Ala Leu Gly Leu Leu Ala Ala Ala Ala Leu Ala Gly Ala Ala Leu
                500                 505                 510

Leu Leu Ile His Val Arg Arg Arg Gly Pro Gly Arg Asp Thr Gly Thr
    515                 520                 525

Arg Leu Leu Ser Gly Thr Arg Glu Pro Ser Val His Thr Leu Pro Asp
530                 535                 540

Ala Leu Asn Asn Leu Arg Leu Gln Asp Gly Ala Gly Asp Gly Pro Thr
545                 550                 555                 560

Ser Ser Ala Asp Trp Asn His Pro Glu Asp Gly Asp Ser Arg Ser Ile
                565                 570                 575

Tyr Val Ile Pro Ala Pro Ser Ile Tyr Ala Arg Glu Ala
                580                 585

<210> SEQ ID NO 3
<211> LENGTH: 723
<212> TYPE: PRT
<213> ORGANISM: Homo sapiens

<400> SEQUENCE: 3

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ala Gly Pro Pro Cys Ala Cys Arg Thr Phe Phe Arg Val Cys Leu
    50                  55                  60

Lys His Tyr Gln Ala Ser Val Ser Pro Glu Pro Cys Thr Tyr Gly
65              70                  75                  80

Ser Ala Val Thr Pro Val Leu Gly Val Asp Ser Phe Ser Leu Pro Asp
                85                  90                  95
```

```
Gly Gly Gly Ala Asp Ser Ala Phe Ser Asn Pro Ile Arg Phe Pro Phe
            100                 105                 110
Gly Phe Thr Trp Pro Gly Thr Phe Ser Leu Ile Ile Glu Ala Leu His
        115                 120                 125
Thr Asp Ser Pro Asp Asp Leu Ala Thr Glu Asn Pro Glu Arg Leu Ile
130                 135                 140
Ser Arg Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
        195                 200                 205
Glu Lys Val Cys Asn Pro Gly Trp Lys Gly Pro Tyr Cys Thr Glu Pro
    210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
                245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
        275                 280                 285
Leu Asn Tyr Cys Thr His His Lys Pro Cys Lys Asn Gly Ala Thr Cys
    290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
        355                 360                 365
Thr Cys Ala Asp Gly Pro Cys Phe Asn Gly Gly Arg Cys Ser Asp Ser
    370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Ser Pro Cys Ser Asn
                405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
        435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Gln Arg Gly His Gly Tyr Val Cys Glu Cys Ala Arg Ser Tyr Gly
            500                 505                 510
```

```
Gly Pro Asn Cys Gln Phe Leu Leu Pro Glu Leu Pro Pro Gly Pro Ala
            515                 520                 525

Val Val Asp Leu Thr Glu Lys Leu Glu Gly Gln Gly Gly Pro Phe Pro
        530                 535                 540

Trp Val Ala Val Cys Ala Gly Val Ile Leu Val Leu Met Leu Leu Leu
545                 550                 555                 560

Gly Cys Ala Ala Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
    610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
    690                 695                 700

Gln Ser Val Tyr Val Ile Ser Glu Glu Lys Asp Glu Cys Val Ile Ala
705                 710                 715                 720

Thr Glu Val

<210> SEQ ID NO 4
<211> LENGTH: 722
<212> TYPE: PRT
<213> ORGANISM: Mus musculus

<400> SEQUENCE: 4

Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ser Gly Pro Pro Cys Ala Cys Arg Thr Phe Phe Arg Val Cys Leu Lys
        50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
    130                 135                 140

Arg Leu Thr Thr Gln Arg His Leu Thr Val Gly Glu Glu Trp Ser Gln
145                 150                 155                 160
```

-continued

```
Asp Leu His Ser Ser Gly Arg Thr Asp Leu Arg Tyr Ser Tyr Arg Phe
            165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
            195                 200                 205

Lys Met Cys Asp Pro Gly Trp Lys Gly Gln Tyr Cys Thr Asp Pro Ile
            210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
            245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
            275                 280                 285

Asn Tyr Cys Thr His His Lys Pro Cys Arg Asn Gly Ala Thr Cys Thr
            290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
            325                 330                 335

Lys Asn Gly Ala Ser Cys Thr Asp Leu Glu Asp Ser Phe Ser Cys Thr
            340                 345                 350

Cys Pro Pro Gly Phe Tyr Gly Lys Val Cys Glu Leu Ser Ala Met Thr
            355                 360                 365

Cys Ala Asp Gly Pro Cys Phe Asn Gly Gly Arg Cys Ser Asp Asn Pro
            370                 375                 380

Asp Gly Gly Tyr Thr Cys His Cys Pro Leu Gly Phe Ser Gly Phe Asn
385                 390                 395                 400

Cys Glu Lys Lys Met Asp Leu Cys Gly Ser Ser Pro Cys Ser Asn Gly
            405                 410                 415

Ala Lys Cys Val Asp Leu Gly Asn Ser Tyr Leu Cys Arg Cys Gln Ala
            420                 425                 430

Gly Phe Ser Gly Arg Tyr Cys Glu Asp Asn Val Asp Asp Cys Ala Ser
            435                 440                 445

Ser Pro Cys Ala Asn Gly Gly Thr Cys Arg Asp Ser Val Asn Asp Phe
            450                 455                 460

Ser Cys Thr Cys Pro Pro Gly Tyr Thr Gly Lys Asn Cys Ser Ala Pro
465                 470                 475                 480

Val Ser Arg Cys Glu His Ala Pro Cys His Asn Gly Ala Thr Cys His
            485                 490                 495

Gln Arg Gly Gln Arg Tyr Met Cys Glu Cys Ala Gln Gly Tyr Gly Gly
            500                 505                 510

Pro Asn Cys Gln Phe Leu Leu Pro Glu Pro Pro Gly Pro Met Val
            515                 520                 525

Val Asp Leu Ser Glu Arg His Met Glu Ser Gln Gly Gly Pro Phe Pro
            530                 535                 540

Trp Val Ala Val Cys Ala Gly Val Val Leu Val Leu Leu Leu Leu Leu
545                 550                 555                 560

Gly Cys Ala Ala Val Val Val Cys Val Arg Leu Lys Leu Gln Lys His
            565                 570                 575
```

```
Gln Pro Pro Pro Glu Pro Cys Gly Gly Glu Thr Glu Thr Met Asn Asn
                575                 580                 585                 590

Leu Ala Asn Cys Gln Arg Glu Lys Asp Val Ser Val Ser Ile Ile Gly
            595                 600                 605

Ala Thr Gln Ile Lys Asn Thr Asn Lys Lys Ala Asp Phe His Gly Asp
610                 615                 620

His Gly Ala Lys Lys Ser Ser Phe Lys Val Arg Tyr Pro Thr Val Asp
625                 630                 635                 640

Tyr Asn Leu Val Arg Asp Leu Lys Gly Asp Glu Ala Thr Val Arg Asp
                645                 650                 655

Thr His Ser Lys Arg Asp Thr Lys Cys Gln Ser Gln Ser Ser Ala Gly
            660                 665                 670

Glu Glu Lys Ile Ala Pro Thr Leu Arg Gly Gly Glu Ile Pro Asp Arg
        675                 680                 685

Lys Arg Pro Glu Ser Val Tyr Ser Thr Ser Lys Asp Thr Lys Tyr Gln
690                 695                 700

Ser Val Tyr Val Leu Ser Ala Glu Lys Asp Glu Cys Val Ile Ala Thr
705                 710                 715                 720

Glu Val

<210> SEQ ID NO 5
<211> LENGTH: 589
<212> TYPE: PRT
<213> ORGANISM: Rattus norvegicus

<400> SEQUENCE: 5

Met Val Ser Leu Gln Val Ser Ser Leu Pro Gln Thr Leu Ile Leu Ala
1               5                   10                  15

Phe Leu Leu Pro Gln Ala Leu Pro Ala Gly Val Phe Glu Leu Gln Ile
                20                  25                  30

His Ser Phe Gly Pro Gly Pro Gly Pro Gly Thr Pro Arg Ser Pro Cys
            35                  40                  45

Asn Ala Arg Gly Pro Cys Arg Leu Phe Phe Arg Val Cys Leu Lys Pro
        50                  55                  60

Gly Val Ser Gln Glu Ala Ala Glu Ser Leu Cys Ala Leu Gly Ala Ala
65                  70                  75                  80

Leu Ser Thr Ser Gly Pro Val Tyr Thr Glu Gln Pro Gly Val Pro Ala
                85                  90                  95

Ala Ala Leu Ser Leu Pro Asp Gly Leu Val Arg Val Pro Phe Leu Asp
            100                 105                 110

Ala Trp Pro Gly Thr Phe Ser Leu Ile Ile Glu Thr Trp Arg Glu Gln
        115                 120                 125

Leu Gly Glu Arg Ala Ala Gly Pro Ala Trp Asn Leu Leu Ala Arg Val
    130                 135                 140

Ala Gly Arg Arg Arg Leu Ala Ala Gly Ala Pro Trp Ala Arg Asp Val
145                 150                 155                 160

Gln Arg Thr Gly Ala Trp Glu Leu His Phe Ser Tyr Arg Ala Arg Cys
                165                 170                 175

Glu Pro Pro Ala Val Gly Ala Ala Cys Ala Arg Leu Cys Arg Ser Arg
            180                 185                 190

Ser Ala Pro Ser Arg Cys Gly Pro Gly Leu Arg Pro Cys Thr Pro Phe
        195                 200                 205

Pro Asp Glu Cys Glu Ala Pro Arg Glu Ser Leu Thr Val Cys Arg Ala
    210                 215                 220
```

Gly Cys Ser Pro Glu His Gly Tyr Cys Glu Glu Pro Asp Glu Cys His
225                 230                 235                 240

Cys Leu Glu Gly Trp Thr Gly Pro Leu Cys Thr Val Pro Val Ser Thr
            245                 250                 255

Ser Ser Cys Leu Asn Ser Arg Val Ser Gly Pro Ala Gly Thr Gly Cys
        260                 265                 270

Leu Leu Pro Gly Pro Gly Pro Cys Asp Gly Asn Pro Cys Ala Asn Gly
            275                 280                 285

Gly Ser Cys Ser Glu Thr Pro Gly Ser Phe Glu Cys Ala Cys Pro Arg
290                 295                 300

Gly Phe Tyr Gly Pro Arg Cys Glu Val Ser Gly Val Thr Cys Ala Asp
305                 310                 315                 320

Gly Pro Cys Phe Asn Gly Gly Leu Cys Val Gly Gly Glu Asp Pro Asp
                325                 330                 335

Ser Ala Tyr Val Cys His Cys Pro Pro Ala Phe Gln Gly Ser Asn Cys
                340                 345                 350

Glu Arg Arg Val Asp Arg Cys Ser Leu Gln Pro Cys Gln Asn Gly Gly
                355                 360                 365

Leu Cys Leu Asp Leu Gly His Ala Leu Arg Cys Arg Cys Arg Ala Gly
370                 375                 380

Phe Ala Gly Pro Arg Cys Glu His Asp Leu Asp Asp Cys Ala Gly Arg
385                 390                 395                 400

Ala Cys Ala Asn Gly Gly Thr Cys Val Glu Gly Gly Ala Arg Arg
        405                 410                 415

Cys Ser Cys Ala Leu Gly Phe Gly Gly Arg Asp Cys Arg Glu Arg Ala
                420                 425                 430

Asp Pro Cys Ala Ser Arg Pro Cys Ala His Gly Gly Arg Cys Tyr Ala
            435                 440                 445

His Phe Ser Gly Leu Val Cys Ala Cys Ala Pro Gly Tyr Met Gly Val
450                 455                 460

Arg Cys Glu Phe Ala Val Arg Pro Asp Gly Ala Asp Ala Val Pro Ala
465                 470                 475                 480

Ala Pro Arg Gly Leu Arg Gln Ala Asp Ser Gln Arg Phe Leu Leu Pro
                485                 490                 495

Pro Ala Leu Gly Leu Leu Ala Ala Ala Ala Leu Ala Gly Ala Ala Leu
            500                 505                 510

Leu Leu Ile His Val Arg Arg Arg Gly Pro Gly Arg Asp Thr Gly Thr
            515                 520                 525

Arg Leu Leu Ser Gly Thr Arg Glu Pro Ser Val His Thr Leu Pro Asp
530                 535                 540

Ala Leu Asn Asn Leu Arg Leu Gln Asp Gly Ala Gly Asp Gly Pro Thr
545                 550                 555                 560

Ser Ser Ala Asp Trp Asn His Pro Glu Asp Gly Asp Ser Arg Ser Ile
            565                 570                 575

Tyr Val Ile Pro Ala Pro Ser Ile Tyr Ala Arg Glu Ala
            580                 585

<210> SEQ ID NO 6
<211> LENGTH: 685
<212> TYPE: PRT
<213> ORGANISM: Homo sapiens -continued

```
<400> SEQUENCE: 6

Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415
```

```
Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 7
<211> LENGTH: 686
<212> TYPE: PRT
<213> ORGANISM: Mus musculus

<400> SEQUENCE: 7

Met Thr Pro Ala Ser Arg Ser Ala Cys Arg Trp Ala Leu Leu Leu Leu
1               5                   10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
        35                  40                  45

Gln Ser Cys Glu Pro Gly Cys Arg Thr Phe Phe Arg Ile Cys Leu Lys
    50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95

Ser Gly Ser Gly Arg Asn Pro Leu Gln Leu Pro Phe Asn Phe Thr Trp
            100                 105                 110
```

-continued

```
Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
        130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                    165                 170                 175

Ser Asp Asn Tyr Tyr Gly Glu Ser Cys Ser Arg Leu Cys Lys Lys Arg
                180                 185                 190

Asp Asp His Phe Gly His Tyr Glu Cys Gln Pro Asp Gly Ser Leu Ser
            195                 200                 205

Cys Leu Pro Gly Trp Thr Gly Lys Tyr Cys Asp Gln Pro Ile Cys Leu
210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                    245                 250                 255

His Asn Gly Cys Arg His Gly Thr Cys Ser Ile Pro Trp Gln Cys Ala
                260                 265                 270

Cys Asp Glu Gly Trp Gly Gly Leu Phe Cys Asp Gln Asp Leu Asn Tyr
            275                 280                 285

Cys Thr His His Ser Pro Cys Lys Asn Gly Ser Thr Cys Ser Asn Ser
        290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                    325                 330                 335

Gly Gly Ser Cys Lys Asp Gln Glu Asn Ser Tyr His Cys Leu Cys Pro
                340                 345                 350

Pro Gly Tyr Tyr Gly Gln His Cys Glu His Ser Thr Leu Thr Cys Ala
            355                 360                 365

Asp Ser Pro Cys Phe Asn Gly Gly Ser Cys Arg Glu Arg Asn Gln Gly
        370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
                    405                 410                 415

Gln Cys Leu Asn Arg Gly Pro Ser Arg Thr Cys Arg Cys Arg Pro Gly
                420                 425                 430

Phe Thr Gly Thr His Cys Glu Leu His Ile Ser Asp Cys Ala Arg Ser
            435                 440                 445

Pro Cys Ala His Gly Gly Thr Cys His Asp Leu Glu Asn Gly Pro Val
        450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                    485                 490                 495

Tyr Thr Gly Leu Ser Pro Asn Asn Phe Val Cys Asn Cys Pro Tyr Gly
                500                 505                 510

Phe Val Gly Ser Arg Cys Glu Phe Pro Val Gly Leu Pro Pro Ser Phe
            515                 520                 525
```

```
Pro Trp Val Ala Val Ser Leu Gly Val Gly Leu Val Leu Leu Val
    530                 535                 540
Leu Leu Val Met Val Val Ala Val Arg Gln Leu Arg Leu Arg Arg
545                 550                 555                 560
Pro Asp Asp Glu Ser Arg Glu Ala Met Asn Asn Leu Ser Asp Phe Gln
                565                 570                 575
Lys Asp Asn Leu Ile Pro Ala Ala Gln Leu Lys Asn Thr Asn Gln Lys
            580                 585                 590
Lys Glu Leu Glu Val Asp Cys Gly Leu Asp Lys Ser Asn Cys Gly Lys
        595                 600                 605
Leu Gln Asn His Thr Leu Asp Tyr Asn Leu Ala Pro Gly Leu Leu Gly
    610                 615                 620
Arg Gly Ser Met Pro Gly Lys Tyr Pro His Ser Asp Lys Ser Leu Gly
625                 630                 635                 640
Glu Lys Val Pro Leu Arg Leu His Ser Glu Lys Pro Glu Cys Arg Ile
                645                 650                 655
Ser Ala Ile Cys Ser Pro Arg Asp Ser Met Tyr Gln Ser Val Cys Leu
            660                 665                 670
Ile Ser Glu Glu Arg Asn Glu Cys Val Ile Ala Thr Glu Val
        675                 680                 685

<210> SEQ ID NO 8
<211> LENGTH: 3158
<212> TYPE: DNA
<213> ORGANISM: Homo sapiens

<400> SEQUENCE: 8
aaaccggaac ggggcccaac ttctggggcc tggagaaggg aaacgaagtc ccccccggtt      60
tcccgaggtt gcctttcctc gggcatcctt ggtttcggcg ggacttcgca gggcggatat     120
aaagaacggc gcctttggga agaggcggag accggcttta agaaagaag tcttggtcct     180 gcggcttggg cgaggcaagg gcgaggcaag ggcgctttct gccgacgctc cccgtggccc     240
tacgatcccc cgcgcgtccg ccgctgttct aaggagagaa gtgggggccc ccaggctcg     300 cgcgtggagc gaagcagcat gggcagtcgg tgcgcgctgg ccctggcggt gctctcggcc     360
ttgctgtgtc aggtctggag ctctgggggtg ttcgaactga agctgcagga gttcgtcaac     420 aagaagggc tgctggggaa ccgcaactgc tgccgcgggg gcgcggggcc accgccgtgc     480
gcctgccgga ccttcttccg cgtgtgcctc aagcactacc aggccagcgt gtcccccgag     540
ccgccctgca cctacggcag cgccgtcacc ccgtgctggg gcgtcgactc cttcagtctg     600
cccgacggcg ggggcgccga ctccgcgttc agcaaccca tccgcttccc cttcggcttc     660
acctggccgg gcaccttctc tctgattatt gaagctctcc acacagattc tcctgatgac     720
ctcgcaacag aaaacccaga aagactcatc agccgcctgg ccacccagag gcacctgacg     780
gtgggcgagg agtggtccca ggacctgcac agcagcggcc gcacggacct caagtactcc     840
taccgcttcg tgtgtgacga acactactac ggagagggct gctccgtttt ctgccgtccc     900
cgggacgatg ccttcggcca cttcacctgt ggggagcgtg gggagaaagt gtgcaaccct     960
ggctggaaag ggccctactg cacagagccg atctgcctgc ctggatgtga tgagcagcat    1020
ggattttgtg acaaaccagg ggaatgcaag tgcagagtgg gctggcaggg ccggtactgt    1080
gacgagtgta tccgctatcc aggctgtctc catggcacct gccagcagcc tggcagtgc     1140 aactgccagg aaggctgggg gggccttttc tgcaaccagg acctgaacta ctgcacacac    1200
cataagccct gcaagaatgg agccacctgc accaacacgg gccaggggag ctacacttgc    1260
```

-continued

```
tcttgccggc ctgggtacac aggtgccacc tgcgagctgg ggattgacga gtgtgacccc      1320
agcccttgta agaacggagg gagctgcacg gatctcgaga cagctactc ctgtacctgc       1380
ccacccggct tctacggcaa aatctgtgaa ttgagtgcca tgacctgtgc ggacggccct      1440
tgctttaacg ggggtcggtg ctcagacagc cccgatggag ggtacagctg ccgctgcccc     1500
gtgggctact ccggcttcaa ctgtgagaag aaaattgact actgcagctc ttcaccctgt     1560
tctaatggtg ccaagtgtgt ggacctcggt gatgcctacc tgtgccgctg ccaggccggc    1620
ttctcgggga ggcactgtga cgacaacgtg gacgactgcg cctcctcccc gtgcgccaac    1680
gggggcacct gccgggatgg cgtgaacgac ttctcctgca cctgcccgcc tggctacacg    1740
ggcaggaact gcagtgcccc cgtcagcagg tgcgagcacg caccctgcca caatggggcc    1800
acctgccacc agaggggcca cggctatgtg tgcgaatgtg cccgaagcta cggggtccc    1860
aactgccagt tcctgctccc cgagctgccc ccgggcccag cggtggtgga cctcactgag   1920
aagctagagg gccagggcgg gccattcccc tgggtggccg tgtgcgccgg ggtcatcctt    1980
gtcctcatgc tgctgctggg ctgtgccgct gtggtggtct gcgtccggct gaggctgcag    2040
aagcaccggc ccccagccga cccctgccgg ggggagacgg agaccatgaa caacctggcc    2100
aactgccagc gtgagaagga catctcagtc agcatcatcg gggccacgca gatcaagaac    2160
accaacaaga aggcggactt ccacggggac acagcgccg acaagaatgg cttcaaggcc     2220
cgctacccag cggtggacta taacctcgtg caggacctca agggtgacga caccgccgtc    2280
agggacgcgc acagcaagcg tgacaccaag tgccagcccc agggctcctc aggggaggag     2340
aaggggaccc cgaccacact cagggggtgga gaagcatctg aaagaaaaag gccggactcg    2400
ggctgttcaa cttcaaaaga caccaagtac cagtcggtgt acgtcatatc cgaggagaag   2460
gatgagtgcg tcatagcaac tgaggtgtaa aatggaagtg agatggcaag actcccgttt    2520
ctcttaaaat aagtaaaatt ccaaggatat atgcccaac gaatgctgct gaagaggagg    2580
gaggcctcgt ggactgctgc tgagaaaccg agttcagacc gagcaggttc tcctcctgag    2640
gtcctcgacg cctgccgaca gcctgtcgcg gccgggccgc ctgcggcact gccttccgtg    2700
acgtcgccgt tgcactatgg acagttgctc ttaagagaat atatatttaa atgggtgaac     2760
tgaattacgc ctaagaagca tgcactgcct gagtgtatat tttggattct tatgagccag    2820
tcttttcttg aattagaaac acaaacactg cctttattgt cctttttgat acgaagatgt    2880
gcttttctta gatggaaaag atgtgtgtta tttttggat ttgtaaaaat atttttcatg    2940
atatctgtaa agcttgagta ttttgtgatg ttcgttttt ataattaaa ttttggtaaa    3000
tatgtacaaa ggcacttcgg gtctatgtga ctatatttt ttgtatataa atgtatttat    3060
ggatatttgt gccaatgtta tttgagtttt ttactgtttt gttaatgaag aaattccttt     3120
ttaaaatatt tttccaaaat aaatttttatg aggaattc                            3158
```

<210> SEQ ID NO 9
<211> LENGTH: 2857
<212> TYPE: DNA
<213> ORGANISM: Mus musculus

<400> SEQUENCE: 9

```
gtccagcggt accatgggcc gtcggagcgc gctagcccct gccgtggtct ctgccctgct      60
gtgccaggtc tggagctccg gcgtatttga gctgaagctg caggagttcg tcaacaagaa     120
ggggctgctg ggaaccgca actgctgccg cggggctct ggcccgcctt cgcctgcag      180
gaccttcttt cgcgtatgcc tcaagcacta ccaggccagc gtgtcaccgg agccacctg     240
```

```
cacctacggc agtgctgtca cgccagtgct gggtgtcgac tccttcagcc tgcctgatgg    300
cgcaggcatc gaccccgcct tcagcaaccc catccgattc cccttcggct tcacctggcc    360
aggtaccttc tctctgatca ttgaagccct ccatacagac tctcccgatg acctcgcaac    420
agaaaaccca gaaagactca tcagccgcct gaccacacag aggcacctca ctgtgggaga    480
agaatggtct caggaccttc acagtagcgg ccgcacagac ctccggtact cttaccggtt    540
tgtgtgtgac gagcactact acggagaagg ttgctctgtg ttctgccgac ctcgggatga    600
cgcctttggc cacttcacct gcggggacag aggggagaag atgtgcgacc ctggctggaa    660
aggccagtac tgcactgacc caatctgtct gccagggtgt gatgaccaac atggatactg    720
tgacaaacca ggggagtgca agtgcagagt tggctggcag ggccgctact gcgatgagtg    780
catccgatac ccaggttgtc tccatggcac ctgccagcaa ccctggcagt gtaactgcca    840
ggaaggctgg gggggccttt tctgcaacca agacctgaac tactgtactc accataagcc    900
gtgcaggaat ggagccacct gcaccaacac gggccagggg agctacacat gttcctgccg    960
acctgggtat acaggtgcca actgtgagct ggaagtagat gagtgtgctc ctagcccctg   1020
caagaacgga gcgagctgca cggaccttga ggacagcttc tcttgcacct gcctcccgg    1080 cttctatggc aaggtctgtg agctgagcgc catgacctgt gcagatggcc cttgcttcaa   1140
tggaggacga tgttcagata accctgacgg aggctacacc tgccattgcc ccttgggctt   1200
ctctggcttc aactgtgaga agaagatgga tctctgcggc tcttcccctt gttctaacgg   1260
tgccaagtgt gtggacctcg caactcttac cctgtgccgg tgccaggctg gcttctccgg   1320
gaggtactgc gaggacaatg tggatgactg tgcctcctcc ccgtgtgcaa atgggggcac   1380
ctgccgggac agtgtgaacg acttctcctg tacctgccca cctggctaca cgggcaagaa   1440
ctgcagcgcc cctgtcagca ggtgtgagca tgcaccctgc ataatgggg ccacctgcca   1500 ccagaggggc cagcgctaca tgtgtgagtg cgcccagggc tatggcggcc caactgcca    1560 gtttctgctc cctgagccac caccagggcc catggtggtg gacctcagtg agaggcatat   1620
ggagagccag ggcgggccct tcccctgggt ggccgtgtgt gccggggtgg tgcttgtcct   1680
cctgctgctg ctgggctgtg ctgctgtggt ggtctgcgtc cggctgaagc tacagaaaca   1740
ccagcctcca cctgaaccct gtgggggaga tacagaaacc atgaacaacc tagccaattg   1800
ccagcgcgag aaggacgttt ctgttagcat cattggggct acccagatca agaacaccaa   1860
caagaaggcg actttcacg gggaccatgg agccaagaag agcagcttta aggtccgata   1920 cccccactgtg gactataacc tcgttcgaga cctcaaggga gatgaagcca cggtcaggga   1980
tacacacagc aaacgtgaca ccaagtgcca gtcacagagc tctgcaggag aagagaagat   2040
cgccccaaca cttaggggtg gggagattcc tgacagaaaa aggccagagt ctgtctactc   2100
tacttcaaag gacaccaagt accagtcggt gtatgttctg tctgcagaaa aggatgagtg   2160
tgttatagcg actgaggtgt aagatggaag cgatgtggca aaattcccat ttctctcaaa   2220
taaaattcca aggatatagc cccgatgaat gctgctgaga gaggaaggga gaggaaaccc   2280
agggactgct gctgagaacc aggttcaggc gaagctggtt ctctcagagt tagcagaggc   2340 gccccgacact gccagcctag gctttggctg ccgctggact gcctgctggt tgttcccatt   2400
gcactatgga cagttgcttt gaagagtata tatttaaatg gacgagtgac ttgattcata   2460
taggaagcac gcactgccca cacgtctatc ttggattact atgagccagt ctttccttga   2520
actagaaaca caactgcctt tattgtcctt tttgatactg agatgtgttt ttttttttcc   2580
tagacgggaa aagaaaaacg tgtgttattt tttgggatt tgtaaaaata tttttcatga   2640
```

-continued

| | |
|---|---|
| tatctgtaaa gcttgagtat tttgtgacgt tcattttttt ataatttaaa ttttggtaaa | 2700 |
| tatgtacaaa ggcacttcgg gtctatgtga ctatattttt ttgtatataa atgtatttat | 2760 |
| ggaatattgt gcaaatgtta tttgagtttt ttactgtttt gttaatgaag aaattcattt | 2820 |
| taaaaatatt tttccaaaat aaatataatg aactaca | 2857 |

<210> SEQ ID NO 10
<211> LENGTH: 2058
<212> TYPE: DNA
<213> ORGANISM: Homo sapiens

<400> SEQUENCE: 10

| | |
|---|---|
| atggcggcag cgtcccggag cgcctctggc tgggcgctac tgctgctggt ggcactttgg | 60 |
| cagcagcgcg cggccggctc cggcgtcttc cagctgcagc tgcaggagtt catcaacgag | 120 |
| cgcggcgtac tggccagtgg gcggccttgc gagcccggct gccggacttt cttccgcgtc | 180 |
| tgccttaagc acttccaggc ggtcgtctcg cccggaccct gcaccttcgg gaccgtctcc | 240 |
| acgccggtat tgggcaccaa ctccttcgct gtccgggacg acagtagcgg cgggggcgc | 300 |
| aaccctctcc aactgccctt caatttcacc tggccgggta ccttctcgct catcatcgaa | 360 |
| gcttggcacg cgccaggaga cgacctgcgg ccagaggcct gccaccaga tgcactcatc | 420 |
| agcaagatcg ccatccaggg ctccctagct gtgggtcaga actggttatt ggatgagcaa | 480 |
| accagcaccc tcacaaggct gcgctactct taccgggtca tctgcagtga caactactat | 540 |
| ggagacaact gctcccgcct gtgcaagaag cgcaatgacc acttcggcca ctatgtgtgc | 600 |
| cagccagatg gcaacttgtc ctgcctgccc ggttggactg gggaatattg ccaacagcct | 660 |
| atctgtcttt cgggctgtca tgaacagaat ggctactgca gcaagccagc agagtgcctc | 720 |
| tgccgcccag gctggcaggg ccggctgtgt aacgaatgca tcccccacaa tggctgtcgc | 780 |
| cacggcacct gcagcactcc ctggcaatgt acttgtgatg agggctgggg aggcctgttt | 840 |
| tgtgaccaag atctcaacta ctgcacccac cactcccat gcaagaatgg gcaacgtgc | 900 |
| tccaacagtg ggcagcgaag ctacacctgc acctgtcgcc aggctacac tggtgtggac | 960 |
| tgtgagctgg agctcagcga gtgtgacagc aacccctgtc gcaatggagg cagctgtaag | 1020 |
| gaccaggagg atggctacca ctgcctgtgt cctccgggct actatggcct gcattgtgaa | 1080 |
| cacagcacct tgagctgcgc cgactccccc tgcttcaatg ggggctcctg ccgggagcgc | 1140 |
| aaccagggg ccaactatgc ttgtgaatgt cccccccaact tcaccggctc caactgcgag | 1200 |
| aagaaagtgg acaggtgcac cagcaaccc tgtgccaacg ggggacagtg cctgaaccga | 1260 |
| ggtccaagcc gcatgtgccg ctgccgtcct ggattcacgg gcacctactg tgaactccac | 1320 |
| gtcagcgact gtgcccgtaa cccttgcgcc cacggtggca cttgccatga cctggagaat | 1380 |
| gggctcatgt gcacctgccc tgccggcttc tctggccgac gctgtgaggt gcggacatcc | 1440 |
| atcgatgcct gtgcctcgag tccctgcttc aacaggggcca cctgctacac cgacctctcc | 1500 |
| acagacacct ttgtgtgcaa ctgcccttat ggctttgtgg gcagccgctg cgagttcccc | 1560 |
| gtgggcttgc cgcccagctt cccctgggtg gccgtctcgc tgggtgtggg gctggcagtg | 1620 |
| ctgctggtac tgctgggcat ggtggcagtg gctgtgcggc agctgcggct cgacggccg | 1680 |
| gacgacggca gcagggaagc catgaacaac ttgtcggact ccagaagga caacctgatt | 1740 |
| cctgccgccc agcttaaaaa cacaaaccag aagaaggagc tggaagtgga ctgtggcctg | 1800 |
| gacaagtcca actgtggcaa acagcaaaac cacacattgg actataatct ggccccaggg | 1860 |
| cccctggggc gggggaccat gccaggaaag tttccccaca gtgacaagag cttaggagag | 1920 |

```
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                  2058

<210> SEQ ID NO 11
<211> LENGTH: 3427
<212> TYPE: DNA
<213> ORGANISM: Mus musculus

<400> SEQUENCE: 11
ctcgcaggct aggaacccga ggccaagagc tgcagccaaa gtcacttggg tgcagtgtac      60
tccctcacta gcccgctcga gaccctagga tttgctccag acacgtact tagagcagcc     120 accgcccagt cgccctcacc tggattacct accgaggcat cgagcagcgg agttttgag     180 aaggcgacaa gggagcagcg tcccgagggg aatcagcttt tcaggaactc ggctggcaga     240
cgggacttgc gggagagcga catccctaac aagcagattc ggagtcccgg agtggagagg     300 acacccaag ggatgacgcc tgcgtcccgg agcgcctgtc gctgggcgct actgctgctg      360
gcggtactgt ggccgcagca gcgcgctgcg ggctccggca tcttccagct gcggctgcag     420
gagttcgtca ccagcgcgg tatgctggcc aatgggcagt cctgcgaacc gggctgccgg     480
actttcttcc gcatttgcct taagcacttc caggcaacct ctcccgaggg accctgcacc     540
tttggcaatg tctccacgcc ggtattgggc accaactcct tcgtcgtcag ggacaagaat     600
agcggcagtg tcgcaaccc tctgcagttg cccttcaatt tcacctggcc gggaaccttc     660
tcactcaaca tccaagcttg gcacacaccg ggagacgacc tgcggccaga gacttcgcca     720
ggaaactctc tcatcagcca aatcatcatc caaggctctc ttgctgtggg taagatttgg     780
cgaacagacg agcaaaatga caccctcacc agactgagct actcttaccg ggtcatctgc     840
agtgacaact actatggaga gagctgttct cgcctatgca agaagcgcga tgaccacttc     900
ggacattatg agtgccagcc agatggcagc ctgtcctgcc tgccgggctg gactgggaag     960
tactgtgacc agcctatatg tctttctggc tgtcatgagc agaatggtta ctgcagcaag    1020
ccagatgagt gcatctgccg tccaggttgg cagggtcgcc tgtgcaatga atgtatcccc    1080
cacaatggct gtcgtcatgg cacctgcagc atccctggc agtgtgcctg cgatgaggga    1140
tggggaggtc tgttttgtga ccaagatctc aactactgta ctcaccactc tccgtgcaag    1200
aatggatcaa cgtgttccaa cagtgggcca aagggttata cctgcacctg tctcccaggc    1260
tacactggtg agcactgtga gctgggactc agcaagtgtg ccagcaaccc ctgtcgaaat    1320
ggtggcagct gtaaggacca ggagaatagc taccactgcc tgtgtcccc aggctactat    1380 ggccagcact gtgagcatag taccttgacc tgtgcggact cccctgctt caatgggggc    1440 tcttgccggg agcgcaacca ggggtccagt tatgcctgcg aatgcccccc caactttacc    1500
ggctctaact gtgagaagaa agtagacagg tgtaccagca cccgtgtgc caatggaggc    1560 cagtgcctga acagaggtcc aagccgaacc tgccgctgcc ggcctggatt cacaggcacc    1620
cactgtgaac tgcacatcag cgattgtgcc cgaagtccct gtgcccacgg gggcacttgc    1680
cacgatctgg agaatgggcc tgtgtgcacc tgccccgctg gcttctctgg caggcgctgc    1740
gaggtgcgga taaccacga tgcctgtgcc tccggaccct gcttcaatgg gccacctgc    1800 tacactggcc tctccccaaa caacttcgtc tgcaactgtc cttatggctt tgtgggcagc    1860
cgctgcgagt ttcccgtggg cttgccaccc agcttccct gggtagctgt ctcgctgggc    1920
gtggggctag tggtactgct ggtgctgctg gtcatggtgg tagtggctgt gcggcagctg    1980
```

```
cggcttcgga ggcccgatga cgagagcagg gaagccatga acaatctgtc agacttccag    2040
aaggacaacc taatccctgc cgcccagctc aaaaacacaa accagaagaa ggagctggaa    2100
gtggactgtg gtctggacaa gtccaattgt ggcaaactgc agaaccacac attggactac    2160
aatctagccc cgggactcct aggacggggc agcatgcctg ggaagtatcc tcacagtgac    2220
aagagcttag gagagaaggt gccacttcgg ttacacagtg agaagccaga gtgtcgaata    2280
tcagccattt gctctcccag ggactctatg taccaatcag tgtgtttgat atcagaagag    2340
aggaacgagt gtgtgattgc cacagaggta taaggcagga gcctactcag acacccagct    2400
ccggcccagc agctgggcct tccttctgca ttgtttacat tgcatcctgt atgggacatc    2460
tttagtatgc acagtgctgc tctgcggagg aggagggaat ggcatgaact gaacagactg    2520
tgaacccgcc aagagttgca ccggctctgc acacctccag gagtctgcct ggcttcagat    2580
gggcagcccc gccaagggaa cagagttgag gagttagagg agcatcagtt gagctgatat    2640
ctaaggtgcc tctcgaactt ggacttgctc tgccaacagt ggtcatcatg gagctcttga    2700
ctgttctcca gagagtggca gtggccctag tgggtcttgg cgctgctgta gctcctgtgg    2760
gcatctgtat ttccaaagtg cctttgccca gactccatcc tcacagctgg gcccaaatga    2820
gaaagcagag aggaggcttg caaggatag gcctcccgca ggcagaacag ccttggagtt    2880
tggcattaag caggagctac tctgcaggtg aggaaagccc gaggagggga cacgtgtgac    2940
tcctgcctcc aaccccagca ggtggggtgc cacctgcagc ctctaggcaa gagttggtcc    3000
ttcccctggt cctggtgcct ctgggctcat gtgaacagat gggcttaggg cacgcccctt    3060
ttgccagcca ggggtacagg cctcactggg gagctcaggg ccttcatgct aaactcccaa    3120
taagggagat gggggggaagg gggctgtggc ctaggccctt ccctccctca cacccatttt    3180
tgggcccttg agcctgggct ccaccagtgc ccactgttgc cccgagacca accttgaagc    3240 cgatttcaa aaatcaataa tatgaggttt tgttttgtag tttattttgg aatctagtat     3300
tttgataatt taagaatcag aagcactggc ctttctacat tttataacat tattttgtat    3360
ataatgtgta tttataatat gaaacagatg tgtacataaa aaaaaaaaa aaaaaaaaa     3420 aaaaaaa                                                              3427

<210> SEQ ID NO 12
<211> LENGTH: 20
<212> TYPE: DNA
<213> ORGANISM: Mus musculus

<400> SEQUENCE: 12
ggagcggtgt gagggtgatg                                                  20

<210> SEQ ID NO 13
<211> LENGTH: 20
<212> TYPE: DNA
<213> ORGANISM: Mus musculus

<400> SEQUENCE: 13
atctgcggtg ggggaatgtc                                                  20

<210> SEQ ID NO 14
<211> LENGTH: 20
<212> TYPE: DNA
<213> ORGANISM: Mus musculus

<400> SEQUENCE: 14
tctctgaccc ctgccataac                                                  20
```

<210> SEQ ID NO 15
<211> LENGTH: 19
<212> TYPE: DNA
<213> ORGANISM: Mus musculus

<400> SEQUENCE: 15
tttacagggg ttgctctcg                                                    19

<210> SEQ ID NO 16
<211> LENGTH: 20
<212> TYPE: DNA
<213> ORGANISM: Mus musculus

<400> SEQUENCE: 16
gcaaagaagc cgtgtgtaaa                                                   20

<210> SEQ ID NO 17
<211> LENGTH: 20
<212> TYPE: DNA
<213> ORGANISM: Mus musculus

<400> SEQUENCE: 17
taatagccgc caatcaggtt                                                   20

<210> SEQ ID NO 18
<211> LENGTH: 20
<212> TYPE: DNA
<213> ORGANISM: Mus musculus

<400> SEQUENCE: 18
acctcgggat gacgcctttg                                                   20

<210> SEQ ID NO 19
<211> LENGTH: 19
<212> TYPE: DNA
<213> ORGANISM: Mus musculus

<400> SEQUENCE: 19
gaccaccaca gcagcacag                                                    19

<210> SEQ ID NO 20
<211> LENGTH: 20
<212> TYPE: DNA
<213> ORGANISM: Mus musculus

<400> SEQUENCE: 20
gcaccaactc cttcgtcgtc                                                   20

<210> SEQ ID NO 21
<211> LENGTH: 20
<212> TYPE: DNA
<213> ORGANISM: Mus musculus

<400> SEQUENCE: 21
tcacaaaaca gacctcccca                                                   20

<210> SEQ ID NO 22
<211> LENGTH: 685
<212> TYPE: PRT
<213> ORGANISM: Mus musculus

<400> SEQUENCE: 22

```
Met Thr Pro Ala Ser Arg Ser Ala Cys Arg Trp Ala Leu Leu Leu Leu
1               5                   10                  15
Ala Val Leu Trp Pro Gln Gln Arg Ala Ala Gly Ser Gly Ile Phe Gln
            20                  25                  30
Leu Arg Leu Gln Glu Phe Val Asn Gln Arg Gly Met Leu Ala Asn Gly
        35                  40                  45
Gln Ser Cys Glu Pro Gly Cys Arg Thr Phe Phe Arg Ile Cys Leu Lys
    50                  55                  60
His Phe Gln Ala Thr Phe Ser Glu Gly Pro Cys Thr Phe Gly Asn Val
65                  70                  75                  80
Ser Thr Pro Val Leu Gly Thr Asn Ser Phe Val Val Arg Asp Lys Asn
                85                  90                  95
Ser Gly Ser Gly Arg Asn Pro Leu Gln Leu Pro Phe Asn Phe Thr Trp
            100                 105                 110
Pro Gly Thr Phe Ser Leu Asn Ile Gln Ala Trp His Thr Pro Gly Asp
        115                 120                 125
Asp Leu Arg Pro Glu Thr Ser Pro Gly Asn Ser Leu Ile Ser Gln Ile
    130                 135                 140
Ile Ile Gln Gly Ser Leu Ala Val Gly Lys Ile Trp Arg Thr Asp Glu
145                 150                 155                 160
Gln Asn Asp Thr Leu Thr Arg Leu Ser Tyr Ser Tyr Arg Val Ile Cys
                165                 170                 175
Ser Asp Asn Tyr Tyr Gly Glu Ser Cys Ser Arg Leu Cys Lys Lys Arg
            180                 185                 190
Asp Asp His Phe Gly His Tyr Glu Cys Gln Pro Asp Gly Ser Leu Ser
        195                 200                 205
Cys Leu Pro Gly Trp Thr Gly Lys Tyr Cys Asp Gln Pro Ile Cys Leu
    210                 215                 220
Ser Gly Cys His Glu Gln Asn Gly Tyr Cys Ser Lys Pro Asp Glu Cys
225                 230                 235                 240
Ile Cys Arg Pro Gly Trp Gln Gly Arg Leu Cys Asn Glu Cys Ile Pro
                245                 250                 255
His Asn Gly Cys Arg His Gly Thr Cys Ser Ile Pro Trp Gln Cys Ala
            260                 265                 270
Cys Asp Glu Gly Trp Gly Gly Leu Phe Cys Asp Gln Asp Leu Asn Tyr
        275                 280                 285
Cys Thr His His Ser Pro Cys Lys Asn Gly Ser Thr Cys Ser Asn Ser
    290                 295                 300
Gly Pro Lys Gly Tyr Thr Cys Thr Cys Leu Pro Gly Tyr Thr Gly Glu
305                 310                 315                 320
His Cys Glu Leu Gly Leu Ser Lys Cys Ala Ser Asn Pro Cys Arg Asn
                325                 330                 335
Gly Gly Ser Cys Lys Asp Gln Glu Asn Ser Tyr His Cys Leu Cys Pro
            340                 345                 350
Pro Gly Tyr Tyr Gly Gln His Cys Glu His Ser Thr Leu Thr Cys Ala
        355                 360                 365
Asp Ser Pro Cys Phe Asn Gly Gly Ser Cys Arg Glu Arg Asn Gln Gly
    370                 375                 380
Ser Ser Tyr Ala Cys Glu Cys Pro Pro Asn Phe Thr Gly Ser Asn Cys
385                 390                 395                 400
Glu Lys Lys Val Asp Arg Cys Ser Asn Pro Cys Ala Asn Gly Gly
                405                 410                 415
```

```
Gln Cys Leu Asn Arg Gly Pro Ser Arg Thr Cys Arg Cys Arg Pro Gly
                420                 425                 430

Phe Thr Gly Thr His Cys Glu Leu His Ile Ser Asp Cys Ala Arg Ser
            435                 440                 445

Pro Cys Ala His Gly Gly Thr Cys His Asp Leu Glu Asn Gly Pro Val
        450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
            500                 505                 510

Phe Val Gly Ser Arg Cys Glu Phe Pro Val Gly Leu Pro Pro Cys Ser
        515                 520                 525

Pro Trp Val Ala Val Ser Leu Gly Val Gly Leu Val Val Leu Leu Val
530                 535                 540

Leu Leu Val Met Val Val Ala Val Arg Gln Leu Arg Leu Arg Arg
545                 550                 555                 560

Pro Asp Asp Glu Ser Arg Glu Ala Met Asn Asn Leu Ser Asp Phe Gln
                565                 570                 575

Lys Asp Asn Leu Ile Pro Ala Ala Gln Leu Lys Asn Thr Asn Gln Lys
            580                 585                 590

Lys Glu Leu Glu Val Asp Cys Gly Leu Asp Lys Ser Asn Cys Gly Lys
        595                 600                 605

Leu Gln Asn His Thr Leu Asp Tyr Asn Leu Ala Pro Gly Leu Leu Gly
        610                 615                 620

Arg Gly Ser Met Pro Gly Lys Tyr Pro His Ser Asp Lys Ser Ile Gly
625                 630                 635                 640

Gln Gly Ala Thr Ser Val Thr His Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 23
<211> LENGTH: 653
<212> TYPE: PRT
<213> ORGANISM: Homo sapiens

<400> SEQUENCE: 23

Gln Leu Gln Glu Phe Ile Asn Glu Arg Gly Val Leu Ala Ser Gly Arg
1               5                   10                  15

Pro Cys Glu Pro Gly Cys Arg Thr Phe Phe Arg Val Cys Leu Lys His
            20                  25                  30

Phe Gln Ala Val Val Ser Pro Gly Pro Cys Thr Phe Gly Thr Val Ser
        35                  40                  45

Thr Pro Val Leu Gly Thr Asn Ser Phe Ala Val Arg Asp Asp Ser Ser
    50                  55                  60

Gly Gly Gly Arg Asn Pro Leu Gln Leu Pro Phe Asn Phe Thr Trp Pro
65                  70                  75                  80

Gly Thr Phe Ser Leu Ile Ile Glu Ala Trp His Ala Pro Gly Asp Asp
                85                  90                  95

Leu Arg Pro Glu Ala Leu Pro Pro Asp Ala Leu Ile Ser Lys Ile Ala
            100                 105                 110
```

-continued

```
Ile Gln Gly Ser Leu Ala Val Gly Gln Asn Trp Leu Leu Asp Glu Gln
            115                 120                 125

Thr Ser Thr Leu Thr Arg Leu Arg Tyr Ser Tyr Arg Val Ile Cys Ser
    130                 135                 140

Asp Asn Tyr Tyr Gly Asp Asn Cys Ser Arg Leu Cys Lys Lys Arg Asn
145                 150                 155                 160

Asp His Phe Gly His Tyr Val Cys Gln Pro Asp Gly Asn Leu Ser Cys
                165                 170                 175

Leu Pro Gly Trp Thr Gly Glu Tyr Cys Gln Gln Pro Ile Cys Leu Ser
            180                 185                 190

Gly Cys His Glu Gln Asn Gly Tyr Cys Ser Lys Pro Ala Glu Cys Leu
        195                 200                 205

Cys Arg Pro Gly Trp Gln Gly Arg Leu Cys Asn Glu Cys Ile Pro His
    210                 215                 220

Asn Gly Cys Arg His Gly Thr Cys Ser Thr Pro Trp Gln Cys Thr Cys
225                 230                 235                 240

Asp Glu Gly Trp Gly Gly Leu Phe Cys Asp Gln Asp Leu Asn Tyr Cys
                245                 250                 255

Thr His His Ser Pro Cys Lys Asn Gly Ala Thr Cys Ser Asn Ser Gly
            260                 265                 270

Gln Arg Ser Tyr Thr Cys Thr Cys Arg Pro Gly Tyr Thr Gly Val Asp
        275                 280                 285

Cys Glu Leu Glu Leu Ser Glu Cys Asp Ser Asn Pro Cys Arg Asn Gly
    290                 295                 300

Gly Ser Cys Lys Asp Gln Glu Asp Gly Tyr His Cys Leu Cys Pro Pro
305                 310                 315                 320

Gly Tyr Tyr Gly Leu His Cys Glu His Ser Thr Leu Ser Cys Ala Asp
                325                 330                 335

Ser Pro Cys Phe Asn Gly Gly Ser Cys Arg Glu Arg Asn Gln Gly Ala
            340                 345                 350

Asn Tyr Ala Cys Glu Cys Pro Pro Asn Phe Thr Gly Ser Asn Cys Glu
        355                 360                 365

Lys Lys Val Asp Arg Cys Thr Ser Asn Pro Cys Ala Asn Gly Gly Gln
    370                 375                 380

Cys Leu Asn Arg Gly Pro Ser Arg Met Cys Arg Cys Arg Pro Gly Phe
385                 390                 395                 400

Thr Gly Thr Tyr Cys Glu Leu His Val Ser Asp Cys Ala Arg Asn Pro
                405                 410                 415

Cys Ala His Gly Gly Thr Cys His Asp Leu Glu Asn Gly Leu Met Cys
            420                 425                 430

Thr Cys Pro Ala Gly Phe Ser Gly Arg Arg Cys Glu Val Arg Thr Ser
        435                 440                 445

Ile Asp Ala Cys Ala Ser Ser Pro Cys Phe Asn Arg Ala Thr Cys Tyr
    450                 455                 460

Thr Asp Leu Ser Thr Asp Thr Phe Val Cys Asn Cys Pro Tyr Gly Phe
465                 470                 475                 480

Val Gly Ser Arg Cys Glu Phe Pro Val Gly Leu Pro Pro Ser Phe Pro
                485                 490                 495

Trp Val Ala Val Ser Leu Gly Val Gly Leu Ala Val Leu Leu Val Leu
            500                 505                 510

Leu Gly Met Val Ala Val Ala Val Arg Gln Leu Arg Leu Arg Arg Pro
        515                 520                 525
```

```
Asp Asp Gly Ser Arg Glu Ala Met Asn Asn Leu Ser Asp Phe Gln Lys
        530                 535                 540

Asp Asn Leu Ile Pro Ala Ala Gln Leu Lys Asn Thr Asn Gln Lys Lys
545                 550                 555                 560

Glu Leu Glu Val Asp Cys Gly Leu Asp Lys Ser Asn Cys Gly Lys Gln
                565                 570                 575

Gln Asn His Thr Leu Asp Tyr Asn Leu Ala Pro Gly Pro Leu Gly Arg
            580                 585                 590

Gly Thr Met Pro Gly Lys Phe Pro His Ser Asp Lys Ser Leu Gly Glu
        595                 600                 605

Lys Ala Pro Leu Arg Leu His Ser Glu Lys Pro Glu Cys Arg Ile Ser
    610                 615                 620

Ala Ile Cys Ser Pro Arg Asp Ser Met Tyr Gln Ser Val Cys Leu Ile
625                 630                 635                 640

Ser Glu Glu Arg Asn Glu Cys Val Ile Ala Thr Glu Val
                645                 650

<210> SEQ ID NO 24
<211> LENGTH: 18
<212> TYPE: DNA
<213> ORGANISM: Mus musculus

<400> SEQUENCE: 24
acaccccaag ggatgacg                                                   18

<210> SEQ ID NO 25
<211> LENGTH: 18
<212> TYPE: DNA
<213> ORGANISM: Mus musculus

<400> SEQUENCE: 25
cctctgtggc aatcacac                                                   18

<210> SEQ ID NO 26
<211> LENGTH: 60
<212> TYPE: DNA
<213> ORGANISM: Mus musculus

<400> SEQUENCE: 26
tctgaattct taggacttgt catcgtcgtc cttgtagtca gctacctctg tggcaatcac    60

<210> SEQ ID NO 27
<211> LENGTH: 24
<212> TYPE: DNA
<213> ORGANISM: Mus musculus

<400> SEQUENCE: 27
atggaagggt tttccctcac cgcc                                            24

<210> SEQ ID NO 28
<211> LENGTH: 24
<212> TYPE: DNA
<213> ORGANISM: Mus musculus

<400> SEQUENCE: 28
gtccacgctc tgcagctctg tgaa                                            24

<210> SEQ ID NO 29
<211> LENGTH: 21
<212> TYPE: DNA
<213> ORGANISM: Mus musculus
```

```
<400> SEQUENCE: 29
cgcactgacc acgagcttca c                                          21

<210> SEQ ID NO 30
<211> LENGTH: 22
<212> TYPE: DNA
<213> ORGANISM: Mus musculus

<400> SEQUENCE: 30
tccagggaca gcacctcatc tg                                         22

<210> SEQ ID NO 31
<211> LENGTH: 20
<212> TYPE: DNA
<213> ORGANISM: Mus musculus

<400> SEQUENCE: 31
agcaactgga cgcatgtatc                                            20

<210> SEQ ID NO 32
<211> LENGTH: 20
<212> TYPE: DNA
<213> ORGANISM: Mus musculus

<400> SEQUENCE: 32
tcaccatctc tgtagtcagg                                            20

<210> SEQ ID NO 33
<211> LENGTH: 22
<212> TYPE: DNA
<213> ORGANISM: Mus musculus

<400> SEQUENCE: 33
tgcagacatt ctagcactct gg                                         22

<210> SEQ ID NO 34
<211> LENGTH: 20
<212> TYPE: DNA
<213> ORGANISM: Mus musculus

<400> SEQUENCE: 34
acatctgcct tcacgtcgat                                            20

<210> SEQ ID NO 35
<211> LENGTH: 22
<212> TYPE: DNA
<213> ORGANISM: Mus musculus

<400> SEQUENCE: 35
ttccatctaa gccccagttt tg                                         22

<210> SEQ ID NO 36
<211> LENGTH: 21
<212> TYPE: DNA
<213> ORGANISM: Mus musculus

<400> SEQUENCE: 36
ccccatctac cttccagtcc a                                          21

<210> SEQ ID NO 37
<211> LENGTH: 18
<212> TYPE: DNA
<213> ORGANISM: Mus musculus
```

```
<400> SEQUENCE: 37 gccaggggt ctagaagc                                              18

<210> SEQ ID NO 38
<211> LENGTH: 20
<212> TYPE: DNA
<213> ORGANISM: Mus musculus

<400> SEQUENCE: 38
tcacttggca cccagtacaa                                           20

<210> SEQ ID NO 39
<211> LENGTH: 15
<212> TYPE: DNA
<213> ORGANISM: Mus musculus

<400> SEQUENCE: 39
atggccaaga gctgc                                                15

<210> SEQ ID NO 40
<211> LENGTH: 17
<212> TYPE: DNA
<213> ORGANISM: Mus musculus

<400> SEQUENCE: 40
agaatacagg tcccgct                                              17

<210> SEQ ID NO 41
<211> LENGTH: 21
<212> TYPE: DNA
<213> ORGANISM: Mus musculus

<400> SEQUENCE: 41
cagagcctcc tcccccaaca g                                         21

<210> SEQ ID NO 42
<211> LENGTH: 21
<212> TYPE: DNA
<213> ORGANISM: Mus musculus

<400> SEQUENCE: 42
gctcagaggg gtgggtaaga t                                         21

<210> SEQ ID NO 43
<211> LENGTH: 20
<212> TYPE: DNA
<213> ORGANISM: Mus musculus

<400> SEQUENCE: 43
tagtcgatca gcttcgatgg                                           20

<210> SEQ ID NO 44
<211> LENGTH: 20
<212> TYPE: DNA
<213> ORGANISM: Mus musculus

<400> SEQUENCE: 44
gctctctggc attgttagcc                                           20

<210> SEQ ID NO 45
<211> LENGTH: 21
<212> TYPE: DNA
<213> ORGANISM: Mus musculus
```

-continued

```
<400> SEQUENCE: 45
gccagtgtca acacgacacc g                                              21

<210> SEQ ID NO 46
<211> LENGTH: 20
<212> TYPE: DNA
<213> ORGANISM: Mus musculus

<400> SEQUENCE: 46
tcacctcgtt catgcactcg                                                20

<210> SEQ ID NO 47
<211> LENGTH: 22
<212> TYPE: DNA
<213> ORGANISM: Mus musculus

<400> SEQUENCE: 47
atccgcccta tgtgcccgag ta                                             22

<210> SEQ ID NO 48
<211> LENGTH: 22
<212> TYPE: DNA
<213> ORGANISM: Mus musculus

<400> SEQUENCE: 48
atgtggctgg agtggctgaa gg                                             22

<210> SEQ ID NO 49
<211> LENGTH: 21
<212> TYPE: DNA
<213> ORGANISM: Mus musculus

<400> SEQUENCE: 49
gtgggccgct ctaggcacca a                                              21

<210> SEQ ID NO 50
<211> LENGTH: 24
<212> TYPE: DNA
<213> ORGANISM: Mus musculus

<400> SEQUENCE: 50
ctctttgatg tcacgcacga tttc                                           24
```

CELL PREPARATIONS COMPRISING CELLS OF THE T CELL LINEAGE AND METHODS OF MAKING AND USING THEM

This application claims the benefit under 35 USC § 119(e) from U.S. Provisional patent application Ser. No. 60/432,525 filed Dec. 10, 2002, which is incorporated herein by reference in its entirety.

FIELD OF THE INVENTION

The invention relates to cell preparations comprising cells of the T cell lineage, methods for preparing same, and uses of the cell preparations.

BACKGROUND OF THE INVENTION

The development of the various hematopoietic cell lineages is compartmentalized during fetal development and throughout adult life. At approximately day 12 of embryonic development, the fetal liver (FL) is seeded by definitive hematopoietic stem cells, which arise from the aorta-gonad-mesonephros region of the developing embryo (Cumano and Godin, 2001). The FL continues as the primary site of hematopoietic development until birth, when the bone marrow (BM) takes over as the primary site for hematopoiesis in the adult.

The process of stem cell differentiation is tightly regulated by soluble factors and cell contact-dependent signals within specialized microenvironments, each of which support the development of specific cell lineages. During lymphopoiesis, the thymic environment is required for the differentiation of hematopoietic progenitor cells (HPCs) into T lymphocytes (Anderson et al., 1996). On the other hand, B cell development takes place within the BM microenvironment (Osmond, 1994). The process of hematopoiesis can be modeled in vitro using BM-derived stromal cell lines (Dorshkind, 1990). A number of BM derived stromal cell lines have been developed in recent years, which are capable of supporting the development of multiple hematopoietic cell lineages. For instance, the OP9 BM stromal cell line (Kodama et al., 1994) has been shown to support the differentiation of HPCs into multiple lineages, including B cells, in vitro (Carlyle et al., 1997). However, efforts to generate T cells from HPCs in vitro in the absence of a thymic microenvironment have been unsuccessful. This is thought to be due to unknown factors acting at multiple developmental stages within the three-dimensional architecture of the thymus (Anderson et al., 1996; Lind et al., 2001).

The process of T cell development from HPC to mature TCR-$\alpha\beta^+$ T cell consists of a series of commitment events and multiple developmental checkpoints, including TCR V(D)J gene rearrangement, TCR-$\beta$-selection, and positive/negative selection of developing thymocytes. Efforts to recapitulate one or more of these events in vitro have had to depend on the use of fetal thymic organ culture (Anderson et al., 1996). The molecular interactions responsible for this thymus dependency remain largely unknown. However, a number of recent studies have implicated Notch receptor-ligand interactions in the earliest T cell lineage commitment events (MacDonald et al., 2001). Notch signaling is an evolutionarily conserved pathway that controls multiple cell fate decisions throughout ontogeny. Notch signaling is initiated by the local interaction of Notch receptors with Notch ligands on neighboring cells (Artavanis-Tsakonas et al., 1999). In vertebrates, these ligands consist of Jagged and Delta-like family members. Engagement of the Notch receptor results in its proteolytic cleavage by a presenilin dependant $\gamma$-secretase activity (Taniguchi et al., 2002), followed by the translocation of the cleaved intracellular domain of Notch to the nucleus, where it binds to CBF-1/RBP-J$\kappa$ and activates transcription of downstream target genes (Artavanis-Tsakonas et al., 1999).

Several lines of evidence implicate Notch signaling at various stages of lymphocyte development. Specifically, it has been suggested that Notch signaling promotes TCR-$\alpha\beta^+$ T cell development at the expense of TCR-$\gamma\delta^+$ T cell development (Washburn et al., 1997). Furthermore, a number of investigators have proposed various roles for Notch in the development of CD4$^+$ and CD8$^+$ single positive (SP) T cells from CD4$^+$ CD8$^+$ (DP) precursor thymocytes (Deftos et al., 2000; Izon et al., 2001; Robey et al., 1996; Wolfer et al., 2001). There is also data from studies that address the role of Notch signaling in governing T cell versus B cell fate decisions by lymphocyte progenitors. Specifically, B cell development is abolished in mice reconstituted with BM progenitors expressing a constitutively active form of Notch, rather DP T cells develop in the BM of these mice (Pui et al., 1999). In a complementary experiment, Notch-1 conditionally-deficient mice show a severe block in T cell development, with the concomitant development of B cells in the thymus (Radtke et al., 1999). These results strongly support the notion that Notch signaling is critical for the earliest stages of T cell commitment. A further role of Notch signals at early stages of T cell development has recently begun to be elucidated. Radtke and colleagues demonstrated that a conditional inactivation Notch-1 at the CD44$^+$ CD25$^+$ (DN2) stage of T cell development results in a partial block at the subsequent CD44$^-$ CD25$^+$ (DN3) stage (Wolfer et al., 2002). This was shown to be the result of inefficient V to DJ recombination at the TCR-$\beta$ locus. In contrast, rearrangements at the TCR-$\gamma\delta$ locus were not affected.

The citation of any reference herein is not an admission that such reference is available as prior art to the instant invention.

SUMMARY OF THE INVENTION

Applicants produced an in vitro system that supports T cell lymphopoiesis but does not support B cell lymphopoiesis. Applicants have found that ectopic expression of an appropriate Notch ligand by a stromal cell line induces hematopoietic progenitor cells or stem cells to adopt a T cell fate.

In particular, Applicants generated an in vitro system for the induction of T cell lineage commitment by fetal liver-derived hematopoietic stem cells. OP9 BM stromal cells were retrovirally-transduced to express the Notch ligand Delta-like-1, and the resulting Delta-like-1-expressing OP9 cell line (OP9-DL1) lost the ability to support B cell lymphopoiesis, while gaining the capacity to induce a normal program of T cell differentiation from fetal liver-derived hematopoietic progenitor cells, including the generation of double positive and single positive T cells. Strikingly, hematopoietic progenitor cells induced to differentiate on OP9-DL1 cells underwent robust cellular expansion and gave rise to both $\alpha\beta$-TCR+ and $\gamma\delta$-TCR+ T cells. Moreover, CD8 single positive TCR$^{hi}$ cells produced $\gamma$-interferon following CD3/TCR stimulation, demonstrating that functionally mature T cells were generated. Thus, expression of Delta-like-1 on OP9 BM stromal cells provides the necessary signals for the induction of T cell lineage commitment, TCR V(D)J rearrangement, and T cell differentiation by hematopoietic progenitor cells in the absence of a thymus. Applicants system also induced T cell lineage commitment and differentiation by embryonic stem cells.

Broadly stated the invention provides an in vitro system that supports T cell lymphopoiesis but does not support B cell lymphopoiesis. The system comprises a Notch ligand that induces T cell lineage commitment and differentiation, and additionally may induce stage-specific progenitor expansion, TCR gene rearrangement, and T cell differentiation by hematopoietic progenitors and embryonic stem cells in the absence of thymus.

In an aspect, the system comprises a cell preparation that induces T cell commitment and differentiation in the absence of thymus. The cell preparation additionally may induce TCR V(D)J rearrangement, and T cell differentiation by hematopoietic progenitor cells or embryonic stem cells. In a particular embodiment, the cell preparation comprises cells that express a Notch ligand (i.e. a Notch Ligand Cell Preparation).

In another aspect the invention contemplates a composition which comprises a nutrient medium that has been conditioned by exposure to a cell preparation of the invention and secretes a Notch ligand.

In still another aspect the invention relates to methods of inducing cells capable of differentiating into cells of the T cell lineage to form cells of the T cell lineage. In accordance with the present invention, the method comprises obtaining cells that are capable of differentiating into cells of the T cell lineage, culturing the cells with an in vitro system of the invention so that the cells differentiate to form cells of the T cell lineage.

This novel process leads to the generation of cells of the T cell lineage.

In another aspect the invention relates to newly created T cell lineage compositions generated with a system of the invention comprising cells of the T cell lineage (herein sometimes referred to as "T cell lineage compositions").In an embodiment, the T cell lineage composition comprises substantially cells of the T cell lineage. In an embodiment, at least 50%, 75%, 90%, or 95% of the cells of the composition are cells of the T cell lineage. In another embodiment, the cells of the T cell lineage are preserved using cryogenic methods.

In a particular aspect of the invention a cellular composition is provided which is produced by culturing cells capable of differentiating into cells of the T cell lineage with a system of the invention, and isolating cells of the T cell lineage in the culture.

T cell lineage compositions generated with a system of the invention may comprise immature T cells with the potential or increased potential to form mature T cells. Thus, the invention contemplates methods for inducing immature T cells in T cell lineage compositions to differentiate into mature T cells in vitro or in vivo. The invention also contemplates a cellular composition comprising mature T cells produced by these methods.

The T cell lineage compositions generated with a system of the invention may be used in a variety of methods (e.g. transplantation) and they have numerous uses in the field of medicine. In an aspect of the invention, newly created cellular compositions comprising cells of the T cell lineage or cells differentiated therefrom, can be used in both cell therapies and gene therapies aimed at alleviating disorders and diseases involving cells of the T cell lineage.

The invention also provides a method of treating a patient with a condition involving cells of the T cell lineage, in particular a defect in such cells, comprising transferring a cellular composition comprising cells of the T cell lineage or cells differentiated therefrom into the patient.

In an aspect, the invention features a kit including cells of the T cell lineage generated using a method or system of the invention, or a mitotic or differentiated cell that is the progeny of the cells.

Still another aspect of the invention is a kit for producing T cell lineage compositions comprising cells of the T cell lineage. A kit can include media components that allow for the induction of T cell lymphopoiesis. Preferably, a kit also includes instructions for its use.

The cellular compositions generated with a system of the invention may be used to screen for potential therapeutics that modulate development or activity of cells of the T cell lineage, in particular mature T cells.

The cellular compositions generated with a system of the invention may be used to prepare model systems of disease, and they can also be used to produce growth factors, hormones, etc.

The present invention also provides a method for expanding cells of the T cell lineage. The method comprises (a) culturing cells capable of differentiating into cells of the T cell lineage with a system of the invention; and (b) isolating increased numbers of cells of the T cell lineage. "Increased numbers of cells of the T cell lineage", refers to an increase in the number of cells by at least about 10-15-fold. The invention also relates to an expanded cellular composition comprising cells of the T cell lineage obtained by this method.

In an aspect, the invention provides a method for in vivo expansion of cells of the T cell lineage in a subject by modulating the differentiation of hematopoietic progenitor cells by altering the endogenous activity of a Notch ligand by administering a substance that increases the production of the Notch ligand in a subject.

In another aspect the invention provides a method for ex vivo expansion of cells of the T cell lineage and administration of the cells to a subject. This aspect of the invention is performed by first isolating a population containing hematopoietic progenitor cells from the subject. Next, the differentiation and expansion of the cells to cells of the T cell lineage is modulated using a system or method of the invention that introduces or increases the amount of Notch ligand into the culture. Finally, the cells of the T cell lineage are administered to the subject.

The invention also contemplates a pharmaceutical composition comprising cells of the T cell lineage generated with a system of the invention and a pharmaceutically acceptable carrier, excipient, or diluent.

The invention also relates to a method for conducting a regenerative medicine business, comprising: (a) a service for accepting and logging in samples from a client comprising cells capable of differentiating into cells of the T cell lineage; (b) a system for culturing cells dissociated from the samples, which system provides conditions for inducing formation of cells of the T cell lineage; (c) a cell preservation system for preserving cells of the T cell lineage generated by the system in (b) for later retrieval on behalf of the client or a third party. The method may further comprise a billing system for billing the client or a medical insurance provider thereof.

The invention features a method for conducting a stem cell business comprising identifying agents which influence the proliferation, differentiation, or survival of cells of the cellular compositions of the invention. Examples of such agents are small molecules and extracellular proteins. An agent may be a modulator of Notch ligands such as members of the Fringe family (R. J. Fleming et al, Development 124, 2973, 1997; V. M. Panin et al, Nature 387, 908 (1997). Identified agents can be profiled and assessed for safety and efficacy in animals. In another aspect, the invention contemplates methods for influencing the proliferation, differentiation, or survival of cells of the cellular compositions of the invention by contacting the cells with an agent or agents identified by the foregoing method. The identified agents can be formulated as a pharmaceutical preparation, and manufactured, marketed, and distributed for sale.

In an embodiment, the invention provides a method for conducting a stem cell business comprising (a) identifying one or more agents which affect the proliferation, differentiation, function, or survival of cells of T cell lineage compositions of the invention; (b) conducting therapeutic profiling of agents identified in (a); or analogs thereof for efficacy and toxicity in animals; and (c) formulating a pharmaceutical composition including one or more agents identified in (b) as having an acceptable therapeutic profile. The method may further comprise the step of establishing a distribution system for distributing the pharmaceutical preparation for sale. The method may also comprise establishing a sales group for marketing the pharmaceutical preparation.

The invention also contemplates a method for conducting a drug discovery business comprising identifying factors which influence the proliferation, differentiation, or survival of cells of the cellular compositions of the invention, and licensing the rights for further development.

DESCRIPTION OF THE DRAWINGS

The invention will now be described in relation to the drawings in which.

BRIEF DESCRIPTION OF THE SEQUENCES

Figure 1:
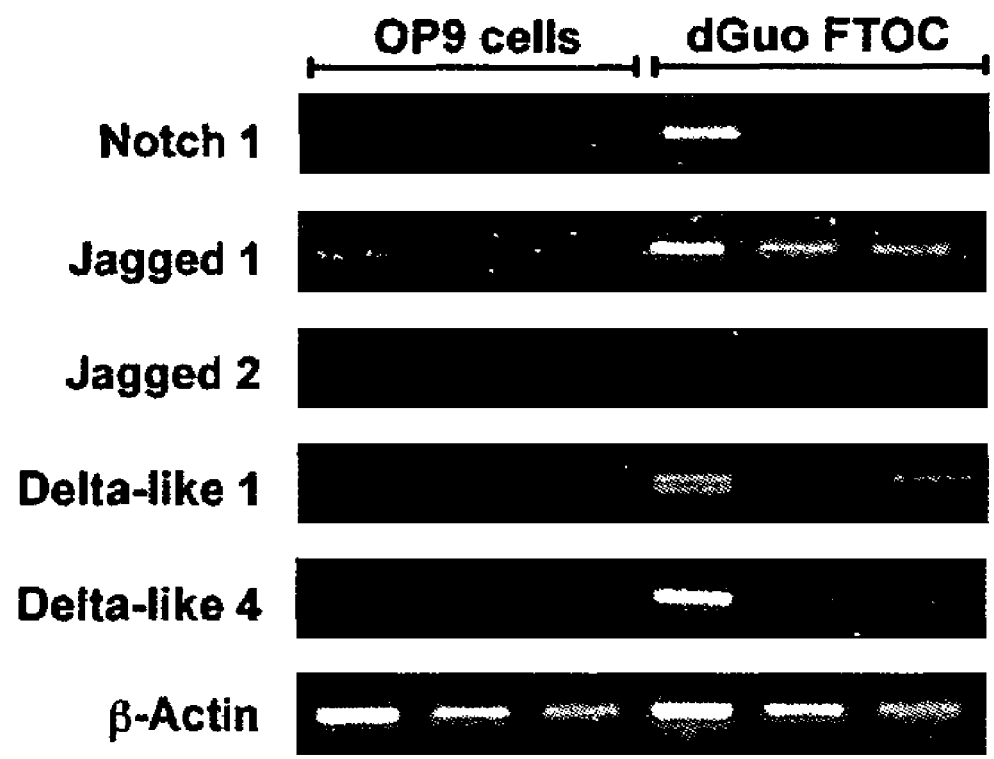
FIG. 1. Analysis of Notch ligand expression by OP9 cells. RT-PCR was performed for the indicated transcripts from OP9 cells and thymic stroma-enriched d14 fetal thymic lobes. Three serial dilutions (3-fold) of template cDNA are shown for each primer pair.

SEQ ID NO. 1 is an amino acid sequence of *homo sapiens*-Delta-1.
SEQ ID NO. 2 is a amino acid sequence of *rattus norvegicus*Delta-3.
SEQ ID NO. 3 is an amino acid sequence of *homo sapiens*-Delta-like-1.
SEQ ID NO. 4 is an amino acid sequence of *mus musculus*-Delta-like-1.
SEQ ID NO. 5 is an amino acid sequence of *rattus norvegicus*Delta-like-3.
SEQ ID NO. 6 is an amino acid sequence of *homo sapiens*-Delta-like 4.
SEQ ID NO. 7 is an amino acid sequence of *mus musculus*-Delta-like 4.
SEQ ID NO. 8 is a nucleic acid sequence of *homo sapiens*-Delta-like-1.
SEQ ID NO. 9 is a nucleic acid sequence of *mus musculus*-Delta-like-1.
SEQ ID NO. 10 is a nucleic acid sequence of *homo sapiens*-Delta-like-4.
SEQ ID NO. 11 is a nucleic acid sequence of *mus musculus*-Delta-like-4.
SEQ ID NO. 12 is a PCR primer for Notch-1 upper.
SEQ ID NO. 13 is a PCR primer for Notch-1 lower.
SEQ ID NO. 14 is a PCR primer for Jagged-1 upper.
SEQ ID NO. 15 is a PCR primer for Jagged-1 lower.
SEQ ID NO. 16 is a PCR primer for Jagged-2 upper.
SEQ ID NO. 17 is a PCR primer for Jagged-2 lower.
SEQ ID NO. 18 is a PCR primer for Delta-like-1 upper.
SEQ ID NO. 19 is a PCR primer for Delta-like-1 lower.
SEQ ID NO. 20 is a PCR primer for Delta-like-4 upper.
SEQ ID NO. 21 is a PCR primer for Delta-like-4 lower.
SEQ ID NO. 22 is an amino acid sequence for *mus musculus*Delta 4.
SEQ ID NO. 23 is an amino acid sequence for *homo sapiens*-Delta 4.
SEQ ID NOS. 24-26 are primers used to clone Dl14.
SEQ ID NOS. 27-50 are the primers listed in Table 1.

DETAILED DESCRIPTION OF THE INVENTION

In accordance with the present invention there may be employed conventional molecular biology, microbiology, and recombinant DNA techniques within the skill of the art. Such techniques are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984).

Glossary

For convenience, certain terms employed in the specification and claims are collected here.

A "Notch ligand" is capable of binding to a Notch receptor polypeptide present in the membrane of a number of different mammalian cells such as hematopoietic stem cells. The Notch receptors that have been identified in human cells include Notch-1, Notch-2, Notch-3, and Notch-4. Notch ligands typically have a diagnostic DSL domain (D-Delta, S-Serrate, and L-Lag2) comprising 20 to 22 amino acids at the amino terminus and between 3 to 8 EGF-like repeats (Furie and Furie, 1988, Cell 53: 505-518; Knust et al, 1987 EMBO J. 761-766; Suzuki et al, 1987, EMBO J. 6:1891-1897) on the extracellular surface.

A Notch ligand is selected that promotes and maintains differentiation and proliferation of cells of the T cell lineage. A Notch ligand may be human in origin, or may be derived from other species, including mammalian species such as rodent, dog, cat, pig, sheep, cow, goat, and primates. Particular examples of Notch Ligands include the Delta family. The Delta family includes Delta-1 (Genbank Accession No. AF003522, Homo sapiens, SEQ ID NO. 1), Delta-3 (Genbank Accession No. AF084576, Rattus norvegicus, SEQ ID NO. 2), Delta-like 1 (Genbank Accession No. NM_005618 and NP_005609, Homo sapiens, SEQ ID NO. 3; Genbank Accession No. X80903, I48324, M. musculus SEQ ID NO. 4), Delta-like 3 (Genbank Accession No. NM_053666, N_446118, Rattus norvegicus, SEQ ID NO. 5), Delta-4 (Genbank Accession No. AF273454, BAB18580, Mus musculus, SEQ ID NO. 22, Genbank Accession No. AF279305, AAF81912, Homo sapiens, SEQ ID NO. 23), and Delta-like 4 (Genbank Accession. No. Q9NR61, AAF76427, AF253468, NM_019074, Homo sapiens, SEQ ID NO.6. Genbank Accession No. NM_019454, mus musculus, SEQ ID NO.7). Notch ligands are commercially available or can be produced by recombinant DNA techniques and purified to various degrees.

The term "Notch ligand" includes homologues of the known Notch ligands that may be identified by standard techniques. "Homologue" refers to a gene product that exhibits sequence homology, either amino acid or nucleic acid sequence homology, to any one of the known Notch ligands. A Notch ligand may be at least 20%, 30%, 40%, 50%, 60%, 70%, 80%, preferably 90%, more preferably 95%, most preferably 98-99% identical at the amino acid level to a corresponding Notch ligand.

Techniques and software for determining sequence homology or identity between two or more amino acid or nucleic acid sequences are well known in the art. [See Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48. 1073 (1988); and publicly available computer program methods such as the GCG program package (Devereux, J., et al., Nucleic Acids Research 12(1). 387 (1984)), BLASTP, BLASTN, and FASTA (Atschul, S. F. et al., J. Molec. Biol 215:403-410 (1990).]

Notch ligand homologues can be identified by techniques known in the art such as probing genomic or DNA libraries with probes comprising all or part of a nucleic acid encoding a Notch ligand (reference) under conditions of medium to high stringency (e.g. 0.03M sodium chloride, 0.03M sodium citrate at from about 50° C.-60° C.). Homologues can also be identified using degenerate PCR that will typically use primers designed to target sequences within the variants and homologues encoding conserved amino acid sequences. Primers may contain one or more degenerate positions and can be used at stringency conditions lower than those used for cloning with single sequence primers against known sequences.(eg. PCR using a lower annealing temperature and/or higher concentrations of $Mg^{++}$)

It is preferred that homologues of Notch ligands also comprise a DSL domain at the N-terminus and have between 3 to 8 EGF-like repeats on the extracellular surface. Suitable homologues will also be capable of binding to a Notch receptor. Binding to a Notch receptor may be determined by a variety of methods known in the art including in vitro binding assays.

A "Notch ligand" also includes a mutant or variant of a known Notch ligand. The term "mutant" refers to a polypeptide having a primary amino acid sequence which differs from the wild type sequence by one or more amino acid additions, substitutions or deletions. Preferably, the mutant has at least 90% sequence identity with the wild type sequence. Preferably, the mutant has 20 mutations or less over the whole wild-type sequence. More preferably the mutant has 10 mutations or less, most preferably 5 mutations or less over the whole wild-type sequence.

The term "variant" refers to a naturally occurring polypeptide which differs from a wild-type sequence. A variant may be found within the same species (i.e. if there is more than one isoform of the enzyme) or may be found within a different species. Preferably the variant has at least 90% sequence identity with the wild type sequence. Preferably, the variant has 20 mutations or less over the whole wild-type sequence. More preferably, the variant has 10 mutations or less, most preferably 5 mutations or less over the whole wild-type sequence.

A "Notch Ligand Cell Preparation" refers to a cell preparation that supports or induces T cell lineage commitment and differentiation, but does not support or induce B cell differentiation. A Notch Ligand Cell Preparation can also be characterized by the following:
 (a) cells in the preparation express a Notch ligand; and
 (b) cells in the preparation are preferably stromal cells.

In an embodiment, a Notch Ligand Cell Preparation has substantially reduced or lacks factors that are responsible for preferential differentiation of cells into the monocyte-macrophage lineage, including factors such as macrophage colony-stimulating factor (M-CSF). The cells in the preparation can be derived from cells that do not express M-CSF, the cells can be modified so that M-CSF is reduced or eliminated, or the cells can be treated with substances that removes M-CSF e.g. antibodies that recognized M-CSF.

Suitable Notch Ligand Cell Preparations include but are not limited to stromal cell lines expressing a Notch ligand of the Delta family. Examples of stromal cell lines that can be engineered to express a Notch ligand of the Delta family are the mouse stromal cell lines MS5 (Itoh, K. et al, Exp Hematol 1989 Feb 17(2):145-53) and S 17, and the human stromal cell lines HGS2.11, HGS2.52, HGS.18, HGS3.30, HGS3.65, HGS3.66 HGS3.103, and HGS3.114 available from Human Genome Sciences Inc (MD) (See US Published Application 20020001826).

In an embodiment, a Notch Ligand Cell Preparation comprises stromal cells obtained from mammals that lack functional M-CSF (e.g. as a result of a mutation in the M-CSF gene), that have been modified to express high levels of Notch Ligands of the Delta family. In a particular embodiment, a Notch Ligand Cell Preparation comprises OP9 cells (Kodama et al, 1994; Nakano et al, 1994; available from the RIKEN cell depository that express Delta-like-1 or Delta-like-4. Specifically, a Notch Ligand Cell Preparation may comprise OP9 cells expressing Delta-like-1.

A Notch Ligand Cell Preparation may be prepared by standard techniques. By way of example, a preparation comprising OP9 cells expressing Notch ligands of the Delta family may be prepared by introducing a polynucleotide encoding a Notch Ligand into OP9 cells. In particular, a polynucleotide encoding a Notch ligand having the sequences of SEQ ID NO. 8 or 9 (Delta-like-1), or SEQ ID NO. 10 or 11 (Delta-like-4) may be introduced into OP9 cells.

A polynucleotide encoding a Notch ligand may be introduced into cells via conventional techniques such as calcium phosphate or calcium chloride co-precipitation, DEAE-dextran-mediated transfection, lipofection, electroporation, or microinjection. Suitable methods for transforming and transfecting cells can be found in Sambrook et al. (Molecular Cloning: A Laboratory Manual, 2nd Edition, Cold Spring Harbor Laboratory press (1989)), and other laboratory textbooks. By way of example, a polynucleotide encoding a Notch ligand may be introduced into cells using an appropriate expression vector including but not limited to cosmids, plasmids, or modified viruses (e.g. replication defective retroviruses, adenoviruses and adeno-associated viruses). Transfection is easily and efficiently obtained using standard methods including culturing the cells on a monolayer of virus-producing cells (Van der Putten, Proc Natl Acad Sci U S A. 1985 September ;82(18):6148-52; Stewart et al. (1987) EMBO J. 6:383-388). An expression vector typically contains appropriate regulatory sequences, and it may also contain genes that encode a fusion moiety which provides increased expression of a Notch ligand or increased solubility of a Notch ligand.

A gene encoding a selectable marker may be integrated into the cells. For example, a gene which encodes a protein such as β-galactosidase, chloramphenicol acetyltransferase, firefly luciferase, or a fluorescent protein marker may be integrated into the cells. Examples of fluorescent protein markers are the Green Fluorescent Protein (GFP) from the jellyfish *A. victoria*, or a variant thereof. (For example, the GFP variants of Heim et al, Proc. Natl. Acad. Sci. 91:12501, 1994; M. Zernicka-Goetz et al, Development 124:1133-1137, 1997; Okabe, M. et al, FEBS Letters 407:313-319, 1997; Clontech Palo Alto, Calif.; and EGFP commercially available from Clontech.)

In an embodiment, a vector expressing a GFP is employed. Examples of such vectors include but are not limited to MigR1, MIEV, and LXSN. Vectors expressing a GFP are commercially available, and in particular can be obtained from Clontech. In a particular embodiment, a vector that expresses GFP and Delta-like-1 or Delta-like-4 is employed.

"Cells capable of differentiation into cells of the T cell lineage" refers to hematopoietic progenitor and stem cells and embryonic stem cells that differentiate into cells of the T cell lineage when cultured with a Notch ligand, in particular with a system of the invention, preferably with a "Notch Ligand Cell Preparation". Cells capable of differentiation into cells of the T cell lineage may be genetically modified (transduced or transfected) either in nature or by genetic engineering techniques in vivo or in vitro (see discussion herein of transduction and transfection techniques).

"Hematopoietic progenitor cells" are cells that are derived from hematopoietic stem cells or fetal tissue, that are capable of further differentiation to more mature cell types (i.e. cells of the T cell lineage). Hematopoietic progenitor cells that are $CD24^{lo}Lin^- CD117^+$ are preferably used in the methods and systems of the invention.

"Hematopoietic stem cells" refers to undifferentiated hematopoietic cells that are capable of essentially unlimited propagation either in vivo or ex vivo and capable of differentiation to other cell types, including cells of the T cell lineage.

"Embryonic Stem Cells" or "ES cells" refers to undifferentiated embryonic stem cells that have the ability to integrate into and become part of the germ line of a developing embryo. Embryonic stem cells that are suitable for use herein include cells from the J1 ES cell line, 129J ES cell line, murine stem cell line D3 (American Type Culture Collection catalog no. CRL 1934), the R1 or E14K cell lines derived from 129/Sv mice, cell lines derived from Balb/c and C57B1/6 mice, and human embryonic stem cells (e.g. from WiCell Research Institute, WI; or ES cell International, Melbourne, Australia).

The cells can be cultured using methods well known to the skilled artisan, such as those set forth by Robertson (in Teratocarcinomas and Embryonic Stem Cells: A Practical Approach, E. J. Robertson, ed. IRL Press, Washington, D.C. [1987]) and by Bradley et al (Current Topics in Devel. Biol. 20:357-371 [1986], and by Hogan et al (Manipulating the Mouse Embryo: A Laboratory Manual, Cold Spring Harbor Laboratory Press, Cold Spring Harbor, N.Y. [1986]).

"Cells of the T cell lineage" refers to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g. $CD8^+$), or a physiological, morphological, functional, or immunological feature specific for a T cell. Cells of the T cell lineage may be (a) progenitor or precursor cells committed to the T cell lineage; (b) $CD25^+$ immature and inactivated T cells; (c) cells that have undergone CD4 or CD8 lineage commitment (e.g. $CD4^+CD8^{lo}TCR^{int}$ cells); (d) characterized by TCR gene rearrangement;(e) precursor thymocytes that are $CD4^+CD8^+$ double positive (DP);(f) $CD4^-CD8^+$ or $CD4^+CD8^-$ and optionally $TCR^{hi}$; (g) $CD3^+CD90^+$; (h) single positive cells that are $CD4^-CD8^+$ or $CD4^+CD8^-$ and $TCR^{hi}$; (i) $TCR\text{-}\alpha\beta^+$ and/or $TCR\text{-}\gamma\delta^+$; (j) characterized by expression of any of multiple Vβ chains (e.g. Vβ-3, -6, and 17a); or (k) mature and functional or activated T cells which may be characterized as $TCR/CD3^{hi}$ $CD4^-CD8^+$ or $CD4^+CD8^-$.

Methods for Generating or Expanding Cells of the T Cell Lineage

In an aspect of the invention, cells of the T cell lineage are generated from hematopoietic progenitor cells. Hematopoietic progenitor cells can be from a newborn mammal, a juvenile mammal, or an adult mammal. Preferred mammals include, for example, humans, non-human primates, mice, pigs, cows, and rats. They can be derived from bone marrow, blood, umbilical cord, stromal cells, fetal tissue and other sources that are known to those of ordinary skill in the art, or they may be derived from hematopoietic stem cells from such sources. Cells may be obtained from samples from an individual for use in a treatment (e.g. a patient sample) using standard techniques. In a particular embodiment, hematopoietic progenitor cells are obtained from fetal liver tissue, bone marrow, or thymus.

Negative and positive selection methods known in the art may be used for enrichment of the hematopoietic progenitor cells. For example, cells can be sorted based on cell surface antigens using a fluorescence activated cell sorter, or magnetic beads which bind cells with certain cell surface antigens. Negative selection columns can be used to remove cells expressing lineage specific surface antigens.

In an embodiment, $CD24^{lo}/lin^-$ hematopoietic progenitor cells are enriched for one or more of CD24, CD117 and Sca-1. In a preferred embodiment, the hematopoietic progenitor cells used in the methods of the invention are $Sca\text{-}1^{hi}CD117/c\text{-}Kit^{hi}CD24^{low}/Lin^-$.

In another aspect of the invention, embryonic stem cells are used to generate cells of the T cell lineage. Embryonic stem cells may be maintained as undifferentiated cells on embryonic fibroblast cells, which may include LIF.

Hematopoietic progenitor cells or embryonic stem cells are cultured with a system of the invention to form cells of the T cell lineage. The cells are cultured in the presence of one or more Notch ligand for a sufficient time to form cells of the T cell lineage.

In an embodiment, the hematopoietic progenitor cells or embryonic stem cells are cultured in a 6 cm or 10 cm tissue culture-treated dish with a Notch Ligand Cell Preparation. The concentration of hematopoietic progenitor cells or embryonic stem cells in the culture is between $1$-$10^9$, preferably $1 \times 10^2$ to $1 \times 10^6$, more preferably $1 \times 10^3$ to $1 \times 10^4$. In a particular embodiment, hematopoietic progenitor cells or embryonic stem cells (about $1$-$5 \times 10^4$ cells) are cultured on a monolayer of OP9 cells expressing Delta-like-1.

One or more positive cytokines that promote commitment and differentiation of cells of the T cell lineage may also be added to the culture. The cytokines may be human in origin, or may be derived from other species. The concentration of a cytokine in a culture is typically about 1-10 ng/ml. The following are representative examples of cytokines which may be employed in the present invention: all members of the fibroblast growth factor (FGF) family including FGF-4 and FGF-2, Flt-3-ligand, and interleukin-7 (I1-7). Preferably the cytokines used herein are Flt-3-ligand and I1-7. The cytokines may be used in combination with equal molar or greater amounts of a glycosaminoglycan such as heparin sulfate. The cytokines are commercially available or can be produced by recombinant DNA techniques and purified to various degrees. Some of the cytokines may be purified from culture media of cell lines by standard biochemical techniques.

The hematopoietic progenitor cells and embryonic stem cells may be cultured in culture medium comprising conditioned medium, non-conditioned medium, or embryonic stem cell medium. Examples of suitable conditioned medium include IMDM, DMEM, or αMEM, conditioned with embryonic fibroblast cells (e.g. human embryonic fibroblast cells or mouse embryonic fibroblast cells), or equivalent medium. Examples of suitable non-conditioned medium include Iscove's Modified Delbecco's Medium (IMDM), DMEM, or αMEM, or equivalent medium. The culture medium may comprise serum (e.g. bovine serum, fetal bovine serum, calf bovine serum, horse serum, human serum, or an artificial serum substitute) or it may be serum free.

The culture conditions entail culturing the hematopoietic progenitor cells or embryonic stem cells for a sufficient period of time so that cells in the preparation form cells of the T cell lineage. The cells are maintained in culture generally for 4-50 days, preferably 5 to 20 days. It will be appreciated that the cells may be maintained for the appropriate amount of time required to achieve a desired result i.e. a desired cellular composition. For example, to generate a cellular composition comprising primarily immature and inactivated T cells, the cells may be maintained in culture for about 5 to 20 days. Cells may be maintained in culture for 20 to 30 days to generate a cellular composition comprising primarily mature T cells.

The methods of the present invention lead to newly created cellular compositions comprising cells of the T cell lineage. The cells in the resulting T cell lineage compositions exhibit, or have the potential to differentiate into cells that exhibit morphological, physiological, functional, and/or immunological features of T cells. The cells in the resulting cellular compositions may be characterized by T cell markers.

A cellular composition resulting from a method of the invention may comprise one or more of the following cells:
   (a) progenitor or precursor cells committed to the T cell lineage;
   (b) $CD25^+$ $CD44^\pm$ $CD4^-$ $CD8^-$ cells;
   (c) cells that have undergone CD4 or CD8 lineage commitment (e.g. $CD4^+CD8^{lo}TCR^{int}$ cells);
   (d) precursor thymocytes that are $CD4^+CD8^+$ double positive (DP);
   (e) single positive cells that are $CD4^-CD8^+$ or $CD4^+CD8^-$ and optionally $TCR^{hi}$;
   (f) TCR-$\alpha\beta^+$ and/or TCR-$\gamma\delta^+$ T cells;
   (g) $CD3^+CD90^+$; or
   (h) mature and functional or activated T cells characterized as $TCR/CD3^{high}CD4^-CD8^+$ or $CD4^+CD8^-$.

In aspects of the invention, a cellular composition comprises (a); (a) and (b); (a) (b) and (c); (a), (b), (c), and (d); (a), (b), (c), (d), and (e); (a), (b), (c), (d), (e) and (f); (a) through (g) inclusive; (h); or (a) through (h) inclusive.

The cells in a cellular composition generated in accordance with the invention may be separated to obtain populations of cells largely consisting of one or more types of cells of the T cell lineage. Cells can be separated using standard techniques based on the expression of one or more phenotypic or physiological characteristics. Positive selection using antibodies to identify T cell specific cell surface markers, or negative selection using non-T cell specific markers (e.g. markers specific for NK cells) may be employed. For example, T cells can be screened for expression of specific markers such as CD8, CD4, and TCR using techniques such as flow cytometric cell sorting. Mature functional T cells are generally characterized as $CD4^-CD8^+TCR^{hi}$. Standard assay systems may also be used to identify functional mature T cells (e.g. see the T cell stimulation assay described herein).

Cell preparations comprising cells of the T cell lineage that are immature T cells may be induced to differentiate into mature T cells in vitro or in vivo. This may be accomplished in vitro by separating the immature T cells and culturing the cells in the presence of a Notch ligand or system as described herein, or culturing in an organ culture system (e.g. thymic organ culture). After differentiation of the cells into mature T cells, the cells may be separated to obtain a population of cells largely consisting of mature T cells. Immature T cells may also be administered to a subject in vivo and allowed to differentiate into mature T cells.

The methods of the invention also provide expanded populations of cells of the T cell lineage. Using a method of the invention it is possible to increase the number of cells of the T cell lineage by at least 15-20 fold each day after about 5-7 days in culture, and by at least about 1000-2000 fold after about 10-15 days in culture.

Modification of Cells of the T Cell Lineage Generated by a Method of the Invention Cellular compositions comprising cells of the T cell lineage generated using the methods of the invention may be genetically modified (transduced or transfected) either in nature or by genetic engineering techniques in vivo or in vitro. Cells can be modified by introducing mutations into genes in the cells or by introducing transgenes into the cells. Insertion or deletion mutations may be introduced in a cell using standard techniques. A gene encoding a selectable marker may also be integrated into the cells.

An aspect of the present invention relates to genetically engineering cells of T cell lineage compositions in such a manner that the cells or cells derived therefrom produce, in vitro or in vivo, polypeptides, hormones and proteins not normally produced in the cells in biologically significant amounts, or produced in small amounts but in situations in which regulatory expression would lead to a therapeutic benefit. For example, the cells could be engineered with a gene that expresses insulin at levels compatible with normal injected doses, or with a gene that can make up for a deficiency or abnormality of a gene causing a disease. Alternatively the cells could be modified such that a protein normally expressed will be expressed at much lower levels. These products would then be secreted into the surrounding media or purified from the cells. The cells formed in this way can serve as continuous short term or long term production systems of the expressed substance.

Thus, in accordance with this aspect of the invention, cells of the T cell lineage in cellular compositions generated using the methods of the invention can be modified with genetic material of interest. The modified cells can be cultured in vitro under suitable conditions so that they are able to express the product of the gene expression or secrete the expression product. These modified cells can be administered so that the expressed product will have a beneficial effect.

In a further embodiment, transduced immature T cells with the potential to form mature T cells can be induced in vivo to differentiate into T cells that will express the gene product. For example, the transduced cells may be administered to induce production of T cells having the transduced gene. The cells may be administered in a mixture with other cells or separately and may be delivered to a targeted area. The cells can be introduced intravenously and home to a targeted area. Alternatively, the cells may be used alone and caused to differentiate in vivo.

Thus, genes can be introduced into cells which are then injected into a recipient where the expression of the gene will have a therapeutic effect. For example, an insulin gene may be introduced into the cells to provide a constant therapeutic dose of insulin in the bone marrow and peripheral blood.

The technology may be used to produce additional copies of essential genes to allow augmented expression by T cells of certain gene products in vivo. These genes can be, for example, hormones, matrix proteins, cell membrane proteins, and cytokines.

Applications

The T cell lineage compositions comprising cells of the T cell lineage generated using the methods of the invention can be used in a variety of methods (e.g. transplantation) and they have numerous uses in the field of medicine.

Transplantation, as used herein, can include the steps of isolating a cellular composition comprising cells of the T cell lineage according to the invention and transferring cells in the composition into a mammal or a patient. Transplantation can involve transferring the cells into a mammal or a patient by injection of a cell suspension into the mammal or patient, surgical implantation of a cell mass into a tissue or organ of the mammal or patient, or perfusion of a tissue or organ with a cell suspension. The route of transferring the cells may be determined by the requirement for the cells to reside in a particular tissue or organ and by the ability of the cells to find and be retained by the desired target tissue or organ.

In an aspect of the invention, the newly created cellular compositions comprising cells of the T cell lineage, and cellular compositions comprising T cells differentiated therefrom (e.g. mature T cells), can be used in both cell therapies and gene therapies aimed at alleviating disorders and diseases in particular those involving T cells.

The cell therapy approach involves the use of transplantation of the newly created cellular compositions comprising cells of the T cell lineage or cellular compositions comprising T cells differentiated therefrom (e.g. mature T cells) as a treatment for diseases. The steps in this application include: (a) producing a cellular composition comprising cells of the T cell lineage, or a cellular composition comprising cells differentiated therefrom, as described herein; and (b) allowing the cells to form functional connections either before of after a step involving transplantation of the cells. The gene therapy may also involve transfecting the newly created cells with an appropriate vector containing a cDNA for a desired protein, followed by a step where the modified cells are transplanted.

In either a cell or gene therapy approach, therefore, cells of the T cell lineage in cellular compositions of the present invention can be transplanted in a patient in need. Thus, the cellular compositions with cells of the T cell lineage or mature T cells differentiated therefrom can be used to replace T cells in a patient in a cell therapy approach, useful in the treatment of diseases. These cells can be also used as vehicles for the delivery of specific gene products to a patient.

The invention also provides a method of treating a patient with a condition involving T cells or requiring replacement of T cells comprising transferring a cellular composition comprising cells of the T cell lineage into the patient.

Still another aspect of the invention is a kit for producing cellular compositions comprising cells of the T cell lineage. The kit includes the reagents for implementing a method or system of the present invention. This kit preferably includes at least one Notch Ligand Cell Preparation, and instructions for its use.

The cellular compositions comprising cells of the T cell lineage may be used to screen for potential modulators or therapeutics that modulate development or activity of cells of the T cell lineage or cells differentiated therefrom. In particular, the cellular compositions may be subjected to a test substance, and the effect of the test substance may be compared to a control (e.g. in the absence of the substance) to determine if the test substance modulates development or activity of cells of the T cell lineage or cells differentiated therefrom.

In an aspect of the invention a method is provided for using a cellular composition of the invention comprising cells of the T cell lineage or cells differentiated therefrom to assay the activity of a test substance comprising the steps of:
(a) generating cells of the T cell lineage with a system or method of the invention in the presence of a test substance, or culturing cells of T cell lineage compositions generated using a system or method of the invention in the presence of a test substance; and
(b) detecting the presence or absence of an effect of the test substance on the survival of the cells or on a morphological, functional, or physiological characteristic and/or molecular biological property of said cells, whereby an effect altering cell survival, a morphological, functional, or physiological characteristic and/or a molecular biological property of the cells indicates the activity of the test substance.

In another aspect a method is provided for using cells of the T cell lineage or cells differentiated therefrom generated in accordance with the invention, to screen a potential new drug to treat a disorder involving T cells comprising the steps of:
(a) generating cells of the T cell lineage with a system or method of the invention in the presence of a potential new drug, or culturing cells of T cell lineage preparations generated using a system or method of the invention in the presence of a potential new drug; and
(b) detecting the presence or absence of an effect of the potential new drug on the survival of the cells in vitro or on a morphological, functional or physiological characteristic and/or molecular biological property of said cells, whereby an effect altering cell survival, a morphological, functional, or physiological characteristic and/or a molecular biological property of the cells in vitro indicates the activity of the potential new drug.

The cellular compositions of the invention may be used to prepare model systems of disease. The cellular compositions of the invention can also be used to produce growth factors, hormones, etc.

The cellular compositions of the invention can be used to screen for genes expressed in or essential for differentiation of T cells. Screening methods that can be used include Representational Difference Analysis (RDA) or gene trapping with for example SA-lacZ (D. P. Hill and W. Wurst, Methods in Enzymology, 225: 664, 1993). Gene trapping can be used to induce dominant mutations (e.g. by deleting particular domains of the gene product) that affect differentiation or activity of T cells and allow the identification of genes expressed in or essential for differentiation of these cells.

The cellular compositions and expanded cellular compositions of the invention comprising increased numbers of cells of the T cell lineage may be used for enhancing the immune system of a patient. The cellular compositions will facilitate enhancement or reconstitution of the patient's immune system.

In an aspect of the invention, the cellular compositions are used in the treatment of leukemia, lymphomas, or other cancers in which therapy results in the depletion of T cells.

In another aspect of the invention, a cellular composition of the invention is used to treat subjects infected with HIV-1 that have undergone severe depletion of their T cell compartment resulting in a state of immune deficiency.

The cells of the T cell lineage in a cellular composition, in particular an expanded cellular composition, may be transfected with a desired gene that can be used for treatment of genetic diseases. Hematopoietic cell-related genetic diseases can be treated by grafting the cellular composition with cells transfected with a gene that can make up for the deficiency or the abnormality of the gene causing the diseases. For example, a normal wild type gene that causes a disease such as β-thalassemia (Mediterranean anemia), sickle cell anemia, ADA deficiency, recombinase deficiency, recombinase regulatory gene deficiency and the like, can be transferred into the cells of the T cell lineage by homologous or random recombination and the cells can be grafted into a patient. Further, a cellular composition comprising normal T cells free from abnormalities of genes (from a suitable donor) can be used for treatment.

Another application of gene therapy permits the use of a drug in a high concentration, which is normally considered to be dangerous, by providing drug resistance to normal T cells by transferring a drug resistant gene into the cells. In particular, it is possible to carry out the treatment using an anticancer drug in high concentration by transferring a gene having drug resistance against the anticancer drug, e.g., a multiple drug resistant gene, into cells of the T cell lineage in a cellular composition of the invention.

Diseases other than those relating to the hematopoietic system can be treated by using the cellular compositions comprising cells of the T cell lineage in so far as the diseases relate to a deficiency of secretory proteins such as hormones, enzymes, cytokines, growth factors and the like. A deficient protein can be induced and expressed by transferring a gene encoding a target protein into the cells of the T cell lineage under the control of a suitable promoter. The expression of the protein can be controlled to obtain the same activity as that obtained by the natural expression in vivo.

It is also possible to insert a gene encoding a ribozyme, an antisense nucleic acid or the like (e.g., short-interfering RNA) or another suitable gene into cells of the T cell lineage to control expression of a specific gene product in the cells or to inhibit susceptibility to diseases. For example, the cells of the T cell lineage can be subjected to gene modification to express an antisense nucleic acid, siRNA, or a ribozyme, which can prevent growth of hematic pathogens such as HIV, HTLV-I, HTLV-II and the like in cells of the T cell lineage. In an embodiment, cells of the T cell lineage of a cellular composition of the invention are created which express known inhibitory genes of HIV replication, such as RNA decoys or the Tat- or Rev-responsive elements, or a dominant negative mutant of the Rev trans-activator protein. Cells of the T cell lineage derived from hematopoietic progenitor cells or ES carrying these genes would provide a potentially limitless and defined source of HIV-resistant lymphocyte progenitors.

The cellular compositions comprising cells of the T cell lineage can be introduced in a vertebrate, which is a recipient of cell grafting, by, for example, conventional intravenous administration.

Having now described the invention, the same will be more readily understood through reference to the following examples which are provided by way of illustration, and are not intended to be limiting of the present invention.

EXAMPLES

Example 1

OP9 Cell Characterization and Expression of Notch Ligands

Experimental Procedures

Mice: Timed-pregnant Swiss. NIH mice were obtained from the National Cancer Institute, Frederick Cancer Research and Development Center (Frederick, Md.). RAG-2-deficient mice (Shinkai et al., 1992) were bred and maintained in the animal facility at the Department of Immunology, University of Toronto, Sunnybrook and Women's College Health Sciences Centre.

Flow cytometry and cell sorting: Flow cytometry was performed using a FACScalibur (BD Biosciences, San Diego, Calif.) instrument, as previously described (Carlyle and Zúñiga-Pflücker, 1998). FITC-, PE-, biotin-, and APC-conjugated mAbs and streptavidin-APC were purchased from BD Biosciences. For analysis, live cells were gated based on forward- and side-scatter, and lack of propidium iodide uptake. Intracellular staining was performed using the Cytofix/Cytoperm with GolgiStop kit according to manufacturer's instructions (BD Biosciences). Cells were sorted using a FACSDiVa (BD Biosciences). Sorted cells were ≧99% pure, as determined by post sort analysis.

OP9-DL1 and OP9-DL4 cells: OP9 cells (Kodama et al., 1994) were infected with the empty MigR1 retroviral vector (Pui et al., 1999) or with the MigR1 retroviral vector engineered to express the Delta-like-1 gene (Kuroda et al., 1999), or the Delta-like4 gene, 5' of the internal-ribosomal entry site, allowing the bicistronic expression of Delta-like-1 or Delta-like-4 and green fluorescent protein (GFP). The MigR1 retroviral backbone was obtained from W. Pear (University of Pennsylvania, PA.). The retroviral vectors were packaged using the PT67 retroviral packaging cell line (Clonetech-BD Biosciences). The Delta-like-1 gene containing a 3' T7 tag was provided by T. Honjo (Kyoto University, Japan). The Delta-like-4 gene was cloned from cDNA obtained from fetal thymus mRNA, which was amplified by RT-PCR using Delta-like-4 specific primers (with the 3' primer also containing the FLAG-tag sequence), and the PCR product (Delta-like-4 gene containing a 3' FLAG tag) was cloned into the pcDNA3.1/TOPO plasmid (Invitrogen). The following primers were used.

The original primers used to clone Dll4 are:

```
UPPER
(5'): ACACCCCAAGGGATGACG      (SEQ ID NO. 24)

LOWER
(3'): CCTCTGTGGCAATCACAC      (SEQ ID NO. 25)
```

The Flag-Tag (and the last AA) was added with the following 3' primer:

```
TCTGAATTCTTAGGACTTGTCATCGTCGTCCTTG (SEQ ID NO. 26)
TAGTCAGCTACCTCTGTGGCAATCAC
```

Figure 2:
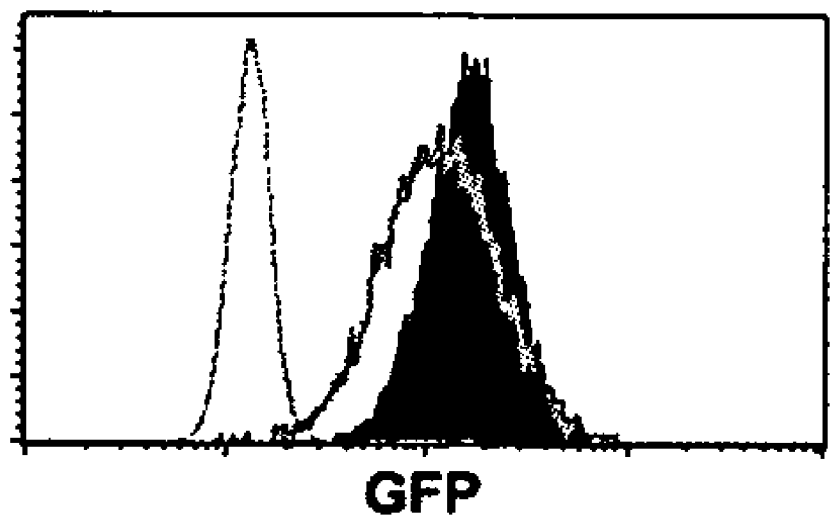
FIG. 2. Delta-like-1 expression by retrovirally-transduced OP9 cells. Flow cytometric analysis for the expression GFP (top panel) and the Delta-like-1 gene product (bottom panel) following intracellular staining for the carboxy-terminal T7 tag of the Delta-like-1:T7 protein in OP9-DL1 cells (filled histogram), or OP9-GFP cells (solid line); control uninfected OP9 cells are shown in the top panel (thin line).
Figure 2:
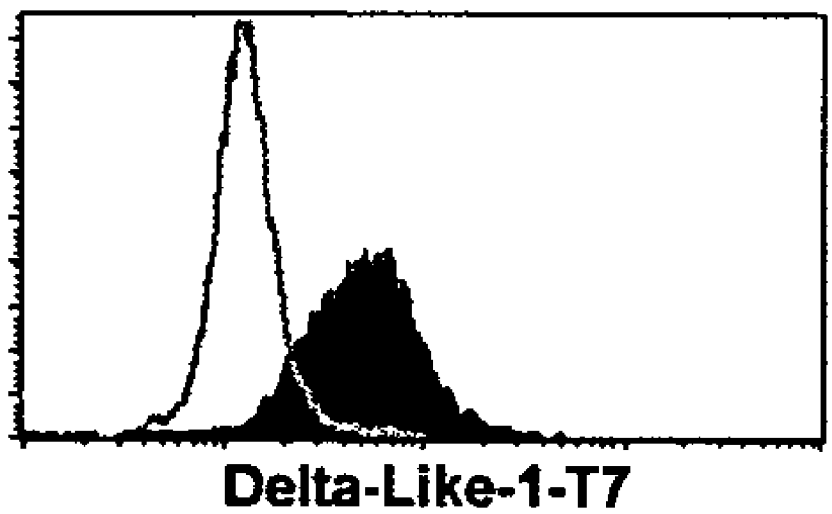

Retrovirally-transduced OP9 cells were sorted on the basis of GFP expression, and expression of the Delta-like-1:T7 product was determined by intracellular staining (see FIG. 2). Delta-like-4 expressing OP9 cells were obtained in a similar manner.

PCR and RT-PCR: Genomic DNA was purified from embryonic fibroblasts, d14 fetal thymus, cells obtained from day 7 HSC/OP9-DL1 cocultures, and cocultured cells sorted for a CD44⁻ CD25⁺ phenotype using the EasyDNA kit (Invitrogen, Carlsbad, Calif.). 100 ng of each DNA sample was amplified using a PTC-225 Peltier Thermal Cycler (MJ Research, Waltham, Mass.). Primers used for the TCR $D_\beta$-$J_\beta$ rearrangement analysis have been previously described (Rodewald et al., 1994). Products were separated by agarose gel electrophoresis and visualized by ethidium bromide staining. All PCR products shown correspond to expected molecular sizes. For RT-PCR analysis, single-cell suspensions were prepared from OP9 cells and from d14 fetal thymuses treated for 7 days in organ culture with 1.1 mM deoxyguanosine. Isolation of total RNA and RT reactions were carried out as previously described (Carlyle and Zúñiga-Pflücker, 1998). All semiquantitative PCR reactions were performed using the same serially-diluted cDNA batches as shown for β-actin. Gene-specific primers used for PCR are as follows:

```
Notch-1 upper
GGAGCGGTGTGAGGGTGATG,         [SEQ ID NO. 12]

lower
ATCTGCGGTGGGGGAATGTC;         [SEQ ID NO. 13]

Jagged-1 upper
TCTCTGACCCCTGCCATAAC,         [SEQ ID NO. 14]

lower
TTTACAGGGGTTGCTCTCG;          [SEQ ID NO. 15]

Jagged-2 upper
GCAAAGAAGCCGTGTGTAAA,         [SEQ ID NO. 16]

lower
TAATAGCCGCCAATCAGGTT;         [SEQ ID NO. 17]

Delta-like-1 upper
ACCTCGGGATGACGCCTTTG,         [SEQ ID NO. 18]

lower
GACCACCACAGCAGCACAG; and      [SEQ ID NO. 19]

Delta-like-4 upper
GCACCAACTCCTTCGTCGTC,         [SEQ ID NO. 20]

lower
TCACAAAACAGACCTCCCCA.         [SEQ ID NO. 21]
```

Results

Expression of Notch Ligands by OP9 Cells

Although OP9 cells have been shown to support the differentiation of HPCs into multiple lineages (Kodama et al., 1994), including B cells (Carlyle et al., 1997), efforts to induce T cell differentiation in vitro have been unsuccessful in the absence of a thymic microenvironment. To determine whether OP9 cells fail to express Notch ligands, which may provide essential cell contact-dependent signals required for T cell commitment and differentiation (Radtke et al., 1999), OP9 cells were analyzed for the expression of these molecules by reverse transcriptase-PCR(FIG. 1). This analysis revealed that transcripts for Delta-like-1 and Delta-like-4 were undetectable in OP9 cells, while these transcripts were present in thymus stroma-enriched cell suspensions (FIG. 1). On the other hand, transcripts for Jagged-1 and Jagged-2 were detected in both OP9 cells and thymic stroma cells (FIG. 1).

Delta-like-1 has been shown to efficiently engage and induce Notch receptor signaling (Kuroda et al., 1999). The lack of Delta-like-1 or Delta-like-4 expression by OP9 cells may be responsible for their inability to support T cell lineage commitment and differentiation, while allowing efficient generation of B cells from HPCs. To test this OP9 cells were generated expressing high levels of Delta-like-1 or Delta-like-4 by retroviral-mediated gene transfer with either a Delta-like-1-expression construct (D11-1:T7-IRES-GFP) or Delta-like-4 expression construct (D11-4:Flag-IRES-GFP). Control OP9 cells transduced with the empty vector, expressing GFP alone, were also generated. Flow cytometric analysis showed that GFP was expressed at similar levels in both OP9-GFP and OP9-DL1 cell lines (FIG. 2, top panel). FIG. 2 also shows an analysis of intracellular staining for the carboxy-terminal T7-tag of the Delta-like-1 gene product in the resulting OP9-DL1 cells, and the control OP9-GFP cells, demonstrating that OP9-DL1 cells uniformly express the Delta-like-1 molecule.

Example 2

Induction of T Cell Differentiation by OP9-DL1 Cells

Figure 3:
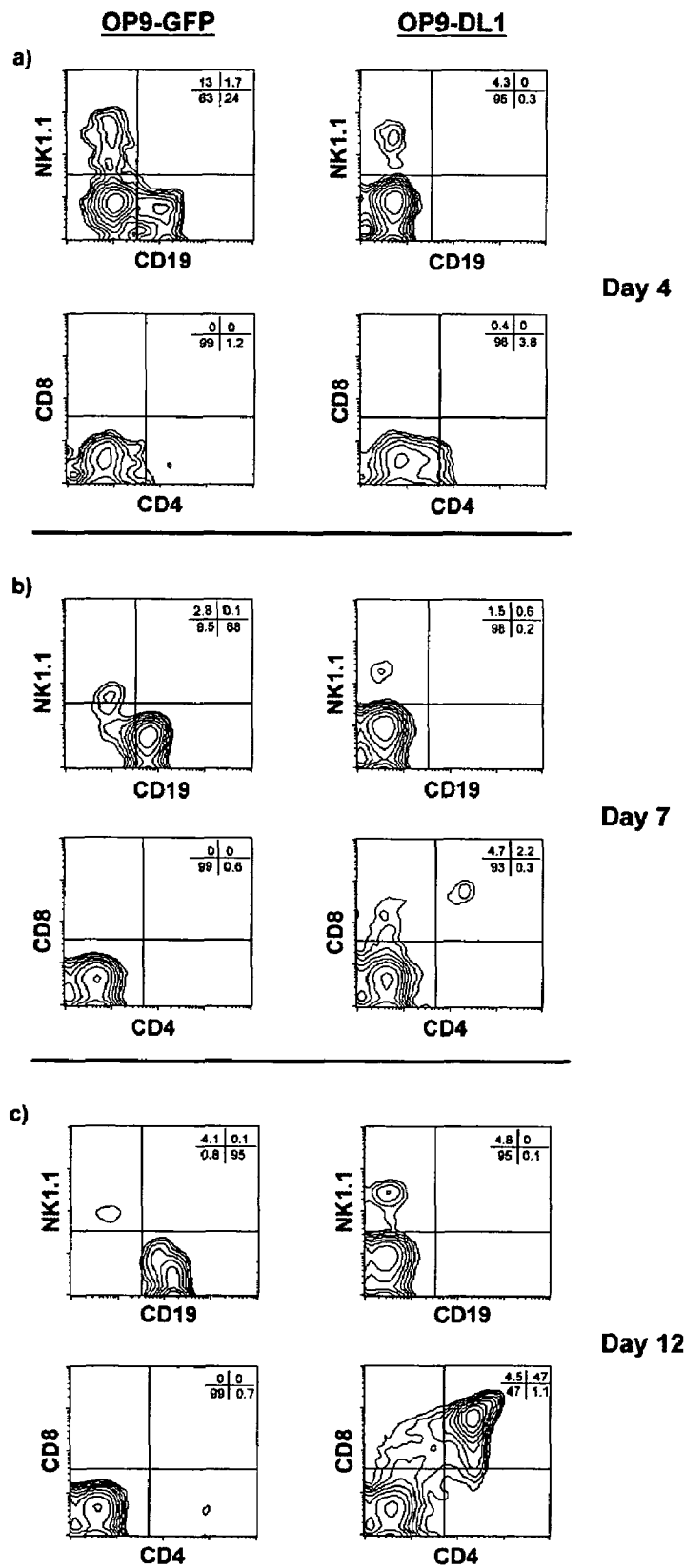
FIG. 3. Lineage commitment and differentiation of HPCs cultured on OP9-GFP cells or OP9-DL1 cells. Flow cytometric analysis for B cell and NK cell markers (CD19 and NK1.1 respectively), or T cell markers (CD4 and CD8) from HPCs cultured on either OP9-GFP cells or OP9-DL1 cells for a, 4 days, b, 7 days, or c, 12 days. The difference in the levels of NK1.1 staining in the left panels of b and c are due to the use of different fluorochrome-labeled anti-NK1.1 mAbs.

Experimental Procedures:

FL-HPC differentiation: HPCs were isolated from the FL of day 14 embryos by cell sorting (Sca-1$^{hi}$ CD117/c-Kit$^{hi}$ CD24$^{low}$/Lin⁻), and placed in culture either with OP9-GFP cells, OP9-DL1 cells. Flow cytometric analysis was performed at several time points during the coculture period to determine the ability of each stromal cell line to support the differentiation of HPCs into various lymphoid lineages (FIG. 3).

ESC differentiation: The ESC line R1 were obtained from G. Caruana(Mt. Sinai Hospital, Toronto). Embryonic fibroblasts were generated from day 15-18 embryos as previously described[33]. Embryonic fibroblasts were cultured in ES media (DMEM, supplemented with 15% FCS, 10 U/ml penicillin, 100 μg/ml streptomycin, 100 μg/ml gentamicin, 2 mM glutamine, 110 μg/ml sodium pyruvate, 50 mM 2-mercaptoethanol, and 10 mM Hepes). ESCs were maintained by culture in ES media containing 1 ng/ml leukemia inhibitory factor (R & D Systems, Minneapolis, Minn.) on irradiated embryonic fibroblasts. ESCs were induced to differentiate by culture on either OP9-control or OP9-DL1 cell lines in the absence of LIF. On day 5 of culture, when most ESC colonies were mesoderm-like in appearance, ESC/OP9 co-cultures were disrupted by treatment with 0.25% trypsin (GIBCO/

BRL). The resulting single-cell suspension was preplated for 30 minutes, and non-adherent cells were then replated onto fresh OP9 cells in OP9 media containing 5 ng/ml Flt3-L (Peprotech, Rocky Hill, N.J.). On day 8 of culture and every 4 days thereafter, non-adherent ESC derived hematopoietic cells were harvested by vigorous pipetting, filtered through a 40 µm nylon mesh, and transferred onto fresh OP9 monolayers in OP9 media containing 5 ng/ml Flt3-L and 5 ng/ml IL-7 (Peprotech, Rocky Hill, N.J.).

BM HSC differentiation: The bone marrow was purified from the femurs 4-6 week old mice and disrupted by repetitive passage through a 25 gauge syringe needle. HSCs ($CD117^+$ $Sca-1^{hi}$) were purified from bone marrow-derived hematopoietic cells by flow cytometric cell sorting.

Results

As expected, HPCs cocultured with OP9-GFP cells did not give rise to T cells, and therefore these cultures did not contain CD4 or CD8 expressing cells (FIGS. 3a-c). Rather, as previously described (Carlyle et al., 1997), HPCs cultured with OP9-GFP cells gave rise to B cells and NK cells within 4 days, and these cells expanded throughout the culture period (FIGS. 3a-c). In striking contrast, HPCs cultured on OP9-DL1 cells gave rise to $CD4^+$ $CD8^+$ immature DP T cells after 7 days of coculture, and these DP T cells accounted for the majority of HPC-derived cells by day 12 (FIGS. 3b-c). The temporal kinetics of DP T cell differentiation in the presence of OP9-DL1 cells is similar to that observed following transfer of HPCs into fetal thymic organ culture (Carlyle et al., 1997).

Figure 9:
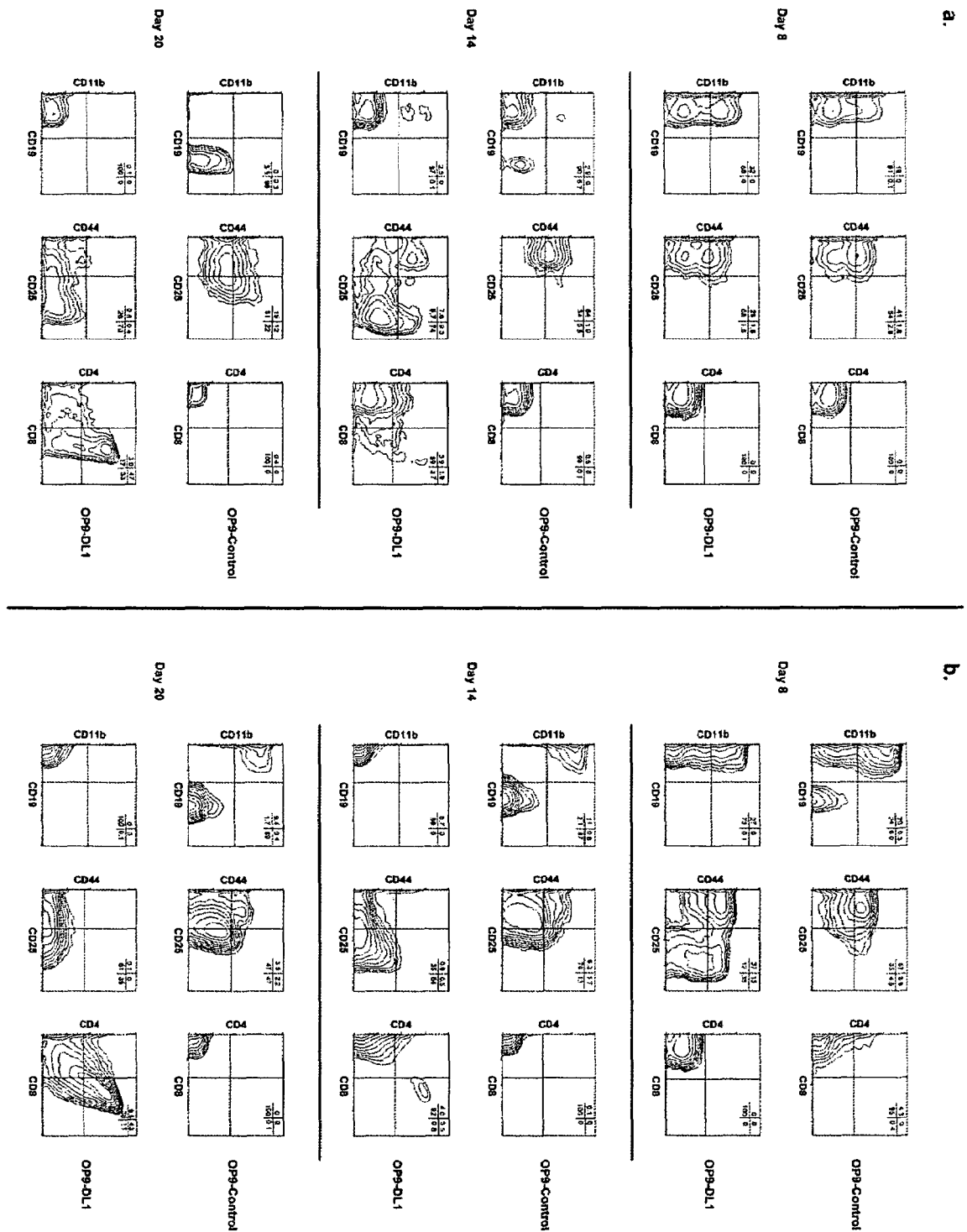
FIG. 9. a) ES cells or b) Bone marrow-derived HPCs were induced to differentiate in vitro by culturing on OP9-GFP or OP9-DL 1 cells. Non-adherent cells from ES/OP9 cocultures were analyzed by flow cytometry for lineage specific markers, as indicated, on day 8 (a), day 14 (b) and day 20 (c) of coculture.

In addition, approximately a 100 fold increase in cellularity was observed during the first week of culture, with the cell yields continuing to increase another 15-20 fold by day 12. In addition to CD4- and CD8-expressing cells, day 12 cultures also contained a small population of presumably mature SP T cells. Both DP and CD8 SP T cells derived from HPC/OP9-DL1 coculture expressed CD8β as well as CD8α on the cell surface. In order to determine whether ESCs, when cultured on OP9 cells expressing DL1 (OP9-DL1), could be directed to differentiate into T lymphocytes, we placed undifferentiated ESCs on either OP9-control cells or OP9-DL1 cells (FIG. 9a). The differentiation of ESCs cultured on these two stromal cell lines was analyzed in parallel to bone marrow-derived HSCs (FIG. 9b). ESCs differentiated on OP9 cells gave rise to an early wave of erythro-myeloid lineage cells, such that CD11b and Ter119 were the only lineage-specific markers observed on day 8 of both cultures (FIG. 9 and data not shown). However, these erythro-myeloid cells steadily declined in both control OP9 and OP9-DL1 cultures, as lymphoid cells became the predominant cells in the cultures at later days of development.

On day 14, a small population of B cell progenitors began to emerge from ESCs cultured on control OP9 cells (FIG. 9a). In contrast, ESCs cultured on OP9-DL1 cells gave rise to a population of cells expressing CD25 and/or CD44, and hence likely to belong to the T cell lineage. Thus, ESCs cultured on OP9-DL1 cells appear to follow a typical thymocyte developmental progression through the CD4 CD8 double negative (DN) stage, as defined by CD44 and CD25 expression[24]. Furthermore, these day 14 cultures contained a small population of CD4 and CD8 double positive (DP) cells.

Example 3

Induction of T-cell Differentiation by OP9-DL4 Cells.

Experimental Procedures:

FL-derived HPC differentiation on OP9-DL4 cells: HPCs were isolated from the FL of day 14 embryos by cell sorting ($Sca-1^{hi}$ $CD117/c-Kit^{hi}$ $CD24^{low}/Lin^-$), and placed in culture either with OP9-GFP cells, or OP9-DL4 cells. Flow cytometric analysis was performed at several time points during the coculture period to determine the ability of each stromal cell line to support the differentiation of HPCs into various lymphoid lineages.

Results

Figure 10:
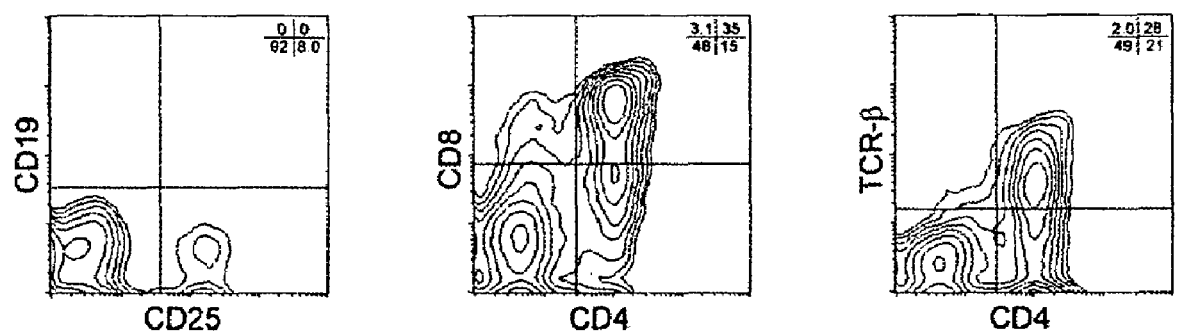
FIG. 10. Lineage commitment and differentiation of HPCs cultured on OP9-DL4 cells. Flow cytometric analysis for several cell surface markers (CD19 vs CD25, CD4 vs CD8, and CD4 vs TCRβ) from FL-derived HPCs cultured on OP9-DL4 cells for 11 days (with the addition 5 ng/ml of Flt3-L and 5 ng/ml IL-7).

To determine whether OP9 cells expressing the Notch ligand Delta-like-4 would support the induction of T cell differentiation from FL-derived HPCs, we cultured HPCs on a monolayer of OP9 cells expressing Delta-like-4 (OP9-DL4). In keeping with our results with HPCs differentiating on OP9-DL1 cells, we did not detect $CD19^+$B lineage cells in HPC/OP9-DL4 cocultures (FIG. 10). Rather, HPCs cultured on OP9-DL4 cells gave rise to $CD4^+$ $CD8^+$ immature DP T cells after 7 days of coculture, and robust T cell differentiation was be observed by day 11 of coculuture, in which TCR-bearing T cells were also readily detected (FIG. 10). The temporal kinetics of DP T cell differentiation in the presence of OP9-DL4 cells is similar to that observed following transfer of HPCs to OP9-DL1 cells. Thus, FIG. 10 shows that OP9 cells expressing Delta-like-4, in a similar manner as OP9 cells expressing Delta-like-1, can induce T cell lineage commitment and support the normal differentiation of T cells from a defined source of stem cells, and in particular FL-derived HPCs.

Example 4

Demonstration that OP9 Cells Expressing Notch Ligands do not Support B Cell Lymphopoiesis Experimental Procedures: As in Example 2.

Results:

OP9 Cells Expressing Notch Ligands do not Promote Differentiation into B Cells

Notably, HPCs cocultured with OP9-DL1 or OP9-DL4cells failed to give rise to B cells, while the differentiation of NK cells was readily observed throughout the coculture period (FIGS. 3a-c FIG. 10). These findings are consistent with the interpretation that Notch/Delta-like-1 interactions induce the commitment and differentiation of FL-derived HPCs towards the T cell lineage, while inhibiting the development of B cells.

Only B cells were observed by day 20 from ESCs cultured on control OP9 cells. In striking contrast, ESCs cultured on OP9-DL1 cells failed to generate B cells, rather, these cultures contained a robust population of DP cells, which accounted for close to half of the hematopoietic cells present in the cultures. (FIG. 9a.)

Bone marrow derived $CD117^+$ $Sca-1^{hi}$ $Lin^-$ HSCs were also differentiated on OP9-control or OP9-DL1 cells (FIG. 9b). Initially, the HSCs developed with faster temporal kinetics as compared to the ESC cultures (FIG. 9a). As early as day 8 of culture, $CD19^+$ B lineage cells can be observed from OP9-control cultures, while a large population of DN $CD25^+$ cells can be observed in OP9-DL1 cultures. By comparison, the ESC cultures contained a similarly large proportion of $CD44^-$ $CD25^+$ DN cells on day 14 of culture as that observed from HSCs cultured for 8 days, and yet these cultures contained a comparable percentage of DP cells when analyzed on day 20. These data suggest that the hematopoietic progenitor cells that develop from ESCs cultured on OP9-DL1 cells develop faster than their adult counterparts. In keeping with this, our previous findings showed that fetal liver-derived HSCs cultured on OP9-DL1 (FIG. 3) also require less than a week to develop from the DN to DP stage of T cell development.

OP9-DL1 Cells Support the Growth of Committed Pre-B Cells

Figure 4:
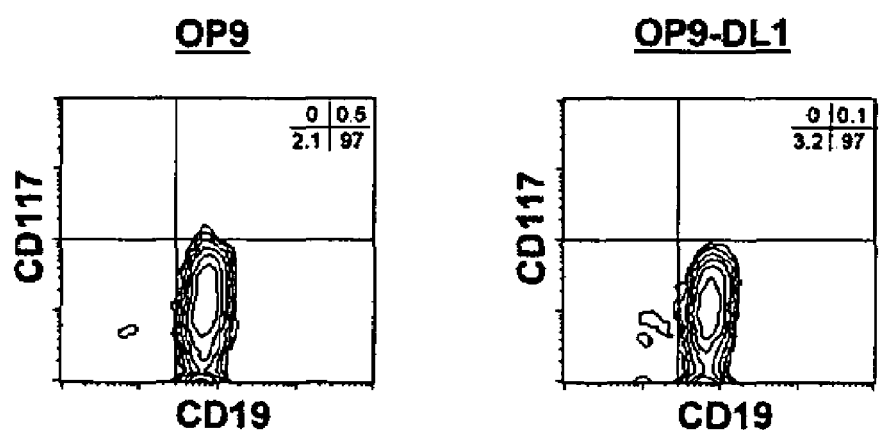
FIG. 4. Differentiation and proliferation of pre-B cells cultured on OP9 cells or OP9-DL1 cells. Flow cytometric analysis for surface expression of CD19 and CD117 of pre-B cells (CD117$^+$ B220$^+$ CD19$^+$) sorted from the adult BM and cultured for 7 days on either control OP9 cells or OP9-DL1 cells.

To determine whether the absence of B cells among the progeny of HPCs cultured on OP9-DL1 cells resulted from an inhibition of B cell commitment or growth, committed CD117$^+$ CD45R/B220$^+$ CD19$^+$ pre-B cells were isolated from adult BM (Boekel et al., 1997). These pre-B cells were placed in culture with either OP9 or OP9-DL1 cells for 7 days, and then analyzed by flow cytometry. FIG. 4 shows that pre-B cells cultured on either OP9 cells or OP9-DL1 cells were able to proliferate and further differentiate into the more mature CD117$^-$ CD19$^+$ stage. After 7 days, a small percentage of cells from each culture also expressed surface IgM. In keeping with the pre-B cell phenotype of the starting population, neither T cells nor NK cells were detected in these cultures. Since pre-B cells have been shown to express Notch-1 (Bertrand et al., 2000), these data suggest that the Delta-like-1-mediated inhibition of B lineage development observed in FIG. 3 occurs at the earliest stages of lymphocyte lineage commitment, as it does not affect already-committed B cell precursors.

Example 5

TCR-β Locus Rearrangement as a Marker for T-cell Commitment

Experimental Procedures: As in Example 2

PCR and RT-PCR: Genomic DNA was purified using the Easy DNA kit (Invitrogen, Carlsbad, Calif.) from embryonic fibroblasts, d14 fetal thymus, and from CD117$^-$ CD44$^-$ CD25$^+$ DN3 cells from ESC/OP9-DL1 cultures. 100 ng of each DNA sample was amplified using a PTC-225 Peltier Thermal Cycler (MJ Research, Waltham, Mass.). Primers used for the TCR D$_\beta$-J$_\beta$ rearrangement analysis have been previously described. Isolation of total RNA and RT reactions was carried out as previously described. All semiquantitative PCR reactions were performed using the same serially-diluted cDNA batches as shown for β-actin. The gene-specific primers, expected product lengths, and annealing temperatures are listed in Table 1. PCR products were separated by agarose gel electrophoresis and visualized by ethidium bromide staining. All PCR products shown correspond to expected molecular sizes.

Results

Figure 5:
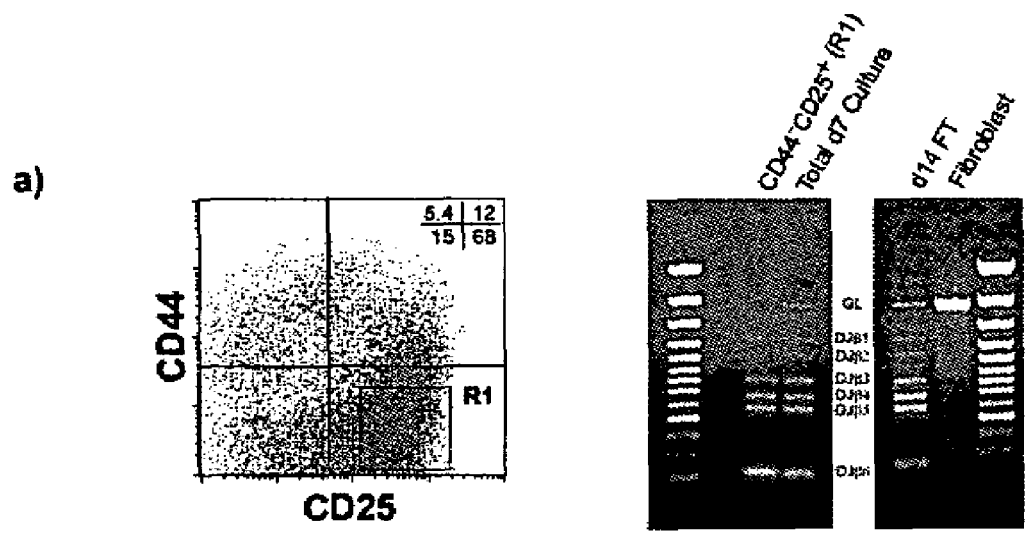
FIG. 5. HPCs cultured on OP9-DL1 cells recapitulate intrathymic T cell development. a, Flow cytometric analysis for CD44 and CD25 expression from day 7 HPC/OP9-DL1 cocultures. TCR-β rearrangement status was analyzed by PCR using DNA isolated from sorted CD44$^-$ CD25$^+$ cells (R1-gated), total day 7 coculture cells, day 14 fetal thymus, and embryonic fibroblasts. b, Day 12 HPC/OP9 and HPC/OP9-DL1 cocultures were analyzed for γδ- and αβ-TCR surface expression by flow cytometry. c, Day 12 HPC/OP9-DL1 cocultures were analyzed for TCR-Vβ-3, -6, and -17 a surface expression by flow cytometry.
Figure 5:
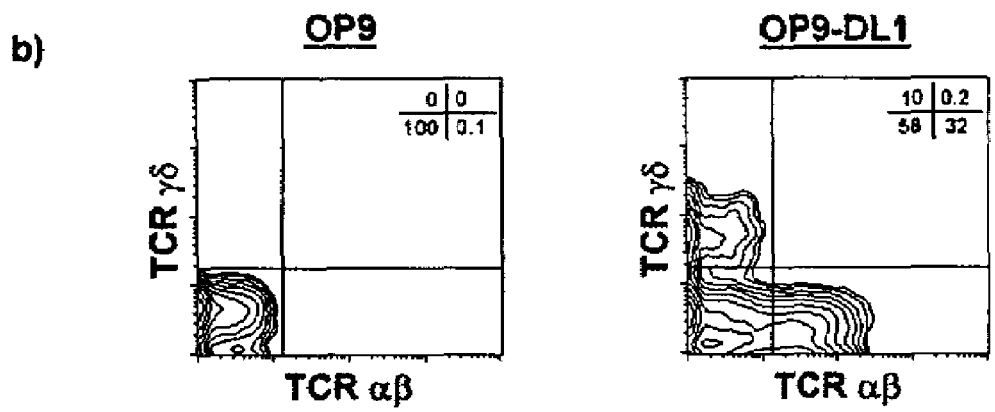
Figure 5:
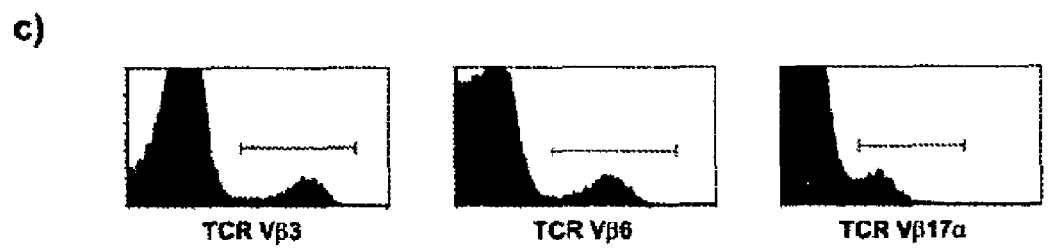

Rearrangement at the TCR-β gene locus is a hallmark of T cell lineage commitment, and is essential for the progression of DN thymocytes to the DP stage during normal αβ T cell development. To address whether T cells derived from HPCs cultured on OP9-DL1 cells followed the normal pattern of development observed in the thymus, cells from day 7 cocultures, which mostly display a CD4$^-$CD8$^-$ surface phenotype (FIG. 3), were analyzed for CD44 and CD25 surface expression (FIG. 5). Strikingly, these cells exhibited a pattern of CD44/CD25 expression that is similar to that observed among immature CD4$^-$ CD8$^-$ thymocytes. The similarities between T cell development occurring in the thymus and on the OP9-DL1 cells also applied to the regulation of DNA rearrangement at the TCR-β locus. In this regard, a similar pattern of D$_\beta$-J$_\beta$ rearrangement was observed from DNA obtained either from the day 7 coculture cells (total or sorted CD44$^-$ CD25$^+$ cells) or from day 14 fetal thymocytes (FIG. 5). In contrast, and as expected, DNA from fibroblasts was in germline configuration at the same locus. These results indicate that T lineage cells that develop from HPC/OP9-DL1 cocultures undergo a normal program of differentiation.

Two distinct lineages of TCR-bearing T cells normally develop in the thymus (Shortman and Wu, 1996). To determine whether both lineages could be generated from HPCs cultured on OP9-DL1 cells, cells from day 12 cocultures were analyzed for αβ- and γδ-TCR surface expression (FIG. 5b). As expected, HPCs cultured on OP9 cells did not contain αβ- or γδ-TCR-bearing cells after 12 days in culture. In contrast, HPCs cocultured with OP9-DL1 cells contained both αβ- and γδ-T cells. Furthermore, to determine whether a broad distribution of TCR-Vβ usage occurred during T cell differentiation on OP9-DL1 cells, an analysis was conducted for the expression of several Vβ chains commonly used by T cells derived from Swiss.NIH mice, which are of the Vβ$_a$ haplotype. FIG. 5c shows that multiple Vβ chains (Vβ-3, -6, and -17a) are expressed, with no apparent bias in Vβ usage. Furthermore, TCR-Vβ chains were clonally expressed, indicating that allelic exclusion at the TCRβ gene locus was enforced.

Figure 12:
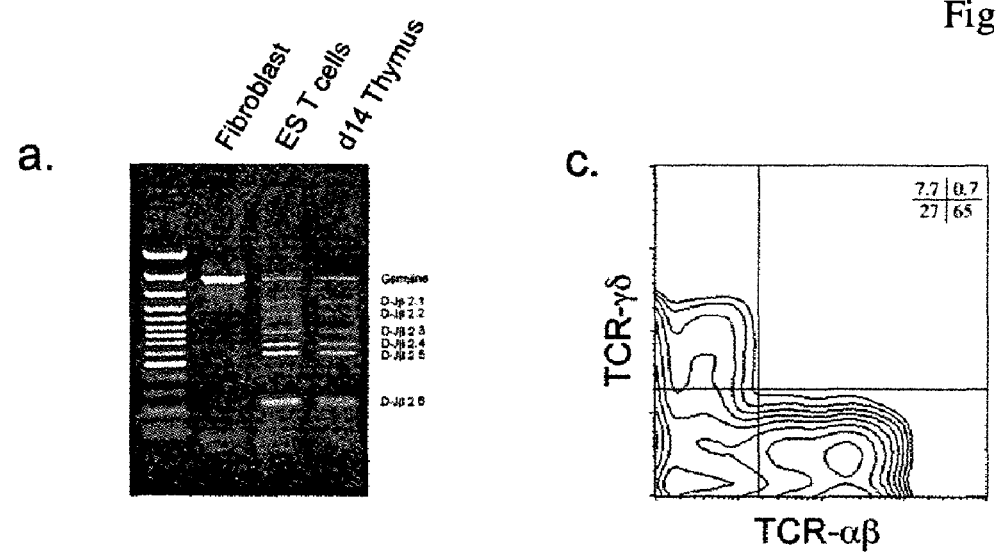
FIG. 12. ESC-derived T cell development recapitulates thymic development in-vitro. (a) ESC-derived T cells undergo multiple TCR-β D-J gene rearrangements. DNA was isolated from fibroblasts, CD25$^+$ CD44$^-$ ESC-derived T cells, and total day 14 fetal thymus and analyzed by PCR for rearrangements at the TCR-β locus. (b) ESCs cultured on OP9-DL1 give rise to T cells that display a diverse repertoire of T cell receptors. ESC-derived T cells were analyzed at day 20 for various TCR-Vβ gene products by flow cytometry. (c) ESCs give rise to both αβ- and γδ-T cells when differentiated on OP9-DL1 cells. ESCs were cultured on OP9-DL1 cells for 20 days, and the resulting cell population was analyzed for TCR-γδ and TCR-αβ expression by flow cytometry.
Figure 12:
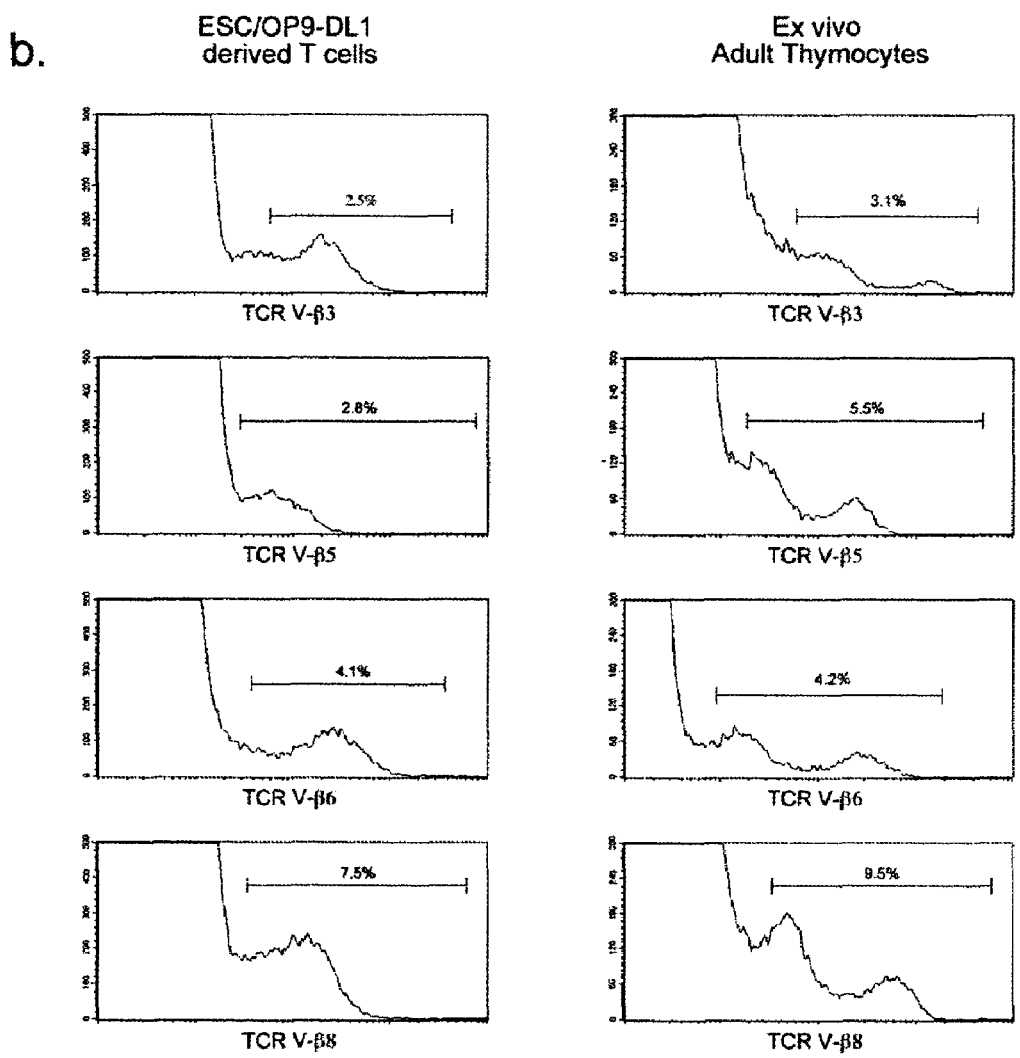

In order to determine whether the T cells that develop from ESCs cultured on OP9-DL1 cells undergo normal rearrangement of the TCR-β gene locus, we used PCR to analyze genomic DNA from CD44$^-$CD25$^+$DN progenitors from a day 12 ESC/OP9-DL1 culture. DNA from day 14 fetal thymus and from embryonic fibroblasts were also analyzed as rearranged and germline controls, respectively (FIG. 12a). The results presented in FIG. 12a demonstrate that ESC-derived T cells display a similar pattern of TCR-β gene rearrangement as ex vivo fetal thymocytes. Thus, ESCs cultured on OP9-DL1 cells give rise to a population of T cells containing a potentially diverse set of TCR gene rearrangements.

In order to correlate the diverse repertoire of TCR gene rearrangements observed by PCR analysis to the functional TCR-β gene product expressed at the cell surface, we analyzed ESC-derived T cells at day 21 of culture for surface expression of several commonly-used TCR Vβ gene segments by flow cytometry (FIG. 12b). When compared to ex vivo thymocytes, ESC-derived T cells displayed a similar pattern of TCR Vβ gene expression, indicating that the T cells that develop in this culture system have the potential to generate a diverse TCR repertoire.

During normal thymocyte development, both αβ- and γδ-TCR-bearing T cells develop in the thymus (Shortman and Wu, 1996). To determine whether both populations of T cells develop from ESCs cultured on OP9-DL1 cells, we analyzed ESC-derived T cells for the surface expression of αβ- and γδ-TCR. As illustrated in FIG. 12c, both populations of T cells developed from ESCs cultured on OP9-DL1.

Figure 11:
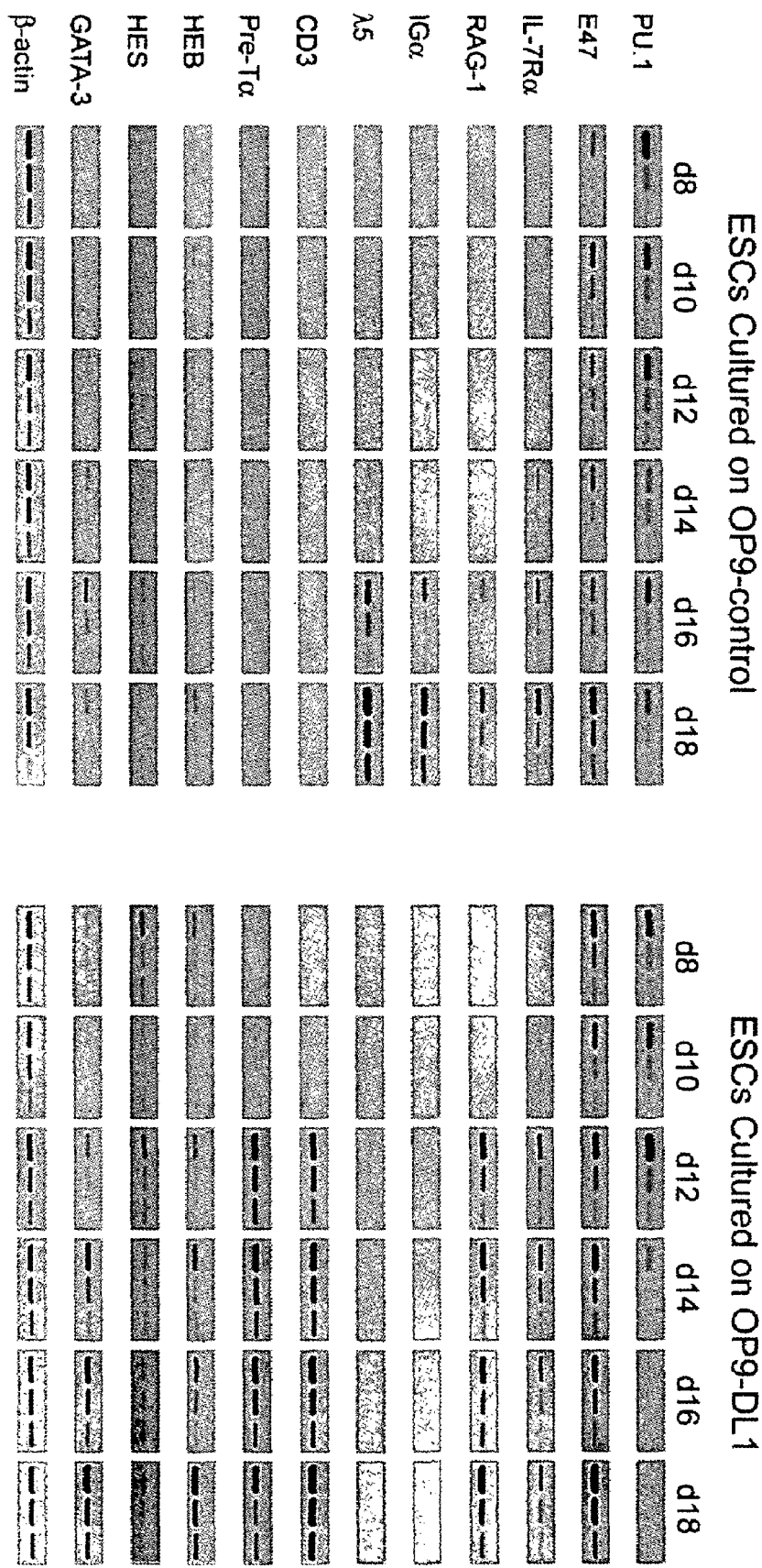
FIG. 11. Gene expression analysis of in vitro cultured ESCs. ESCs were cultured on OP9-control and OP9-DL1 cells and collected for analysis at multiple time points as indicated, mRNA was purified, and cDNA was generated. For each time point, 3 fold serial dilutions of the cDNA were normalized to β-actin, and then analyzed with gene-specific primers as indicated. These data are presented as inverted images of ethidium bromide stained gels.

Analysis of Hematopoietic and Lymphoid Lineage-specific Gene Expression During ESC Differentiation on OP9-control and OP9-DL1 Cells During hematopoietic development, HSCs undergo a program of sequential lineage restriction, which is thought to involve key transcriptional regulators that in turn mediate the coordinated expression of lineage-specific genes (Rothenberg et al., 1999). In order to elucidate at the molecular level the process by which ESCs differentiate on OP9 cells in the presence or absence of DL1, we assayed for the expression of developmentally-regulated genes over time by semi-quantitative RT-PCR analysis (FIG. 11). These data demonstrate that genes responsible for regulating hematopoiesis at multiple differentiation steps, such as the Ets protein, PU.1, and the E2A family member, E47, exhibit a dynamic pattern of expression throughout the time course. In particular, PU.1 is expressed throughout the ESC/OP9-control culture period, in keeping with its known role in regulating early myelopoiesis and B cell differentiation (Scott et al., 1994). In contrast, ESC/OP9-DL1 cultures display PU.1 transcripts only at early time points, consistent with the notion that PU.1 expression is important for the initiation of hematopoiesis, while down regulation of PU.1 expression is then required for proper T cell differentiation to proceed (Anderson et al., 2002). Of note, E47, which is known to be involved in both B and T cell differentiation (Engel et al., 2001; Zhuang et al., 1994; Bain et al., 1994) is expressed throughout the culture period on both stromal cell lines.

We also analyzed for the expression of IL-7Rα(Peshon et al., 1994) and RAG-1 (Mombaerts et al., 1992) genes, which are required for the survival and proliferation of lymphocyte progenitors, as well as for both B cell and T cell antigen receptor gene rearrangement, respectively (FIG. 11). In this regard, both IL-7Rα and RAG-1 transcripts are detected at time points when B- and T-lymphopoiesis first become apparent by flow cytometry (FIG. 9a).

The results presented in FIG. 9 demonstrate that expression of DL1 by OP9 cells fundamentally changed the stromal environment from one that strongly induces B cell development to one that efficiently supports all aspects of T cell development, consistent with the role of Notch signaling in the regulation of B/T lineage commitment. To address whether the different programs of B and T cell gene expression are tightly and coordinately regulated under these culture conditions, several B and T cell-specific genes were analyzed. Transcripts for λ5 and Igα, which are part of the pre-BCR complex and are expressed during early B cell development, are only detected in cells from ESC/OP9-control cultures (FIG. 11). Notably, CD3ε and pre-Tα transcripts, which are part of the pre-TCR complex and expressed during early T cell development, are only expressed in cells from the ESC/OP9-DL1 cultures. These data indicate that the induction of lineage-specific gene expression in differentiating ESCs is indeed appropriately coordinated under these culture conditions. Thus, the temporal kinetics of this regulated gene expression serves as a clear indication as to when B- and T-lineage commitment first occurs within the ESC/OP9-control and ESC/OP9-DL1 cultures, respectively.

We also examined whether the expression of lineage-specific genes correlated with the presence of transcription factors known to play an important role during T cell development, such as HEB (Barndt et al., 2000), HES-1 (Tomita et al., 1999), and GATA-3 (Ting et al., 1996) (FIG. 11). The basic helix-loop-helix (bHLH) transcription factor HEB, which is essential for the transition from the DN to DP stage (Barndt et al., 2000), was found to be highly expressed at later time points in the ESC/OP9-DL1 cultures. HES-1, a bHLH transcription factor and transcriptional repressor that is induced downstream of Notch signaling, was expressed at all time points analyzed in cells from the ESC/OP9-DL1 cultures. Moreover, HES-1 transcripts were detected, albeit at lower levels, in ESCs cultured on the OP9-control cells. The presence of HES-1 transcripts in ESC/OP9-control cultures is likely due to the expression by OP9 cells of Jagged-1 and-2 (Schmitt et al., 2002). GATA-3, a zinc-finger transcription factor, which is expressed by all developing T cells and is essential for their generation (Ting et al., 1996), was found to be expressed throughout the culture period and at high levels after day 12 in the ESC/OP9-DL1 cultures.

Example 6

Efficient Generation of T Cells from FL-derived HPCs Cultured on OP9-DL1 Cells

Experimental Procedure:

Precursor frequency analysis: Limiting dilution analysis was performed by obtaining serial dilutions from day 14 FL cells, sorted as CD117$^+$ Sca1$^{hi}$ CD24$^{lo}$/Lin$^-$ expressing cells. The cells were sorted using the Clonecyte option of the FACSDiVa cell sorter, in which precisely 1, 3, 10, or 30 cells were deposited onto OP9-GPF cells or OP9-DL1 cell monolayers in 96-well plates, with 36 replicate wells for each sample group. The cells were placed in culture for 12 days, after which cells were harvested from individual wells, and analyzed by flow cytometry. The presence of CD4$^+$, CD8$^+$, CD19$^+$, or CD11b$^+$ cells was scored and the progenitor frequency was determined by the method of maximum likelihood applied to the Poisson model (Fazekas de St, 1982). Cocultures were observed under an inverted microscope, in some cases total cellularity was determined by cell counting, and analyzed by flow cytometry from wells that were seeded with a single HPC to determine approximate clone size.

Results

Figure 7:
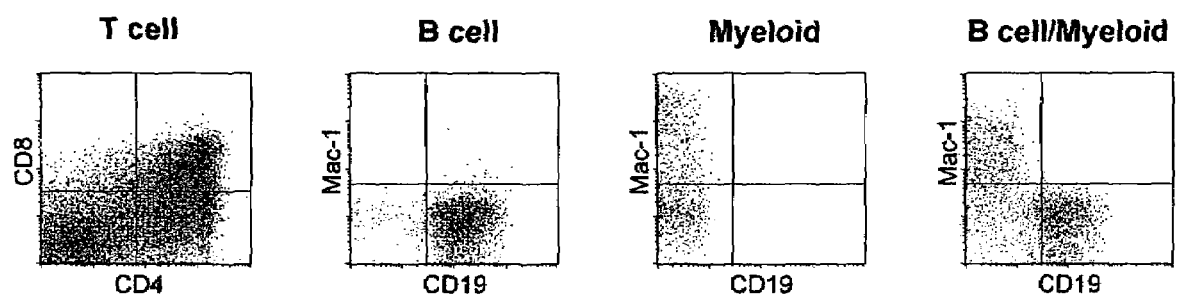
FIG. 7. Representative lineage profiles from the HPC limiting dilution analysis. The progenitor potential of sorted HPCs cultured on OP9-GFP cells or OP9-DL1 cells was determined based on the following criteria: T cells were characterized as CD4$^+$ CD8$^+$; B cells as CD 19$^+$ CD11b$^-$; and myeloid lineage cells as CD19$^-$ CD11b$^+$. Many wells contained both CD19$^+$ CD11b$^-$ and CD19$^-$ CD11b$^+$ cells, these wells were counted as positive for both the B cell and myeloid lineages. The CD4 versus CD8 flow cytometric analysis shown above represents cells derived from the seeding of a single (1 cell/well) sorted HPC onto OP9-DL1 cells.

To determine the frequency of progenitors present within the FL-derived HPC population that, when cultured on OP9-DL1 cells, could give rise to T cells, a limiting dilution analysis was performed. The progenitor frequency for B cells and myeloid cells was also determined from HPCs cultured on control OP9 cells. Table 2 shows the progenitor frequencies obtained from 1, 3, 10, or 30 HPCs (n=36 per group) cultured on OP9-GFP or OP9-DL1 cells for 12 days, and then analyzed by flow cytometry for the presence of B and myeloid cells or T cells, respectively (FIG. 7). The presence of DP T cells was used as evidence for T cell progenitor potential within individually harvested wells (FIG. 7). The progenitor frequency of HPCs that can give rise to T cells was determined by the method of maximum likelihood and calculated to be about 1 in 17 HPCs. This progenitor frequency is inconsistent with the possibility that the observed T cells were derived from an extremely rare population of T cell lineage-committed pro-T cells that may exist within the HPC fraction (Kawamoto et al., 1999). The observed T cell progenitor frequency from HPCs was ~3 fold lower than that obtained for B cells, which was determined to be about 1 in 6 HPCs (Table 2). The myeloid progenitor frequency was about 1 in 5 HPCs, which resembles the frequency of true multipotent hematopoietic progenitor cells observed by others within the FL CD117$^+$ Sca-1$^{hi}$ fraction (Kawamoto et al., 1999). Taken together, these results indicate that T cell lineage commitment occurs with high efficiency from FL-derived HPCs cultured on OP9-DL1 cells.

Example 7

Figure 6:
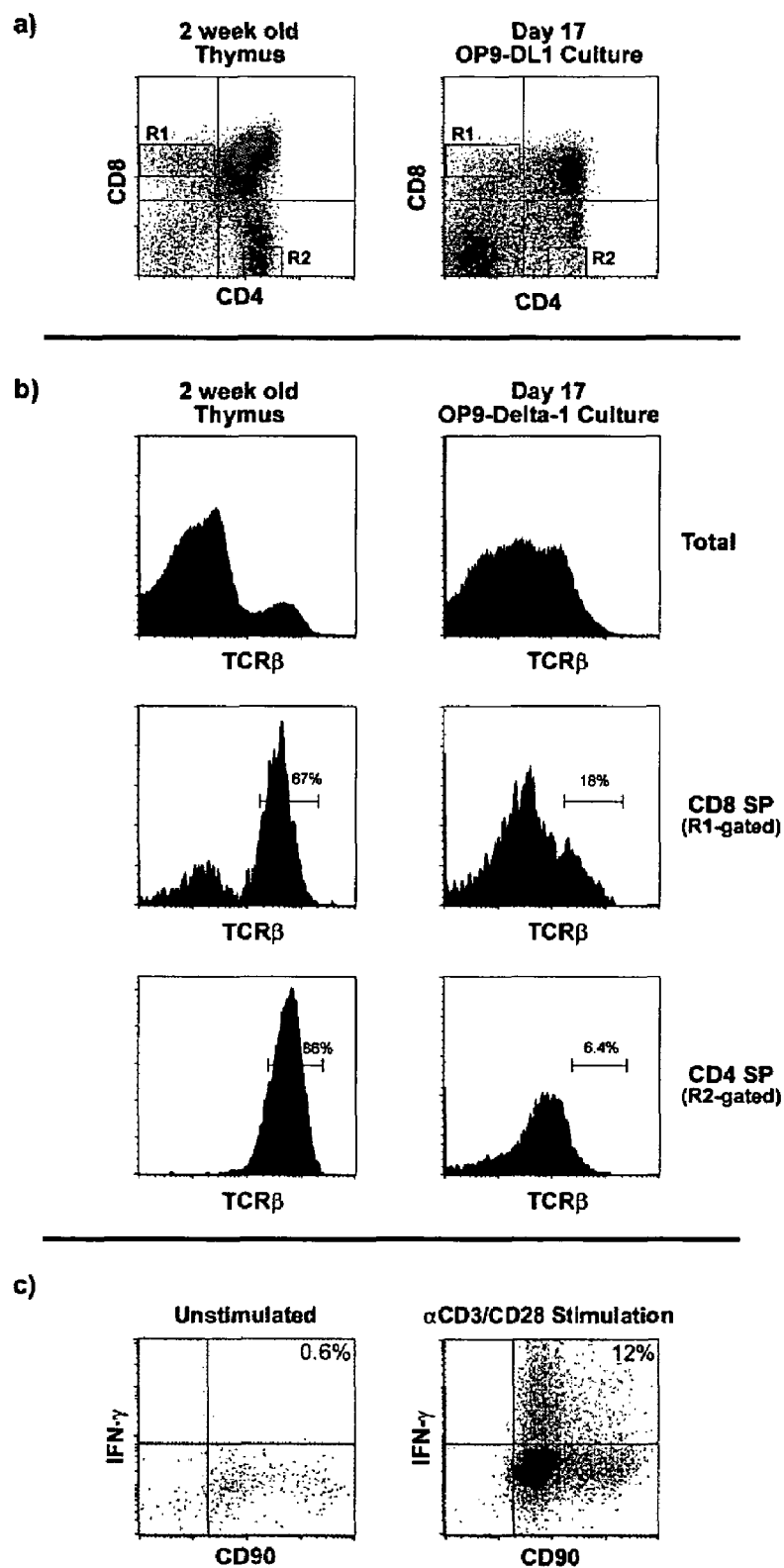
FIG. 6. Generation of functionally mature T cells from HPCs cultured on OP9-DL1 cells. a, Flow cytometric analysis for CD4 and CD8 expression from day 17 HPC/OP9-DL1 cocultures or thymocytes obtained from a 2 week old mouse. b, Flow cytometric analysis for TCRβ surface expression from total day 17 HPC/OP9-DL1 cocultures or total thymocytes, and from CD8 SP (R1-gated) or CD4 SP (R2-gated) cells, using the region gates indicated in the top panel. The mean fluorescence intensity of TCR staining for cells within the indicated histogram markers from thymocytes or HPC/OP9-DL1 cocultured cells were: CD8 SP, 444 and 388; and CD4 SP, 663 and 372, respectively. c, CD4$^-$ CD8$^+$ CD3$^{high}$ cells were sorted from day 14 HPC/OP9-DL1 cocultures and stimulated by plate-bound anti-CD3 and anti-CD28 mAbs. Production of γ-interferon(IFN-γ) was determined by intracellular staining followed by flow cytometric analysis.

Generation of Functionally Mature T Cells on OP9-DL1 Cells HPC-derived T Cell Cultures Contain Mature T Cells Although the majority of T lineage cells generated from HPC/OP9-DL1 cocultures corresponded to immature DP T cells, a small percentage of SP T cells were present in day 12 cocultures (FIG. 3b) and at later time points (FIG. 6a). In order to determine whether these cells represented DPs that had differentiated to the next stage of T cell development, SP T cells present in day 17 HPC/OP9-DL1 cocultures were compared to thymocytes obtained from a 2 week old mouse (FIG. 6a). FIG. 6b shows that ~18% of the CD8 SP T cells from these cocultures expressed surface TCR levels similar to those observed on CD8 SP thymocytes. On the other hand, CD4 SP cells obtained from these cocultures did not express surface TCR at levels that were similar to those observed on CD4 SP thymocytes (FIG. 6b).

The observation that some CD8 SP T cells expressed high levels of TCR on their surface suggested that these cells might have reached functional maturity. To address this intriguing possibility, CD4⁻ CD8⁺ TCR$^{hi}$ cells were isolated by flow cytometric cell sorting and their response to plate-bound antibodies specific for CD3 and CD28 was determined (FIG. 6c). The stimulated CD8⁺ T cells, but not the unstimulated controls, underwent a burst of activation-induced proliferation and γ-interferon production, as detected by flow cytometric analysis (FIG. 6c). These data demonstrate that expression of Delta-like-1 by OP9 cells is able to support the differentiation of FL-derived HPCs into mature and functional T cells in vitro.

ESC-derived T Cell Cultures Contain Mature Functional Single Positive T Cells

Figure 13:
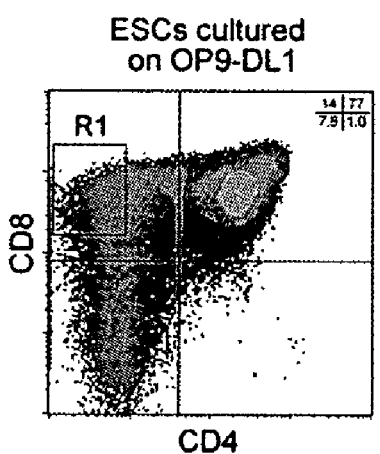
FIG. 13. Functionally mature CD8+ T cells develop from ESCs cultured on OP9DL1. (a) single positive T cells with high levels of TCR-β are generated from ESCs cultured on OP9-DL1. ESCs were cultured on OP9-DL1 cells for 22 days, and then analyzed by flow cytometry. (b) CD8+ TCR-β$^{hi}$ T cells were purified from day 22 ESC/OP9-DL1 cultures and then stimulated for 3 days with plate-bound anti-CD3 and anti-CD28 (10 ug/ml each), or without stimulation.
Figure 13:
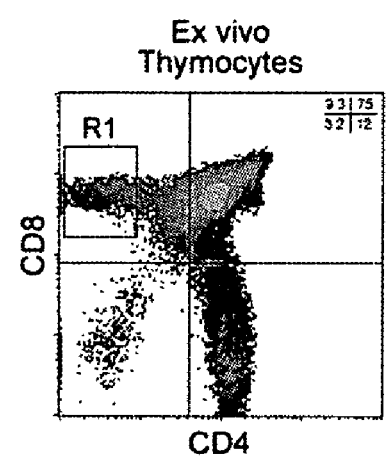
Figure 13:
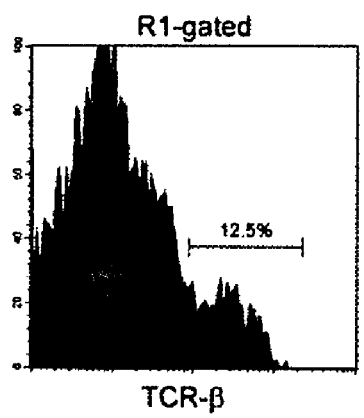
Figure 13:
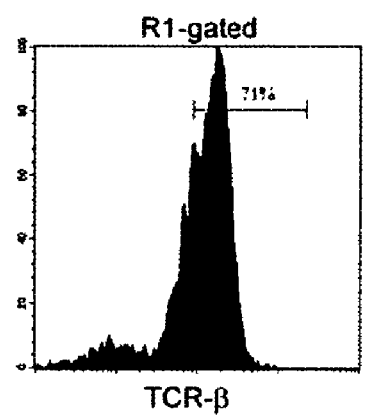
Figure 13:
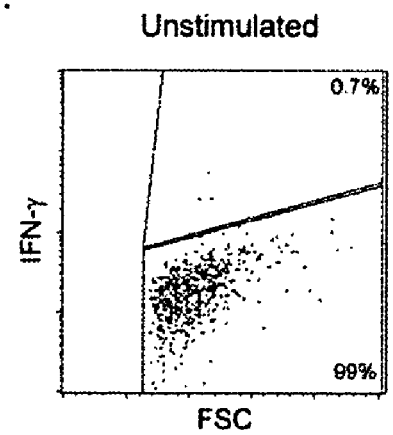
Figure 13:
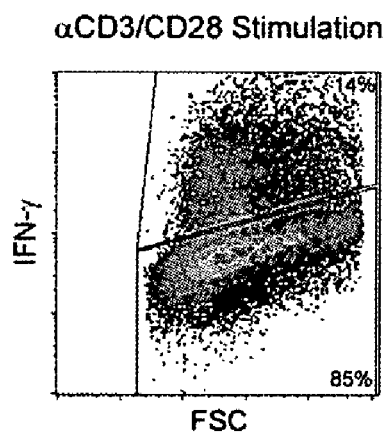

To determine whether ESC cultures contained mature CD4 or CD8 single positive (SP) T cells, we analyzed day 22 ESC/OP9-DL1 cultures (FIG. 13a), which revealed the presence of CD8 SP and DP T cells but not CD4 SP T cells. For comparison, we also analyzed the expression of CD4 and CD8 on thymocytes from an adult mouse, which exhibited a typical CD4 and CD8 expression pattern. TCR surface expression normally increases following thymocyte maturation from the DP to the SP stage. As shown in FIG. 13a, a subset of CD8 SP T cells from day 22 ESC/OP9-DL1 cultures displayed high levels of TCR staining similar to that of ex vivo CD8 SP thymocytes.

To address whether the CD8 SP T cells expressing high levels of TCR were indeed functionally mature, CD4⁻ CD8⁺ TCR$^{hi}$ cells derived from ESCs were purified by cell sorting and cultured for three days in the presence or absence of plate-bound anti-CD3 and anti-CD28 antibodies. FIG. 13b shows that ESC-derived CD8 SP T cells proliferate, and produce interferon-γ in response to TCR engagement. Therefore, ESCs cultured on OP9-DL1 can fully differentiate into mature functional SP T cells that exhibit high levels of TCR surface expression, undergo robust proliferation and produce interferon-γ in response to antigen receptor stimulation.

Example 8

Induction of T Cell Development and Efficient immune Reconstitution of T Cell Effector Function from Embryonic Stem Cell (ESC)/OP9-DL1 cell Coculture-derived T Cell Progenitors Experimental Procedure:

Fetal thymic organ culture: Lymphocyte depleted fetal thymic lobes were prepared by culturing the thymic lobes from C57/B16(CD45.1) day 15 embryos in medium containing 1.25 mM deoxyguanosine for 5 days as previously described. CD25⁺ CD45⁺ ESC-derived T cell progenitors (CD45.2⁺) were purified by flow cytometric cell sorting from day 11-12 ESC/OP9-DL1 cultures and 1×10⁴ cells were seeded into each pair of lymphocyte depleted thymic lobes and cultured for 14 days.

Adoptive transfer of ESC reconstituted lobes: Fetal thymic lobes were reconstituted with ESC-derived T cell progenitors as described above and cultured in vitro for 6 days, followed by adoptive transfer under the skin of Rag2$^{-/-}$ recipient mice. After 3 weeks, the host animals were sacrificed, and the spleen and lymph nodes were analyzed for ESC-derived T cells by flow cytometry (ESC-derived T cells expressed CD45.2 and TCR-β). LCMV challenge, and Cytotoxicity Assay: RAG2$^{-/-}$ mice were reconstituted with ESC-derived T cell progenitors as described above, except that fetal thymic lobes from RAG2$^{-/-}$ mice fetuses were used. Two weeks after reconstitution, recipient mice and wild-type B6 control mice were infected i.v. with 2000 PFU LCMV. 8 days after infection, splenocytes were isolated, and the cytolytic activity of ESC-derived T cells was determined in a $^{51}$Cr-release assay. EL4 target cells were coated with the LCMV glycoprotein peptide gp33 or a control adenovirus-derived peptide (AV) at a concentration of 1 μM and labeled with $^{51}$Cr for 1.5 hour. After washing, 10⁴ target cells were mixed with ESC-derived T cells from reconstituted RAG2$^{-/-}$ animals at ratios of 90:1, 30:1, 10:1, and 3:1 in 96 well round-bottom plates. Cells were incubated for 5 hours, and then supernatants were analyzed for $^{51}$Cr release associated with cytolytic activity.

Results

Figure 14:
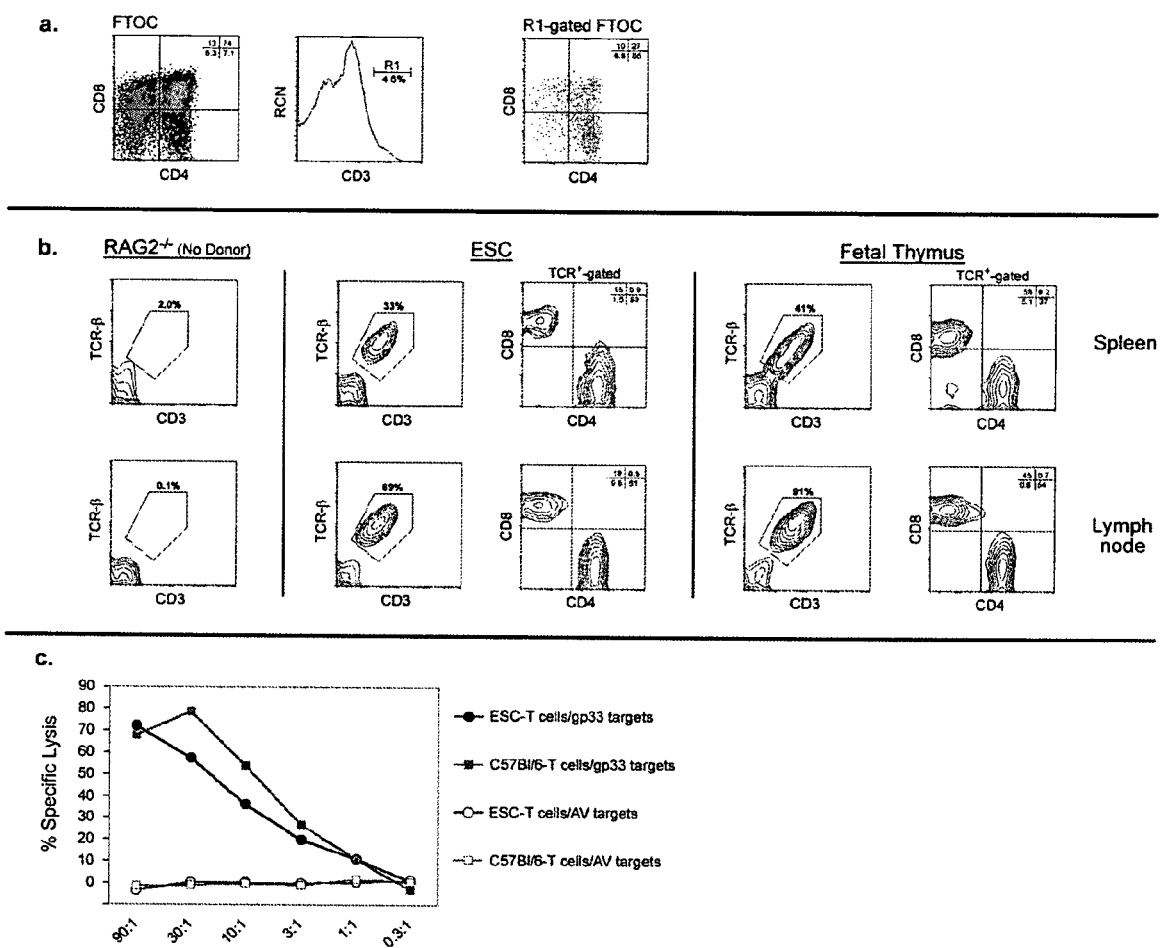
FIG. 14. ESC-derived T cells can reconstitute immune function in immunodeficient hosts. (a) ESC-derived T cell progenitors can reconstitute fetal thymic organ culture (FTOC). $10 \times 10^4$ CD45.2+ CD25+ ESC-derived T cell progenitors were seeded into CD45.1 congenic, deoxyguanosine-treated fetal thymic lobes, and cultured for 10 days. Only T cells of donor origin (CD45.2) were observed. (b) ESC-derived T cell progenitors can reconstitute an immune-deficient host. ESC-derived T cell progenitors were seeded into day 14 fetal thymic lobes from CD45 congenic B6 mice and cultured in FTOC. After 5 days, the reconstituted fetal thymic lobes, or non-depleted fetal thymic lobes, were implanted under the skin of RAG2 deficient mice. After 3 weeks, the spleen and lymph nodes of recipient mice (center and right panels), as well as those of an unmanipulated RAG2$^{-/-}$ mouse (left panel), were analyzed by flow cytometry for TCR-β+ donor-derived T cells as indicated. (c) Adoptively transferred ESC-derived T cells can mount an antigen specific CTL response. ESC-derived T cell progenitors were cultured in FTOC for 5 days in fetal thymic lobes from RAG2$^{-/-}$ mice. After 5 days, the reconstituted lobes were implanted under the skin of RAG2$^{-/-}$ mice. Two weeks after transfer, recipient mice and wild-type B6 control mice were infected i.v. with 2000 PFU LCMV. 8 days after infection, splenocytes were isolated, and assayed for CTL activity by $^{51}$Cr-release assay using EL4 target cells pre-pulsed with $^{51}$Cr and the LCMV glycoprotein gp33 or a control adenovirus-derived peptide (AV) as indicated.

Although ESCs have enormous theoretical potential as an efficient and effective source of transplantable tissue-specific progenitor cells, experimentally this potential has not yet been demonstrated using genetically unmodified ESCs (Orkin and Morrison., 2002). In order to determine whether ESC-derived T cell progenitors could differentiate normally after transfer into an intact thymic microenvironment, we isolated CD25⁺ CD44$^{+/-}$ DN T cell progenitors (CD45.2) by flow cytometric cell sorting from a day 12 ESC/OP9-DL1 culture. These cells were then used to seed CD45.1-congenic deoxyguanosine-treated fetal thymic organ cultures (FTOC), which were analyzed by flow cytometry after 10 days in culture. FIG. 14a demonstrates that CD25⁺ DN T cell progenitors obtained from a d12 ESC/OP9-DL1 culture are indeed capable of developing in FTOC, and generate both CD4 CD8 DP, and TCR$^{hi}$ CD4 and CD8 SP T cells.

These results showing that ESC-derived T cell progenitors can readily reconstitute and develop normally in FTOC, allowed us to address whether implantation of in vitro-reconstituted FTOCs might provide the means by which differentiated ESCs could be introduced into an adult host animal. Therefore, CD25⁺ CD44$^{+/-}$ DN T cell progenitors, obtained from a 2 week ESC/OP9-DL1 culture (see FIG. 9a), were transferred into CD45.1-congenic fetal thymic lobes and placed in culture for 5 days. These reconstituted thymic lobes were then implanted under the skin of sublethally-irradiated RAG2$^{-/-}$ mice. Three weeks after implantation, the spleen and lymph nodes of the reconstituted mice were analyzed by flow cytometry for the presence of TCR⁺ CD45.2⁺ donor-derived T cells (FIG. 14b). As expected, non-grafted RAG2$^{-/-}$ mice were devoid of TCR/CD3-bearing CD4⁺ or CD8⁺ T cells. In striking contrast, RAG2$^{-/-}$ mice implanted with FTOCs seeded with ESC-derived T cell progenitors showed a robust reconstitution with both TCR/CD3⁺ CD4 and TCR/CD3⁺ CD8 SP T cells present in the spleen and lymph nodes. Notably, the efficiency and effectiveness of T cell reconstitution with ESC-derived T cell progenitors was comparable to that observed in RAG2$^{-/-}$ mice implanted with control untreated fetal thymic lobes (FIG. 14b). Thus, these results clearly demonstrate that ESCs induced to adopt a T lineage fate on OP9-DL1 cells are fully capable of reconstituting the T cell compartment of a host animal.

To directly test whether the RAG2$^{-/-}$ mice that had been reconstituted with ESC/OP9-DL1-derived T cell progenitors could in fact mount a functional immune response, we infected these mice with the lymphocytic choriomeningitis virus (LCMV). After 8 days, splenocytes were recovered and assayed for LCMV-specific cytotoxic T lymphocyte (CTL) activity in vitro. FIG. 14c shows that ESC-derived T cells were indeed capable of generating an effective antigen-specific immune response following LCMV infection. Moreover, the LCMV-specific CTL response detected from RAG2$^{-/-}$ mice reconstituted with ESC-derived T cells was equivalent to that observed from normal C57BL/6 mice. It is important to note that in these experiments, the fetal thymic lobes that were seeded with the ESC-derived T cell progenitors were also RAG2-deficient, ensuring that any TCR-bearing cells present in the reconstituted RAG2$^{-/-}$ mice could only be ESC/OP9-DL1-derived.

Example 9

Induction of T Cell Differentiation from Human-cord Blood-derived Stem Cells Cultured on OP9-DL1 Cells Experimental Procedures Cord Blood Cells: Collection, Cryopreservation, and Separation: Human cord blood samples (approximately 50 ml/sample) were obtained by syringe extraction and collected in heparinized tubes from consenting mothers following birth on the delivery floor of the Women's College Ambulatory Care Centre in accordance to the guidelines established by the Institutional Review Board at Sunnybrook & Women's Health Sciences Center (Toronto, ON Canada). Cord blood obtained within 6 hours were separated by Ficoll-Hypaque (1.070 g/cm$^3$) density gradient centrifugation into a low density (<1.070 g/cm$^3$) mononuclear cell fraction, which was subsequently washed 3 times with Hank's Balance Salt Solution (Sigma) and then frozen in 10% dimetyl sulfoxide (DMSO)+90% fetal bovine serum (FBS) for later use. Debulked frozen cord blood was thawed and washed twice with HBSS, and human hematopoietic progenitors were enriched utilizing the StemSep human CD34 positive selection cocktail (Stem Cell Technologies, Vancouver, BC, Canada) and then separated into CD34-positive and CD34-negative fractions on an autoMACS machine (Miltenyl Biotec, Auburn Calif.). The CD34-positive fraction underwent a second passage on the autoMACS and aliquots of both the positive and negative fractions were saved to determine fold enrichment. Human CD34$^+$ cells underwent a >70× enrichment from pre-sorted to post-sorted CD34-positive fraction (1.2% +/−3.8 to 85.4% +/−12.6 respectively). To further isolate the primitive hematopoietic cells from autoMACS-sorted cord blood, the CD34-positive fraction was blocked with anti-human CD32 (FcRII) antibody (Stem Cell Technologies, Vancouver, BC, Canada) and stained with allophycocyanin (APC)-conjugated anti-CD38 (clone HIT2) and subsequently sorted for CD34$^+$CD38$^-$ cells utilizing a Coulter Elite cytometer (Hialeah, Fla.); sorted cells were >99% pure, as determined by post-sort analysis.

Human hematopoietic progenitor and OP9 stroma cell coculture: 10×10$^3$, 5×10$^3$, or 2.5×10$^3$ sorted human hematopoietic progenitors CD34$^+$ CD38$^-$ cells were added per individual well of a 6 well plate confluent with either OP9-DL1 cells or OP9-control cells in αMEM media supplemented with 20% coculture characterized FBS +1% penicillin/streptamyicin. Recombinant human cytokines Flt3-L (5 ng/ml) and IL-7 (5 ng/ml) (Peprotech, Rocky Hill, N.J.) were added to the coculture. Cocultures were disaggregated by vigorous pipetting and passaged through a 70 μm filter to reduce stromal cell line aggregates. Each experiment was repeated at least three times with similar results with the results being presented as a representative histogram.

Flow Cytometry: Fluorescein isothiocyanate (FITC)-, R-Phycoerythrin (PE)-, allophycocyanin (APC)-, biotin-conjugated antibodies and streptavidin-allophycocyanin (SAv-APC) were all obtained from PharMingen, BD Biosciences (San Diego, Calif.). Cell suspensions obtained from cocultures were FcRII blocked, stained in the dark in 50 μl FACS buffer (HBSS without phenol red, plus 1% BSA and 0.05% NaN$_3$) for 20 minutes on ice and washed twice before analysis. Stained cells were analyzed with a FACSCalibur flow cytometer using FlowJo software (FlowJo); data were live-gated by forward/side light scatter and lack of propidium iodide uptake. GFP-expressing OP9 stromal cells were gated out of the analysis through FITC expression by side scatter exclusion. Frequencies in quadrant corners are given as percent of gated cells.

Results

Generation of the T Cells from Human CD34$^+$ CD38$^-$ Cord Blood Cells Cultured with OP9 Cells Expressing Delta-like-1

Figure 15:
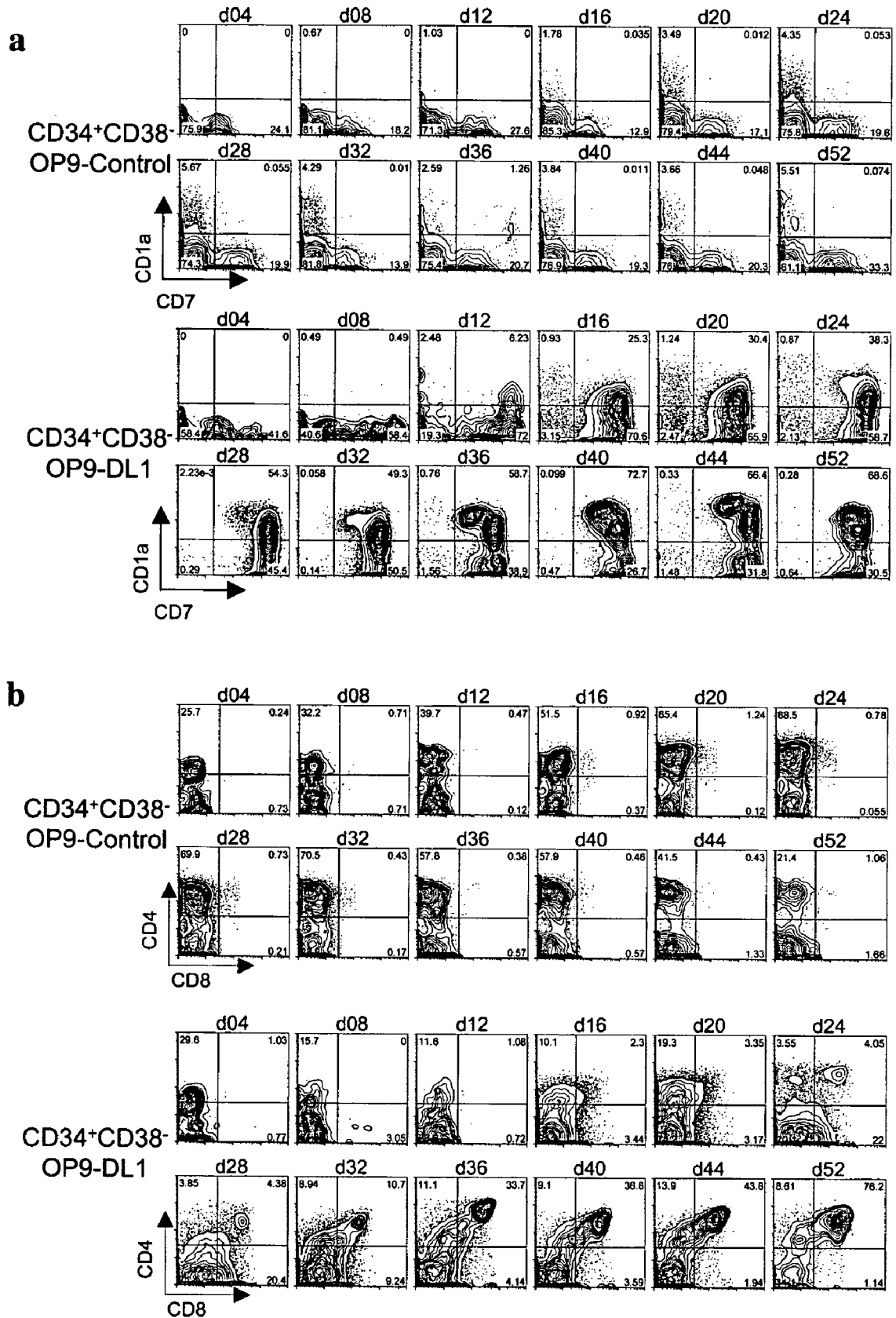
FIG. 15. Lineage commitment and differentiation of human-cordblood-derived HPCs cultured on OP9-DL1 cells. (a) Flow cytometric analysis of the temporal kinetics of the expression of CD7 and CD1a on differentiating human cord blood progenitors CD34+ CD38− cocultured with OP9-control cells (top two rows) or OP9-DL1 cells (bottom two rows). (b) Flow cytometric analysis of the temporal kinetics of the expression of CD8 and CD4 on differentiating human cord blood progenitors CD34+ CD38− cocultured with OP9-control cells (top two rows) or OP9-DL1 cells(bottom two rows).

Human T cell development occurs in the thymus through a series of discrete steps that are similar to those observed in mice. Although human T cells mature through a CD4 CD8 DP stage before preceding to either the CD4 SP or CD8 SP stage. In humans the CD4$^-$ CD8$^-$ stage can be further examined by the surface expression of CD1a and CD7. In addition, while T cell development in mice proceeds to the CD4 CD8 DP stage via a CD8 ISP stage, T cell development in humans proceeds towards the DP stage via a CD4 ISP stage. To determine the differentiation potential of human HSCs obtained from human umbilical cord blood (CB) to give rise to T lymphocytes, sorted CD34$^+$ CD38$^-$ Lin$^-$ CB cells were cultured on OP9-DL1 cells, and the expression of T cell lineage markers (CD1a/CD7 and CD4/8) was examined by flow cytometry at different time points. As seen in FIG. 15 CD34$^+$ CD38$^-$ CB cells cultured on OP9-DL1, but not OP9-GFP/control, stromal cells lead to a rapid emergence of pre-T1 cells (CD7$^{++}$ CD1a$^+$) by day 12 of coculture and later DP T cells (CD4$^+$ CD8$^+$) by day 24 of coculture (FIGS. 15A and B). By day 28 of coculture on OP9-DL1, a second population (CD7$^+$ CD1a$^+$) of cells expressing lower levels of CD7 emerged (FIG. 15A), and is consistent with the maturation of pre-T1 cells into DP cells (FIG. 15B). As the coculture progressed by day 52, DP T cells dominated the coculture accounting for 76% of the total cells. This percentage is consistent with the percentage observed in cocultures with mouse ESCs on OP9-DL1, mouse progenitor cells in FTOCs, and the DP population found in vivo in the thymus. Intriguingly, few CD4 and CD8 SP cells were generated, likely due in part to the absence of thymic epithelial cells expressing human MHC II and MHC I molecules, respectively.

Discussion

Notch is responsible for multiple binary cell fate decisions in the developing embryo, and Notch signals regulate both proliferative and apoptotic events in a cell-context dependent manner (Artavanis-Tsakonas et al., 1999). Notch receptor/ligand interactions have been implicated in governing the commitment of common lymphoid progenitors (CLPs) to the T cell lineage at the expense of B lineage development (Koch et al., 2001; Pui et al., 1999; Radtke et al., 1999). It is demonstrated that OP9 cells expressing Notch ligands induce the commitment of FL-derived HPCs, BM-derived HSCs, human-cord blood-derived HSCs or ESCs towards the T cell lineage while subverting their ability to support B cell lymphopoiesis. This likely occurs at a CLP-like intermediate stage during the coculture period. The fact that NK cells develop from HPCs regardless of the expression of Delta-like-1 by OP9 cells suggests that commitment of CLPs to the NK cell lineage is not predicated by the Notch-mediated T/B cell fate determination.

The results demonstrate that FL-derived HPCs differentiate into T cells with a high efficiency (1 in 17 HPCs) when cultured on Delta-like-1-expressing OP9 cells. This high progenitor frequency supports the notion that the resulting T cells are derived from multipotent progenitors or CLPs induced to adopt a T cell lineage fate, rather than from a rare subset of precommitted T cell progenitors that might be present within the HPC fraction (Kawamoto et al., 1999). Moreover, not only did T cell lineage commitment occur at a high frequency, but it was also accompanied by high cellular yields due to the robust proliferative potential of the differentiating HPCs. This is highlighted by the fact that after 12 days of coculture a cellular expansion of $\geq 2,000$ fold was routinely observed. Interestingly, despite the fact that the B cell progenitor frequency of HPCs was 3 fold higher (1 in 6 HPCs), the cellular expansion observed for T lineage cells generated from HPCs cultured on OP9-DL1 cells was about 3 fold higher than that of B cells obtained from OP9-GFP cocultures.

Figure 8:
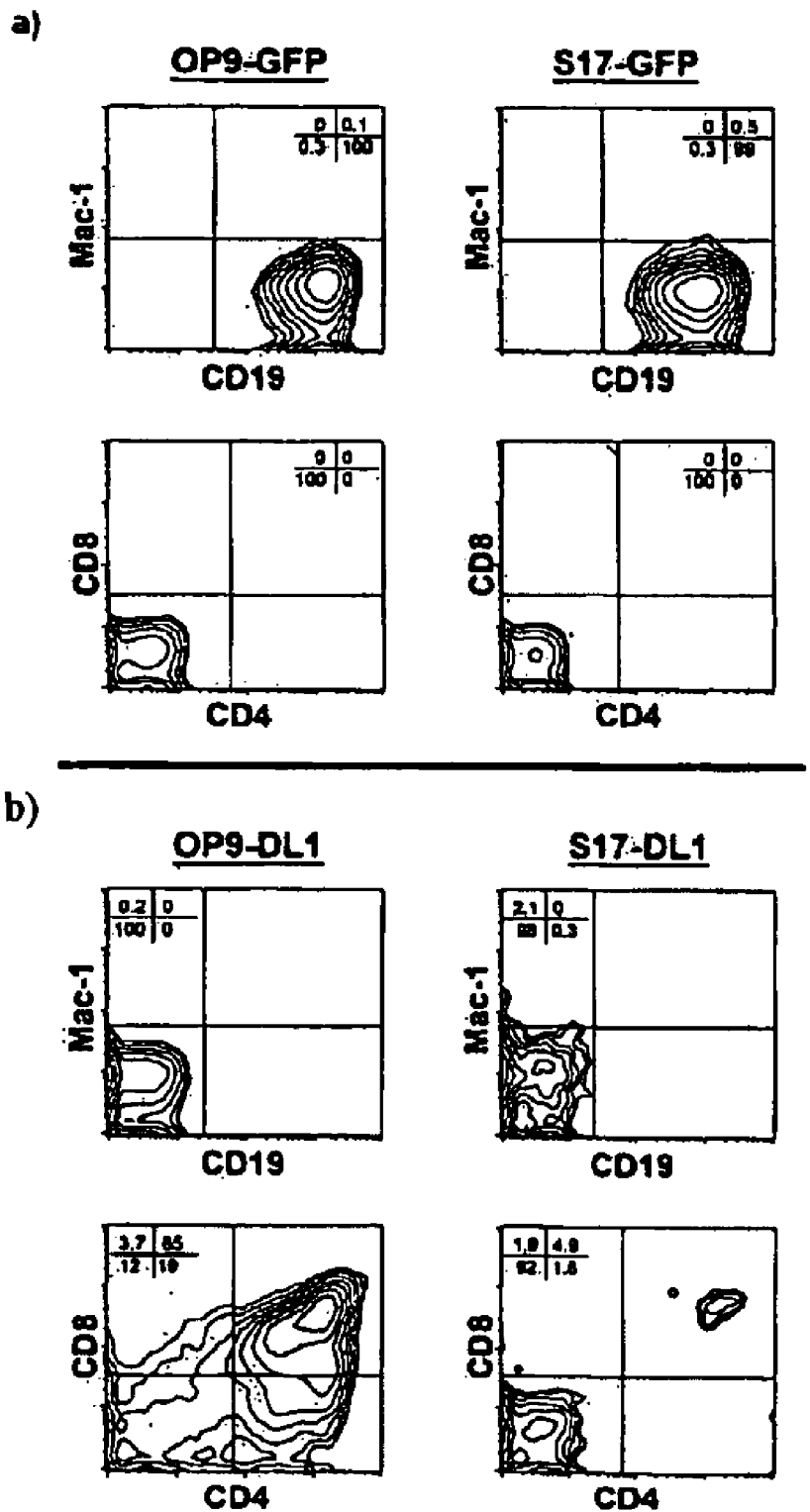
FIG. 8. Comparison of the induction of T cell development from HPCs cultured on either OP9 or S17 bone marrow stromal cells ectopically expressing Delta-like-1. Sorted HPCs (4×10$^3$ cell/well) were cultured for 12 days on (a) OP9-GFP cells or S17-GFP cells, and (b) on OP9-DL1 cells, or S17-DL1 cells. Cocultures were harvested and analyzed by flow cytometry for the indicated cell surface markers.

The findings suggest that the differentiation requirements for B cell and T cell lymphopoiesis are remarkably similar. This is illustrated by the fact that the expression of one additional molecule, Delta-like-1, switches the ability of a stromal environment that otherwise strongly supports B cell differentiation to now induce and support the full development of T cells from FL HPCs, as well as from adult bone marrow-derived HPCs. A similar approach was recently described by Jaleco et al., in which a different bone marrow stroma cell line, S17 (Collins and Dorshkind, 1987), was transduced to express Delta-like-1 (Jaleco et al., 2001). S17 cells expressing Delta-like-1 lost the ability to induce B lymphopoiesis from human-derived CD34$^+$ hematopoietic progenitors. However, Delta-like-1-expressing S17 cells only promoted the emergence of a cell population that resembled T/NK progenitors. In contrast to the results described herein using OP9-DL1 cells, no clear evidence for T cell lineage commitment or further T cell development was reported (Jaleco et al., 2001). Several factors could explain the observed differences: human progenitors may be unable to differentiate into T cells on a mouse stroma cell line; or, on the other hand, S17 cells may not provide the appropriate microenvironment for efficient Delta-like-1-mediated T cell development. To address the latter possibility, S17 cells expressing Delta-like-1 (S17-DL1) were generated, and compared to OP9-DL1 cells for the ability to induce and support T cell development from HPCs (FIG. 8). Although B cells were generated with equal efficiency from HPCs cultured on control OP9-GFP or S17-GFP cells, there was a marked difference in the generation of T cells on S17-DL1 cells (~5% DP cells) as compared to OP9-DL1 cells (~65% DP cells). Furthermore, HPCs cultured on S17-DL1 cells displayed little proliferative potential during the culture period, similar to the limited growth potential observed with human progenitors cultured on S17 cells expressing Delta-like-1 (Jaleco et al., 2001). The cocultures include the addition of exogenous cytokines (Flt3L and IL-7), which may account for the moderate generation of T cells on S17-DL1 cells (FIG. 8), as opposed to the cocultures with human CD34+ cells, which did not receive exogenous cytokines (Jaleco et al., 2001). Therefore, OP9 cells provide a more appropriate stromal environment for Delta-like-1 to mediate the induction of T cell lineage commitment and differentiation than S17 cells, which may lack important factors and/or express negative modulators of Notch receptor or Notch ligand function, such as Fringe or Neuralized, respectively (Artavanis-Tsakonas et al., 1999; Justice and Jan, 2002; Koch et al., 2001). Thus, the data described herein showing the inefficient ability of S17-DL1 cells to induce T cell development, together with the use of human progenitors on a mouse stromal cell line by Jaleco et al, serves to clarify the apparent differences between the previously-reported observations and the findings presented here.

An important implication of the work described herein is that the three-dimensional thymic microenvironment is not indispensable for T cell development (Anderson et al., 1996; Carlyle and Zúñiga-Pflücker, 1998; Lind et al., 2001). Lineage commitment, TCR gene rearrangement, and progression to the DP stage following pre-TCR formation can be recapitulated in vitro by HPCs cultured on OP9 cells expressing Delta-like-1. In this regard, part of the observed burst of cellular proliferation appears to take place just prior to the appearance of DP cells, coinciding with when TCR-$\beta$ selection normally occurs (Kruisbeek et al., 2000). In support of this notion, OP9-DL1 cocultures using HPCs derived from recombinase-activating gene (RAG)-2-deficient mice (Shinkai et al., 1992), which are unable to generate a TCR-$\beta$ chain, failed to reach the DP stage of T cell development, and displayed the expected block in T cell differentiation at the CD44$^-$CD25$^+$ stage. Thus, HPCs differentiating on OP9-DL1 cells appear to follow a normal program of early T cell development, as the observed stage-specific expansion and progression to the DP stage appear to be dependent on the induction of TCR$\beta$ rearrangement and the resulting $\beta$-selection-mediate signaling outcomes.

The development of $\gamma\delta$-T cells on OP9-DL1 cells demonstrates that both $\gamma\delta$- and $\alpha\beta$-lineages can develop in the presence of Delta-like-1, suggesting that Notch signals mediated by Delta-like-1 do not influence commitment to the $\gamma\delta$- or $\alpha\beta$-T cell fate (Washburn et al., 1997). Although a number of studies have focused on the role of Notch signaling in CD4 versus CD8 lineage development (Deftos et al., 1998; Deftos et al., 2000; Izon et al., 2001; Robey et al., 1996; Wolfer et al., 2001), the presence of mature TCR$^{hi}$ CD8$^+$ SPs but not CD4$^+$ SP T cells most likely reflects the fact that OP9 cells express MHC class I, but do not express MHC class II. In keeping with this, the appearance of CD4$^+$ CD8$^{lo}$ TCR$^{int}$ cells was frequently observed, which are consistent with cells undergoing the first stages of CD4- or CD8-lineage commitment (Brugnera et al., 2000), while the few CD4$^+$ CD8$^-$ SP cells express TCR levels that are below those of normal CD4 SP thymocytes, and therefore likely represent developmental intermediates. In contrast, a small but significant number of CD4$^-$ CD8$^+$ TCR$^{hi}$ cells are generated, and when isolated, these are capable of responding to TCR stimulation by producing $\gamma$-IFN, demonstrating that mature SP cells can be generated from HPCs induced to differentiate on Delta-like-1-expressing OP9 cells.

In addition to the previous reports addressing the role of Notch receptor/ligand interactions at various stages of lymphocyte development (Deftos et al., 1998; Deftos et al., 2000; Izon et al., 2001; Koch et al., 2001; Pui et al., 1999; Radtke et al., 1999; Robey et al., 1996; Wolfer et al.,2001), this work demonstrates that Delta-like-1-induced signals are responsible for the commitment and differentiation of genetically unmanipulated HPCs into T cells in the absence of a thymic environment. These findings should simplify the experimental approaches heretofore required for the study of T cell differentiation, and may enable the development of immune-reconstitution approaches employing defined sources of stem cells.

Example 10

The Following Method Describes the Procedure to Generate Cells of the T Cell Lineage from ES Cells in an ES/OP9-DL1 Coculture System A. Materials
1. Embryonic stem (ES) cells. Lymphocytes were generated in vitro from ES cell lines (R1, D3, E14K cell lines derived from 129/Sv mice; and ES cells derived from Balb/c and C57B1/6 mice). ES cells were maintained as undifferentiated adherent colonies on monolayers of mouse embryonic fibroblasts (EF).
2. Embryonic fibroblast (EF) cells. Undifferentiated ES cells were maintained on mouse primary EF cells. EF cells were mitotically-inactivated by irradiation (20 Gy) or by treatment with mitomycin-C (Sigma M-0503). If EF cells were treated with mitomycin-C, confluent dishes were incubated with 10 ug/ml mitomycin-C for 2.5 hours at 37° C. The cells were washed 3 times with 1× PBS, then new media was added. For procedures to isolate primary EF cells and maintain feeder layers, see E. J. Robertson (Robertson, E.

J. (1997) *Methods Mol Biol* 75, 173-84. and Robertson, E. J. (Ed.) (1987) Teratocarcinomas and embryonic stem cells: a practical approach., IRL Press, IRL Press, Oxford, UK.
3. OP9-DL1 cells. OP9 cells are adherent cells cultured as monolayers. They were obtained from the RIKEN cell depository. OP9-DL1 cells were prepared as described in Example 1.
4. Leukemia Inhibitory Factor (LIF) (R&D Systems 449-L, Stem Cell Technologies 02740, or Chemicon LIF2010) reconstituted at 5 mg/ml (1000×). Store at −80° C. in small aliquots.
5. Flt-3 Ligand (R&D 308-FK) was reconstituted at 5 mg/ml (1000×) and stored at −80° C. in small aliquots.
6. IL- 7. (R&D Systems 407-ML) was reconstituted at 1 mg/ml (1000×) and stored at −80° C. in small aliquots.
7. IL-15. (R&D Systems 247-IL) was reconstituted at 10 mg/ml (1000×), and stored at −80° C. in small aliquots.

B. Methods
1. ES media. High glucose DMEM was supplemented with 15% FBS, 10.5 ml HSG solution, and 10.5 ml PG2 solution.
2. OP9 media. Freshly reconstituted αMEM was supplemented with 20% FBS and 1× penicillin/streptomycin solution. This media was used to culture OP9 cells and was also used throughout the ES/ OP9-DL1 coculture.
3. Thawing and maintaining ES cells. A vial of ES cells was thawed in a 37° C. water bath, cells were transferred to a 14 ml centrifuge tube containing 10 ml ES media, the cells were pelletted, resuspended in 3 ml ES media and were added to a 6 cm dish of irradiated EF cells. 3 ml of LIF (1000×) was added, and the dish was gently shaken to mix. The media was changed the next day by removing all the media and adding fresh media and LIF. Two days after thawing ES cells, the cells were trypsinized (see below, trypsin passage) and replated onto new EF cells. To maintain ES cells in culture, ES cells were trypsin passaged every other day, and the media was changed on the alternate days. The ES cells were maintained at less than 80-90% confluence (i.e. 80-90% of the surface area is covered with ES cells).
4. Trypsin passage of ES cells. Media was removed from the dish of ES cells, 4 mls of PBS was added, the plate was gently swirled to wash cells, and the PBS was removed. 2 ml of 0.25% trypsin was added to the dish and returned to the incubator for 5 min. The cells were disaggregated by vigorous pipetting and transferred to a 14 ml centrifuge tube. The dish was washed with 6 ml of ES media and transferred to the same 14 ml tube. The cells were pelleted at 500 g for 10 min, and resuspended in 3 ml of ES media. The media was removed from a 6 cm dish of confluent irradiated EF cells, resuspended ES cells were added, 3 ml of LIF was added, and the plate was gently shaken to evenly disperse the cells and LIF.
5. Freezing ES cells. The ES cells were trypsinized, washed, and pelleted . The ES cells were resuspended in cold (4° C.) freezing medium(90% FBS+10% DMSO, tissue culture grade), 1 ml transferred to cryovials (2-4 vials per 6 cm dish of 80% confluent ES cells), and stored in vials at −80° C. freezer overnight. The next day, the vials were transferred to a liquid nitrogen container.
6. Thawing and maintaining OP9-DL1 cells. A vial of OP9-DL1 cells was thawed in a 37° C. water bath, the cells transferred to a 14 ml centrifuge tube containing 10 ml OP9 media, the cells were pelletted, resuspended in 10 ml OP9 media and plated onto a 10 cm dish. The media was changed the next day. When the 10 cm dish of OP9-DL1 cells was 90-95% confluent, the cells were trypsin passaged and 1 dish was split into 4 dishes (OP9 cells in 6-well plates are used on day 8 of coculture, and subsequently). The OP9-DL1 cells were trypsin passaged every 2 to 3 days.
7. Trypsin passage of OP9 cells. Media was removed from the 10 cm dish of OP9-DL1 cells. 10 ml of PBS was added, the plate gently swirled to wash cells, and PBS was removed. 4 ml 0.25% trypsin was added to the dish and it was returned to the incubator for 5 min. The cells were disaggregated by vigorous pipetting and transferred to a 14 ml centrifuge tube. The dish was washed with 10 ml of OP9 media and transferred to the same tube. The cells were resuspended in 12 ml OP9 media and 3 ml aliquots were transferred to four 10 cm dishes. 7 ml of OP9 media was added to bring the volume in each dish to 10 ml, the dish was gently shaked/swirled to evenly distribute the cells.
8. Freezing OP9-DL1 cells. The OP9-DL1 cells were trypsin passaged, washed, and pelleted. The OP9-DL1 cells were maintained in cold (4° C.) freezing medium (90% FBS+ 10% DMSO), added to cryovials (1 vial per 10 cm dish of 85-95% confluent OP9 cells), and transferred to a −80° C. freezer overnight. The next day, vials were transferred to a liquid nitrogen container.
9. ESC/OP9 coculture.
a. Preparing cells. ES cells were thawed onto irradiated EF cells 4 to 6 days prior to the beginning of coculture. The cells were passaged as for maintaining ES cells. OP9-DL1 cells were thawed 4 days prior to the beginning of coculture. Two days prior to beginning the coculture, a confluent 10 cm dish of OP9-DL1 cells was trypsin passaged into 4×10 cm dishes.
b. Day 0. OP9-DL1 cells were at about 85-95% confluent. Old media was aspirated from the OP9-DL1 cells in a 10 cm dish, and 10 ml of OP9 media was added. The media was aspirated off from the ES cell dish. The ES cells were washed once in PBS, and the ES cells were trypsinized. After disaggregating the cells, 6 ml of ES media was added and the cells were transferred to a new 10 cm dish (not an EF monolayer dish) and incubated at 37° C. for 30 min. After the incubation, the non-adherent cells were collected into a tube, pelleted, resuspended in 3 ml ES media, the cells were counted, and $5 \times 10^4$ ES cells were seeded onto a 10 cm dish with OP9-DL1 cells.

c. Day 3. The media of the cocultures was changed. Old OP9 media was aspirated off without disturbing the monolayer. 10 ml of OP9 media was added.

d. Day 5. The old media was aspirated off and the cells were washed with 10 ml PBS without disturbing the cells. The PBS was aspirated off, 4 mls 0.25% trypsin was added and the cells were incubated for 5 min at 37° C. The cells were disaggregated by vigorous pipetting, 8 mls OP9 media was added to neutralize the trypsin, the cells were transferred to a 10 cm dish, and incubated for 30 min at 37° C. to preplate out the OP9-DL1 cells. The non-adherent cells were collected and transferred into a 14 ml tube, pelleted, resuspended in fresh OP9 media, the cells were counted, and $5 \times 10^5$ cells were transferred to a new confluent 10 cm dish of OP9-DL1 cells. Flt-3L was added to a final concentration of 5 ng/ml.

e. Day 8. Small clusters (typically 4-10 cells) of round blast-like cells were visible. Using a 10 ml pipette, the surface of the plate was washed and cells were transferred to a 50 ml tube. The gentle wash was repeated taking care to leave the OP9-DL1 monolayer with other differentiated colonies intact. The dish was checked by microscope to see that very few clusters of round cells remain. The loosely adherent harvested cells were pelletted, resuspended in 3 ml of OP9 media and transferred to new OP9-DL1 monolayers in 6-well plates. The cells were transferred from one 10 cm dish of day 8 cocultures into one well of a 6-well plate with OP9-DL1 cells. Flt-3L was added to the passaged cells. IL-7 was added to a final concentration of 1 ng/ml.

f. Day 10. The media was changed by transferring supernatants from the cocultures into tubes (without disrupting the monolayers). Fresh media was added to wells to prevent the cells from drying out. Cells were pelleted from the supernatant, resuspended in fresh media and gently pipetted back to the same well. The appropriate cytokines, i.e., Flt-3L, and IL-7 were added.

g. Day 12. The cells were trypsin passaged. The cells were disaggregated with vigorous pipetting, transferred a new 10 cm dish to preplate out the OP9-DL1 cells, incubated for 30 min, and non-adherent cells were transferred to new OP9-DL1 monolayers. Alternatively, cells were passaged without trypsin by disaggregating cultures with vigorous pipetting, passing through a 70 mm Nylon mesh filter into a tube, pelleting, resuspending in new media, and transferring to new OP9-DL1 monolayers.

h. Beyond Day 12. To continue cocultures beyond day 12, cells were transferred to new OP9-DL1 cell monolayers every 4 to 10 days with media changes every 2 to 3 days. The passage procedure was followed for day 12. For efficient hematopoietic differentiation it was advisable to leave the proliferating colonies undisturbed as long as possible. However, it was necessary to passage new OP9-DL1 monolayers as the confluent OP9-DL1 cells differentiate into cells that will no longer support further hematopoiesis effectively, and because overconfluent cocultures will begin to "roll up" at the edges as overconfluent OP9-DL1 cells de-attach from the tissue culture plates.

3. Comments

1. Flow cytometry. Progression of lymphocytes differentiating from ES cells can be readily assessed by flow cytometry. Stages of T cell differentiation have been characterized by the expression of various cell surface molecules. Fluorochrome- or biotin-labelled antibodies for flow cytometric analysis can be purchased from Pharmingen or eBiosciences.

2. OP9 differentiation. OP9-DL1 cells that have been maintained in good condition have the morphology of veiled (large cytoplasm) adherent cells with short dendritic-like extensions, and have an overall elongated star-like shape. With prolonged culture the cells become larger with fewer cytoplasmic extension, and take on a triangular(scalene) shape. The latter will not suffice for hematopoietic induction from ES cells but should still support hematopoiesis from tissue explants such as fetal liver or bone marrow. In addition, when OP9-DL1 cells are maintained in culture for prolonged periods and/or are grown overconfluent, they will differentiate into large cells containing many fat droplets. During the course of ES/OP9-DL1 cocultures, cells are seeded onto nearly confluent OP9-DL1 monolayers, which become overconfluent within days. Thus, the appearance of some cells containing fat droplets during ES/OP9-DL1 coculture is normal. However, if these cells predominate, the OP9-DL1 monolayer will not efficiently support hematopoietic differentiation.

4. Remarks

ES cells can efficiently differentiate into T lymphocytes in vitro by coculture on the stromal cell preparation, OP9-DL1 (FIG. 9). Evidence supports that these lymphocytes are functionally analogous to lymphocytes in vivo (FIG. 9). Thus, ES/OP9 cocultures can serve as a model system for the study of lymphocyte differentiation and for functional aspects of T cell biology.

Example 11

Mice. Timed-pregnant B6-Ly5.2 mice were obtained from the National Cancer Institute, Frederick Cancer Research and Development Center (Frederick, Md.). RAG2-deficient mice were bred and maintained in our animal facility.

Fetal thymic organ culture: Lymphocyte depleted fetal thymic lobes were prepared by culturing the thymic lobes from C57/B16 (CD45.1) day 15 embryoes in medium containing 1.25 mM deoxyguanosine for 5 days as previously described. CD25$^+$ CD45$^+$ ESC-derived T cell progenitors (CD45.2$^+$) were purified by flow cytometric cell sorting from day 11-12 ESC/OP9-DL1 cultures and $1 \times 10^4$ cells were seeded into each pair of lymphocyte depleted thymic lobes and cultured for 14 days.

Adoptive transfer of ESC reconstituted lobes: Fetal thymic lobes were reconstituted with ESC-derived T cell progenitors as described above and cultured in vitro for 6 days, followed by adoptive transfer under the skin of Rag2$^{-/-}$ recipient mice. After 3 weeks, the host animals were sacrificed, and the spleen and lymph nodes were analyzed for ESC-derived T cells by flow cytometry (ESC-derived T cells expressed CD45.2 and TCR-b).

LCMV Challenge, and Cytotoxicity Assay: RAG2$^{-/-}$ mice were reconstituted with ESC-derived T cell progenitors as described above, except that fetal thymic lobes from RAG2$^{-/-}$ mice fetuses were used. Two weeks after reconstitution, recipient mice and wild-type B6 control mice were infected i.v. with 2000 PFU LCMV. 8 days after infection, splenocytes were isolated, and the cytolytic activity of ESC-derived T cells was determined in a $^{51}$Cr-release assay. EL4 target cells were coated with the LCMV glycoprotein peptide gp33 or a control adenovirus-derived peptide (AV) at a concentration of 1 μM and labeled with $^{51}$Cr for 1.5 hour. After washing, $10^4$ target cells were mixed with ESC-derived T cells from reconstituted RAG2$^{-/-}$ animals at ratios of 90:1, 30:1, 10:1, and 3:1 in 96 well round-bottom plates. Cells were incubated for 5 hours, and then supernatants were analyzed for $^{51}$Cr release associated with cytolytic activity.

Figure 16:
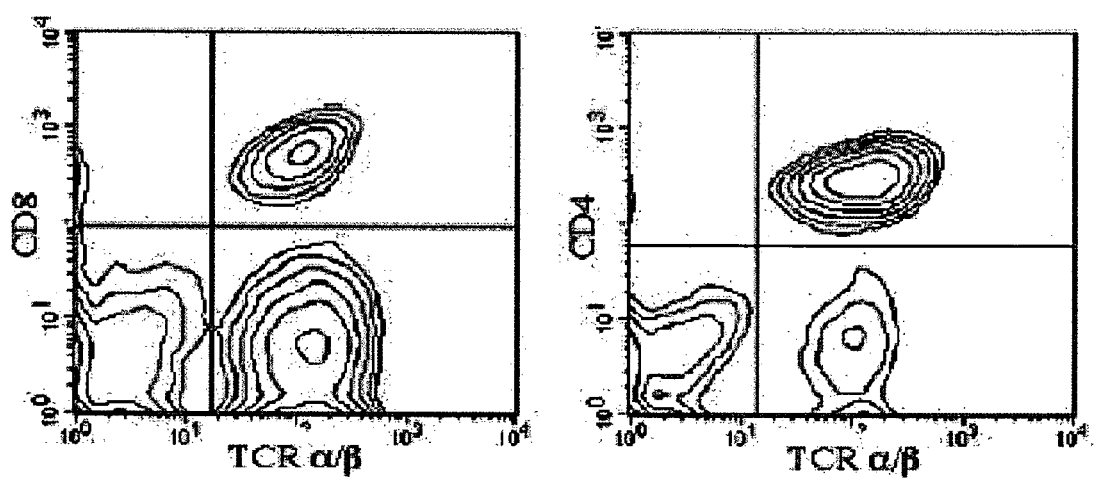
FIG. 16. In vivo reconstitution of T cells from in vitro-differentiated ES cells. ES cells were cocultured with OP9-DL1 cells for 13 days, sorted for CD25+ cells, and transferred to host FTOCs. The reconstituted FTOCs were cocultured for 5 days, and then grafted under the skin of RAG-2-deficient mice. After 3 weeks, lymph nodes were isolated from the engrafted mice and cell suspensions were analyzed for the presence of ES cell-derived T cells. Flow cytometric analysis for the cell surface expression of TCR-βCD4 or CD8 is shown.

A cellular composition comprising immature T lineage cells (CD25$^+$ CD44$^\pm$) differentiated from ES cells, prepared as described in Example 9, was transferred to a host fetal thymus organ culture (FTOC) which were derived from deoxyguanosine-treated/irradiated fetal thymic lobes. After 5 days in culture, the FTOCs were grafted under the skin of sublethally-irradiated (5 Gy) RAG-deficient mice, which are unable to generate TCR-bearing cells. After 3 weeks, >75% of the cells in the lymph nodes of the host mouse were ES cell-derived T cells (FIG. 16), CD4$^+$ CD8$^-$ TCR$^{hi}$ and CD4$-$ CD8+ TCR$^{hi}$. Thus, immature T lineage cells obtained from the ES/OP9 cocultures fully reconstituted the T cell compartment, including the lymph nodes (shown, FIG. 16) and other sites such as the spleen, bone marrow, and thymus of the host mouse.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the cell lines, vectors, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

TABLE 1

| Gene | Forward Primer | Reverse Primer | Product Size | Anneal Temp | SEQ ID NOS. |
|---|---|---|---|---|---|
| PU.1 | ATGGAAGGGTTTTCCCTCACCGCC | GTCCACGCTCTGCAGCTCTGTGAA | 216 bp | 61 | 27-28 |
| E47 | CGCACTGACCACGAGCTTCAC | TCCAGGGACAGCACCTCATCTG | 345 bp | 57 | 29-30 |
| IL7Ra | AGCAACTGGACGCATGTATC | TCACCATCTCTGTAGTCAGG | 656 bp | 55 | 31-32 |
| Rag-1 | TGCAGACATTCTAGCACTCTGG | ACATCTGCCTTCACGTCGAT | 556 bp | 60 | 33-34 |
| λ5 | TTCCATCTAAGCCCCAGTTTTG | CCCCATCTACCTTCCAGTCCA | 198 bp | 55 | 35-36 |
| IGa | GCCAGGGGTCTAGAAGC | TCACTTGGCACCCAGTACAA | 308 bp | 57 | 37-38 |
| CD3e | ATGGCCAAGAGCTGC | AGAATACAGGTCCCGCT | 384 bp | 57 | 39-40 |
| Pre-Ta | CAGAGCCTCCTCCCCCAACAG | GCTCAGAGGGGTGGGTAAGAT | 707 bp | 51 | 41-42 |
| HEB | TAGTCGATCAGCTTCGATGG | GCTCTCTGGCATTGTTAGCC | 383 bp | 55 | 43-44 |
| HES-1 | GCCAGTGTCAACACGACACCG | TCACCTCGTTCATGCACTCG | 310 bp | 56 | 45-46 |
| GATA-3 | ATCCGCCCTATGTGCCCGAGTA | ATGTGGCTGGAGTGGCTGAAGG | 583 bp | 61 | 47-48 |
| β-Actin | GTGGGCCGCTCTAGGCACCAA | CTCTTTGATGTCACGCACGATTTC | 539 bp | 55 | 49-50 |

TABLE 2

Progenitor frequency analysis for HPCs cultured on OP9-GFP or OP9-DL1 cells.

| Lineage analyzed[a] | Progenitor Frequency$^{-1}$ [95% confidence limits][b] |
|---|---|
| T cells[c] | 17 [12.6-22.7] |
| B cells[d] | 6 [4.7-8.4] |
| Myeloid cells[d] | 5 [3.5-6.3] |

[a]Individual wells (n = 36) were analyzed for the generation of T cells (CD4$^+$ CD8$^+$); B cells (CD19$^+$); and myeloid cells (CD11b$^+$) (FIG. 7).
[b]Statistical analysis was performed using the method of maximum likelihoodapplied to the Poisson model.
[c]T cells were generated by culturing HPCs on OP9-DL1 cells.
[d]B cells and myeloid cells were generated by culturing HPCs on OP9-GFP cells.

REFERENCES

Anderson, G., Moore, N. C., Owen, J. J., and Jenkinson, E. J. (1996). Cellular interactions in thymocyte development. Annu. Rev. Immunol. 14, 73-99.

Anderson, M. K., Weiss, A. H., Hernandez-Hoyos, G., Dionne, C. J. & Rothenberg, E. V. (2002) Constitutive expression of PU.1 in fetal hematopoietic progenitors blocks T cell development at the pro-T cell stage. *Immunity* 16, 285-96.

Artavanis-Tsakonas, S., Rand, M. D., and Lake, R. J. (1999). Notch signaling: cell fate control and signal integration in development. Science 284, 770-6.

Bain, G. et al. (1994) E2A proteins are required for proper B cell development and initiation of immunoglobulin gene rearrangements. *Cell* 79, 885-92

Barndt, R. J., Dai, M. & Zhuang, Y. (2000). Functions of E2A-HEB heterodimers in T-cell development revealed by a dominant negative mutation of HEB. *Mol Cell Biol* 20, 6677-85.

Bertrand, F. E., Eckfeldt, C. E., Lysholm, A. S., and LeBien, T. W. (2000). Notch-1 and Notch-2 exhibit unique patterns of expression in human B-lineage cells. *Leukemia* 14, 2095-102.

Brugnera, E., Bhandoola, A., Cibotti, R., Yu, Q., Guinter, T. I., Yamashita, Y., Sharrow, S. O., and Singer, A. (2000). Coreceptor reversal in the thymus: signaled CD4+8+ thymocytes initially terminate CD8 transcription even when differentiating into CD8+ T cells. *Immunity* 13, 59-71.

Carlyle, J. R., Michie, A. M., Furlonger, C., Nakano, T., Lenardo, M. J., Paige, C. J., and Zúñiga-Pflücker, J. C. (1997). Identification of a novel developmental stage marking lineage commitment of progenitor thymocytes. J Exp Med 186, 173-82.

Carlyle, J. R., and Zúñiga-Pflücker, J. C. (1998). Requirement for the thymus in ab T lymphocyte lineage commitment. Immunity 9, 187-97.

Collins, L. S., and Dorshkind, K. (1987). A stromal cell line from myeloid long-term bone marrow cultures can support myelopoiesis and B lymphopoiesis. J Immunol 138, 1082-7.

Cumano, A., and Godin, I. (2001). Pluripotent hematopoietic stem cell development during embryogenesis. Curr Opin Immunol 13, 166-71.

Deftos, M. L., He, Y. W., Ojala, E. W., and Bevan, M. J. (1998). Correlating notch signaling with thymocyte maturation. Immunity 9, 777-86.

Deftos, M. L., Huang, E., Ojala, E. W., Forbush, K. A., and Bevan, M. J. (2000). Notch1 signaling promotes the maturation of CD4 and CD8 SP thymocytes. Immunity 13, 73-84.

Dorshkind, K. (1990). Regulation of hemopoiesis by bone marrow stromal cells and their products. Annu Rev Immunol 8, 111-37.

Engel, I., Johns, C., Bain, G., Rivera, R. R. & Murre, C. (2001). Early thymocyte development is regulated by modulation of E2A protein activity. *J Exp Med* 194, 733-45.

Fazekas de St, G. (1982). The evaluation of limiting dilution assays. J Immunol Methods 49, RI 1-23.

Izon, D. J., Punt, J. A., Xu, L., Kamell, F. G., Allman, D., Myung, P. S., Boerth, N. J., Pui, J. C., Koretzky, G. A., and Pear, W. S. (2001). Notch1 regulates maturation of CD4+ and CD8+ thymocytes by modulating TCR signal strength. Immunity 14, 253-64.

Jaleco, A. C., Neves, H., Hooijberg, E., Gameiro, P., Clode, N., Haury, M., Henrique, D., and Parreira, L. (2001). Differential effects of Notch ligands Delta-1 and Jagged-1 in human lymphoid differentiation. J Exp Med 194, 991-1002.

Justice, N. J., and Jan, Y. N. (2002). Variations on the Notch pathway in neural development. Curr Opin Neurobiol 12, 64-70.

Kawamoto, H., Ohmura, K., Fujimoto, S., and Katsura, Y. (1999). Emergence of T cell progenitors without B cell or myeloid differentiation potential at the earliest stage of hematopoiesis in the murine fetal liver. J Immunol 162, 2725-31.

Koch, U., Lacombe, T. A., Holland, D., Bowman, J. L., Cohen, B. L., Egan, S. E., and Guidos, C. J. (2001). Subversion of the T/B lineage decision in the thymus by lunatic fringe-mediated inhibition of Notch-1. Immunity 15, 225-36.

Kodama, H., Nose, M., Niida, S., and Nishikawa, S. (1994). Involvement of the c-kit receptor in the adhesion of hematopoietic stem cells to stromal cells. Exp Hematol 22, 979-84.

Kruisbeek, A. M., Haks, M. C., Carleton, M., Michie, A. M., Zúñiga-Pflücker, J. C., and Wiest, D. L. (2000). Branching out to gain control: how the pre-TCR is linked to multiple functions. Immunol Today 21, 637-44.

Kuroda, K., Tani, S., Tamura, K., Minoguchi, S., Kurooka, H., and Honjo, T. (1999). Delta induced Notch signaling mediated by RBP-J inhibits MyoD expression and myogenesis. J Biol Chem 274, 7238-44.

Lind, E. F., Prockop, S. E., Porritt, H. E., and Petrie, H. T. (2001). Mapping precursor movement through the postnatal thymus reveals specific microenvironments supporting defined stages of early lymphoid development. J Exp Med 194, 127-34.

MacDonald, H. R., Wilson, A., and Radtke, F. (2001). Notch1 and T-cell development: insights from conditional knockout mice. Trends Immunol 22, 155-60.

Mombaerts, P. et al. (1992) RAG-1-deficient mice have no mature B and T lymphocytes. Cell 68, 869-77.

Nakano, T., Kodama, H. & Honjo, T. (1994) Generation of lymphohematopoietic cells from embryonic stem cells in culture. *Science* 265, 1098-101.

Orkin, S. H. & Morrison, S. J. (2002) Stem-cell competition. *Nature* 418, 25-7.

Osmond, D. G. (1994). Production and selection of B lymphocytes in bone marrow: lymphostromal interactions and apoptosis in normal, mutant and transgenic mice. Adv Exp Med Biol 355, 15-20.

Peschon, J. J. et al. (1994). Early lymphocyte expansion is severely impaired in interleukin 7 receptor-deficient mice. *J Exp Med* 180, 1955-60.

Pui, J. C., Allman, D., Xu, L., DeRocco, S., Karnell, F. G., Bakkour, S., Lee, J. Y., Kadesch, T., Hardy, R. R., Aster, J. C., and Pear, W. S. (1999). Notch1 expression in early lymphopoiesis influences B versus T lineage determination. Immunity 11, 299-308.

Radtke, F., Wilson, A., Stark, G., Bauer, M., van Meerwijk, J., MacDonald, H. R., and Aguet, M.(1999). Deficient T cell fate specification in mice with an induced inactivation of Notch1. Immunity 10, 547-58.

Robey, E., Chang, D., Itano, A., Cado, D., Alexander, H., Lans, D., Weinmaster, G., and Salmon, P. (1996). An activated form of Notch influences the choice between CD4 and CD8 T cell lineages. Cell 87, 483-92.

Rodewald, H.-R., Kretzschmar, K., Takeda, S., Hohl, C., and Dessing, M. (1994). Identification of pro-thymocytes in murine fetal blood: T lineage commitment can precede thymus colonization. EMBO. J. 13, 4229-4240.

Rothenberg, E. V., Telfer, J. C. & Anderson, M. K. (1999). Transcriptional regulation of lymphocyte lineage commitment. *Bioessays* 21, 726-42.

Schmitt, T. M. & Zuniga-Pflucker, J. C. (2002). Induction of T cell development from hematopoietic progenitor cells by delta-like-1 in vitro. *Immunity* 17, 749-56.

Scott, E. W., Simon, M. C., Anastasi J. & Singh, H. (1994). Requirement of transcription factor PU.1 in the development of multiple hematopoietic lineages. *Science* 265, 1573-7.

Shinkai, Y., Rathbun, G., Lam, K.-P., Oltz, E. M., Stewart, V., Mendelsohn, M., Charron, J., Datta, M., Young, F., Stall, A. M., and Alt, F. W. (1992). RAG-2-deficient mice lack mature lymphocytes owing to inability to initiate V(D)J rearrangement. Cell 68, 855-867.

Shortman, K., and Wu, L. (1996). Early T lymphocyte progenitors. Ann. Rev. Immunol. 14, 29-47.

Taniguchi, Y., Karlstrom, H., Lundkvist, J., Mizutani, T., Otaka, A., Vestling, M., Bernstein, A., Donoviel, D., Lendahl, U., and Honjo, T. (2002). Notch receptor cleavage depends on but is not directly executed by presenilins. Proc Natl Acad Sci U S A 99, 4014-9.

ten Boekel, E., Melchers, F., and Rolink, A. G. (1997). Changes in the V(H) gene repertoire of developing precursor B lymphocytes in mouse bone marrow mediated by the pre-B cell receptor. Immunity 7, 357-68.

Ting, C. N., Olson, M. C., Barton, K. P. & Leiden, J. M. (1996). Transcription factor GATA-3 is required for development of the T-cell lineage. *Nature* 384, 474-8.

Tomita, K. et al. (1999). The bHLH gene Hes1 is essential for expansion of early T cell precursors. *Genes Dev* 13, 1203-10.

Washburn, T., Schweighoffer, E., Gridley, T., Chang, D., Fowlkes, B. J., Cado, D., and Robey, E. (1997). Notch activity influences the alphabeta versus gammadelta T cell lineage decision. Cell 88, 833-43.

Wolfer, A., Bakker, T., Wilson, A., Nicolas, M., Ioannidis, V., Littman, D. R., Wilson, C. B., Held, W., MacDonald, H. R., and Radtke, F. (2001). Inactivation of Notch 1 in immature thymocytes does not perturb CD4 or CD8T cell development. Nat Immunol 2, 235-41.

Wolfer, A., Wilson, A., Nemir, M., MacDonald, H. R., and Radtke, F. (2002). Inactivation of Notch1 impairs VDJbeta rearrangement and allows pre-TCR-independent survival of early alpha/beta lineage thymocytes. Immunity 16, 869-79.

Zhuang, Y., Soriano, P. & Weintraub, H. (1994). The helix-loop-helix gene E2A is required for B cell formation. *Cell* 79, 875-84.

We claim:

1. A method of producing cells of the T cell lineage comprising culturing stem cells or progenitor cells that are capable of differentiating into cells of the T cell lineage with a cell preparation comprising OP9 stromal cells that have been modified to express a Notch ligand that supports T cell lymphopoiesis but does not support B cell lymphopoiesis of stem cells or progenitor cells, wherein the Notch ligand is Delta-like-1 or Delta-like-4 to produce T cells of one or more of the following lineages:

(a) TCR-αβ⁺ CD4⁻CD8⁺ T cells; and/or (b) TCR-γδ⁺ T cells.

2. The method according to claim 1, wherein the cells that are capable of differentiating into cells of the T lineage are human cells selected from hematopoietic progenitor cells, hematopoietic stem cells and embryonic stem cells.

3. The method of claim 1, further comprising formulating the produced cells in a pharmaceutically acceptable carrier or excipient.

4. A method for expanding cells of the T cell lineage comprising:

(a) culturing stem cells or progenitor cells capable of differentiating into cells of the T cell lineage with a cell preparation comprising OP9 stromal cells that have been modified to express a Notch ligand that supports T cell lymphopoiesis but does not support B cell lymphopoiesis of stem cells or progenitor cells, wherein the Notch ligand is Delta-like-1 or Delta-like-4 and wherein the T cells produced comprise T cells of one or more of the following lineages:

(i) CD4⁻ CD8⁻ CD25⁺ CD44⁺ double negative T cells;

(ii) CD4⁻ CD8⁻ CD25⁺ CD44⁻ double negative T cells;

(iii) TCR-αβ⁺ CD4⁻CD8⁺ T cells; and/or (iv) TCR-γδ⁺ T cells; and (b) isolating increased numbers of the T cell lineage, wherein the number of cells is increased by at least about 10 to 15 fold compared to the stem cells or progenitor cells cultured in step (a).

5. The method as claimed in claim 1, wherein the OP9 cells comprise the Delta-like-1 nucleic acid sequence shown in SEQ ID NO:8 or SEQ ID NO:9.

6. The method as claimed in claim 1, wherein the OP9 cells comprise the Delta-like-4 nucleic acid sequence shown in SEQ ID NO:10 or SEQ ID NO:11.

7. The method as claimed in claim 4, wherein the OP9 cells comprise the Delta-like-1 nucleic acid sequence shown in SEQ ID NO:8 or SEQ ID NO:9.

8. The method as claimed in claim 4, wherein the OP9 cells comprise the Delta-like-4 nucleic acid sequence shown in SEQ ID NO:10 or SEQ ID NO:11.

* * * * *